(12) United States Patent
Lynn et al.

(10) Patent No.: US 7,998,122 B2
(45) Date of Patent: *Aug. 16, 2011

(54) LUER RECEIVER AND METHOD FOR FLUID TRANSFER

(75) Inventors: Lawrence A. Lynn, Delaware, OH (US); Weston Harding, Lehi, UT (US); Edmund Robert Purdy, Fruit Heights, UT (US)

(73) Assignee: Becton, Dickinson & Company, Franklin Lakes, NJ (US)

( * ) Notice: Subject to any disclaimer, the term of this patent is extended or adjusted under 35 U.S.C. 154(b) by 956 days.

This patent is subject to a terminal disclaimer.

(21) Appl. No.: 11/350,059

(22) Filed: Feb. 9, 2006

(65) Prior Publication Data

US 2006/0129112 A1 Jun. 15, 2006

Related U.S. Application Data

(63) Continuation of application No. 09/635,153, filed on Aug. 8, 2000, now Pat. No. 7,033,339, which is a continuation-in-part of application No. 09/322,037, filed on May 28, 1999, now Pat. No. 6,171,287.

(60) Provisional application No. 60/087,162, filed on May 29, 1998, provisional application No. 60/101,998, filed on Sep. 28, 1998.

(51) Int. Cl.
*A61M 5/14* (2006.01)
(52) U.S. Cl. ...................................................... 604/256
(58) Field of Classification Search .................. 604/201, 604/203, 236–238, 246–256, 167.01–167.06
See application file for complete search history.

(56) References Cited

U.S. PATENT DOCUMENTS

| 2,546,672 A | 3/1951 | Clair |
| 3,067,425 A | 12/1962 | Colley |
| 3,577,992 A | 5/1971 | Merry |
| 3,659,587 A | 5/1972 | Baldwin |

(Continued)

FOREIGN PATENT DOCUMENTS

JP 54-150386 11/1979

(Continued)

OTHER PUBLICATIONS

Protest filed Dec. 27, 2002 in JP Patent Appl. No. 2000-550551.

(Continued)

*Primary Examiner* — Matthew F Desanto
(74) *Attorney, Agent, or Firm* — Banner & Witcoff, Ltd

(57) ABSTRACT

An improved luer lock receiving septum having a configuration which provides rapid and tight resealing and yet allows penetration of the septum by the luer tip with a low penetration force. The elongated septum includes an upper portion of enlarged diameter having a target surface, a central slit, and a central, lower septum extension projecting about the slit below the upper portion and into a housing so that following luer insertion there is provided sufficient room for both the laterally displaced extension of the septum, the luer taper, and the housing to be received into a conventional luer lock connector. The septum is further preferably configured to minimize or eliminate the negative pressure deflection normally associated with the withdrawal of the large diameter luer cannula from an enclosed fluid filled lumen or chamber, by substantially isolating the lumen or chamber from the septum material displacement resultant from luer insertion. In an exemplary embodiment, the luer receiving septum is provided at a port of a stop cock.

34 Claims, 37 Drawing Sheets

U.S. PATENT DOCUMENTS

| | | |
|---|---|---|
| 3,986,508 A | 10/1976 | Barrington |
| 4,084,606 A | 4/1978 | Mittleman |
| 4,143,853 A | 3/1979 | Abramson |
| 4,197,848 A | 4/1980 | Garrett |
| 4,197,876 A | 4/1980 | Lobdell |
| 4,207,923 A | 6/1980 | Giurtino |
| 4,314,555 A | 2/1982 | Sagae |
| 4,496,348 A | 1/1985 | Genese |
| 4,496,350 A | 1/1985 | Cosentino |
| 4,511,359 A | 4/1985 | Vaillancourt |
| 4,512,766 A | 4/1985 | Vailancourt |
| 4,685,654 A | 8/1987 | Hu |
| 4,758,225 A | 7/1988 | Cox |
| 4,763,648 A | 8/1988 | Wyatt |
| 4,768,568 A | 9/1988 | Fournier |
| 4,807,666 A | 2/1989 | Morse |
| 4,809,679 A | 3/1989 | Shimonaka |
| 4,820,280 A | 4/1989 | Berch |
| 4,834,152 A | 5/1989 | Howson |
| 4,857,062 A | 8/1989 | Russell |
| 4,895,346 A | 1/1990 | Steigerwald |
| 4,929,235 A | 5/1990 | Merry |
| 4,935,010 A | 6/1990 | Cox et al. |
| 4,950,257 A | 8/1990 | Hibbs |
| 4,950,260 A | 8/1990 | Bonaldo |
| 5,009,391 A | 4/1991 | Steigerwald |
| 5,059,186 A | 10/1991 | Yamamoto |
| 5,064,416 A | 11/1991 | Newgard |
| 5,085,645 A | 2/1992 | Purdy |
| 5,100,394 A | 3/1992 | Dudar |
| 5,108,380 A | 4/1992 | Herlitze |
| 5,114,400 A | 5/1992 | Lynn |
| 5,135,026 A | 8/1992 | Manska |
| 5,135,489 A | 8/1992 | Jepson et al. |
| 5,144,972 A | 9/1992 | Dryden |
| 5,147,305 A | 9/1992 | Nakamura |
| 5,149,327 A | 9/1992 | Oshiyama |
| 5,158,554 A | 10/1992 | Jepson |
| 5,171,234 A | 12/1992 | Jepson |
| 5,176,653 A | 1/1993 | Matais |
| 5,178,607 A | 1/1993 | Lynn |
| 5,199,948 A * | 4/1993 | McPhee ............... 604/86 |
| 5,201,725 A | 4/1993 | Kling |
| 5,203,775 A | 4/1993 | Frank et al. |
| 5,211,370 A | 5/1993 | Powers |
| 5,211,634 A | 5/1993 | Vaillancourt |
| 5,211,638 A | 5/1993 | Dudar |
| 5,215,538 A | 6/1993 | Larkin |
| 5,221,271 A | 6/1993 | Nicholson |
| 5,242,393 A | 9/1993 | Brimhall et al. |
| 5,242,432 A | 9/1993 | Defrank |
| 5,251,873 A | 10/1993 | Atkinson |
| 5,273,533 A | 12/1993 | Bonaldo |
| 5,290,222 A | 3/1994 | Feng |
| 5,295,657 A | 3/1994 | Atkinson |
| 5,295,658 A | 3/1994 | Atkinson |
| 5,295,969 A | 3/1994 | Fischell et al. |
| 5,300,034 A | 4/1994 | Behnke |
| 5,352,205 A | 10/1994 | Dales |
| 5,354,275 A | 10/1994 | Behnke |
| 5,356,396 A | 10/1994 | Wyatt |
| 5,360,413 A | 11/1994 | Leason |
| 5,390,898 A | 2/1995 | Smedley |
| 5,395,342 A | 3/1995 | Yoon |
| 5,396,925 A | 3/1995 | Poli |
| 5,402,982 A | 4/1995 | Atkinson |
| 5,403,293 A | 4/1995 | Grabenkort |
| 5,405,331 A | 4/1995 | Behnke |
| 5,409,461 A | 4/1995 | Steinman |
| 5,417,673 A | 5/1995 | Gordon |
| 5,429,616 A | 7/1995 | Schaffer |
| 5,441,486 A | 8/1995 | Yoon |
| 5,441,487 A | 8/1995 | Vedder |
| 5,447,501 A | 9/1995 | Karlsson |
| 5,449,145 A | 9/1995 | Wortrich |
| 5,456,284 A | 10/1995 | Ryan |
| 5,466,219 A | 11/1995 | Lynn |
| 5,470,319 A | 11/1995 | Mayer |
| 5,474,107 A | 12/1995 | Hayes |
| 5,474,544 A | 12/1995 | Lynn |
| 5,498,247 A | 3/1996 | Brimhall |
| 5,501,426 A | 3/1996 | Atkinson |
| 5,514,098 A | 5/1996 | Pfoslgraf |
| 5,522,804 A | 6/1996 | Lynn |
| 5,531,810 A | 7/1996 | Fullenmann |
| 5,533,708 A | 7/1996 | Atkinson |
| 5,542,933 A | 8/1996 | Marks |
| 5,549,651 A | 8/1996 | Lynn |
| 5,556,387 A | 9/1996 | Mollenauer |
| 5,569,222 A | 10/1996 | Haselhorst |
| 5,575,777 A | 11/1996 | Cover |
| 5,578,059 A | 11/1996 | Patzer |
| 5,603,706 A | 2/1997 | Wyatt |
| 5,616,130 A | 4/1997 | Mayer |
| 5,632,735 A | 5/1997 | Wyatt |
| 5,697,914 A | 12/1997 | Brimhall |
| 5,697,915 A | 12/1997 | Lynn |
| 5,699,821 A | 12/1997 | Paradis |
| 5,727,770 A | 3/1998 | Dennis |
| 5,749,859 A | 5/1998 | Powell |
| 5,749,861 A | 5/1998 | Guala |
| 5,769,825 A | 6/1998 | Lynn |
| RE35,841 E | 7/1998 | Frank et al. |
| 5,788,675 A | 8/1998 | Mayer |
| 5,797,897 A | 8/1998 | Jepson |
| 5,807,348 A | 9/1998 | Zinger |
| 5,810,780 A | 9/1998 | Brimhall |
| 5,820,601 A | 10/1998 | Mayer |
| 5,832,959 A | 11/1998 | Szymczakowski |
| 5,848,994 A | 12/1998 | Richmond |
| 5,871,500 A | 2/1999 | Jepson |
| 5,902,298 A | 5/1999 | Niedospiel, Jr. et al. |
| 5,911,705 A | 6/1999 | Howell |
| 5,921,419 A | 7/1999 | Niedospiel, Jr. et al. |
| 5,935,110 A | 8/1999 | Brimhall |
| 5,951,515 A | 9/1999 | Osterlind |
| 5,957,898 A * | 9/1999 | Jepson et al. ............... 604/256 |
| 5,967,490 A | 10/1999 | Pike |
| 6,077,244 A | 6/2000 | Botich |
| 6,139,534 A | 10/2000 | Niedospiel, Jr. et al. |
| 6,171,287 B1 * | 1/2001 | Lynn et al. ............... 604/256 |
| 6,206,851 B1 | 3/2001 | Prosl |
| 6,217,556 B1 | 4/2001 | Ellingson |
| 6,224,569 B1 | 5/2001 | Brimhall |
| 6,228,060 B1 | 5/2001 | Howell |
| 6,228,065 B1 | 5/2001 | Lynn |
| 6,261,282 B1 | 7/2001 | Jepson |
| RE37,357 E | 9/2001 | Lynn |
| 6,344,033 B1 | 2/2002 | Jepson |
| 6,485,473 B1 | 11/2002 | Lynn |
| 6,506,181 B2 | 1/2003 | Meng |
| RE38,145 E | 6/2003 | Lynn |
| 6,699,221 B2 | 3/2004 | Vaillancourt |
| 7,033,339 B1 * | 4/2006 | Lynn ............... 604/256 |
| 2001/0053895 A1 | 12/2001 | Vaillancourt |
| 2002/0072712 A1 | 6/2002 | Nool |

FOREIGN PATENT DOCUMENTS

| | | |
|---|---|---|
| JP | 58-19222 | 2/1983 |
| JP | 60-184507 | 12/1985 |
| JP | 62-87605 | 6/1987 |
| JP | 63-130038 | 6/1988 |
| JP | 63-188001 | 8/1988 |
| JP | 2-116404 | 9/1990 |
| JP | 5-54970 | 2/1992 |
| JP | 4-327826 | 11/1992 |
| JP | 5-28351 | 4/1993 |
| JP | 10-512946 | 12/1998 |
| WO | WO 90/11103 | 10/1990 |
| WO | WO 96/23158 | 8/1996 |
| WO | WO 98/23313 | 6/1998 |
| WO | WO 98/52631 | 11/1998 |

OTHER PUBLICATIONS

Translation of claims as hand-amended with amendatory response filed Jan. 7, 2003 in JP Patent Appl. No. 2000-550551.

Official Action mailed Jul. 7, 2003 in JP Patent Appl. No. 2000-550551 (English Translation).

Protest filed Jul. 11, 2003 in JP Patent Appl. No. 2000-550551.

Protest filed Mar. 2, 2004 in JP Patent Appl. No. 2000-550551.

Trial Decision dated Jun. 18, 2007 in JP Patent Appl. No. 2000-550551 (English Translation).

Plaintiffs First Brief filed Dec. 18, 2007 in Court Action pertaining to JP Patent Appl. No. 2000-550551 (English Translation).

Excerpt of Defendant's Brief (1) in Court Action pertaining to JP Patent Appl. No. 2000-550551 (English Translation).

Plaintiffs Second Brief dated Mar. 14, 2008 in Court Action pertaining to JP Appl. No. 2000-550551 (English Translation) and including Exhibits A-6 through A-10.

Plaintiffs and Participant's Third Brief dated May 23, 2008 in Court Action pertaining to JP Patent Appl. No. 2000-550551 (English Translation).

Defendant's Brief (2) dated Jul. 2, 2008 in Court Action pertaining to JP Patent Appl. No. 2000-550551 (English Translation).

Plaintiffs and Participant's Fourth Brief dated Aug. 15, 2008 in Court Action pertaining to JP Patent Appl. No. 2000-550551 (English Translation).

Defendant's Brief (3) dated Sep. 24, 2008 in Court Action pertaining to JP Patent Appl. No. 2000-550551 (English Translation).

Amendment and Argument filed Apr. 10, 2009 in JP Patent Appl. No. 2000-550551 (following remand in JPO), including English translation of revised and renumbered claims 1-56.

JP Patent 4323721 issued on JP Patent Appl. No. 2000-550551 (including English translations of Sep. 2, 2009 Japanese Official Patent Gazette publication, and Published Japanese Claims).

\* cited by examiner

*Fig. 2*
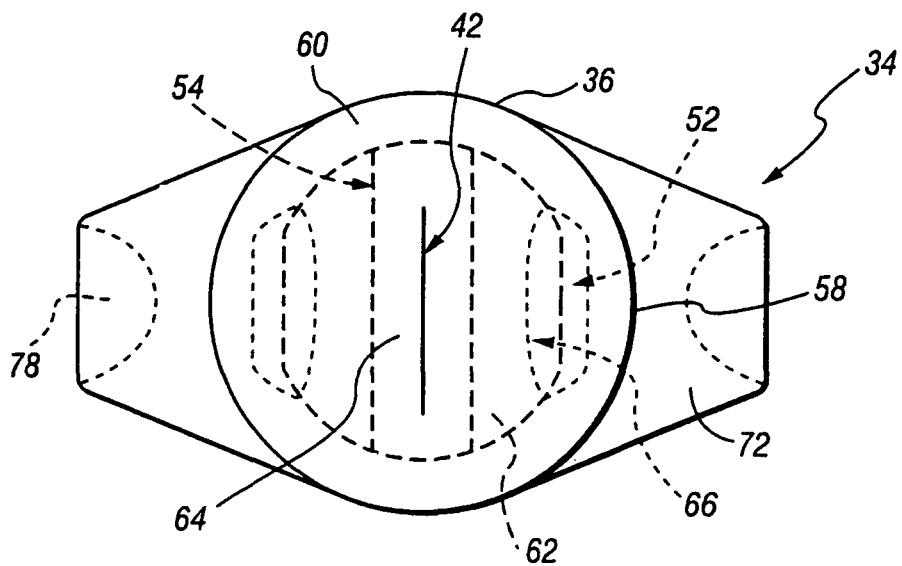
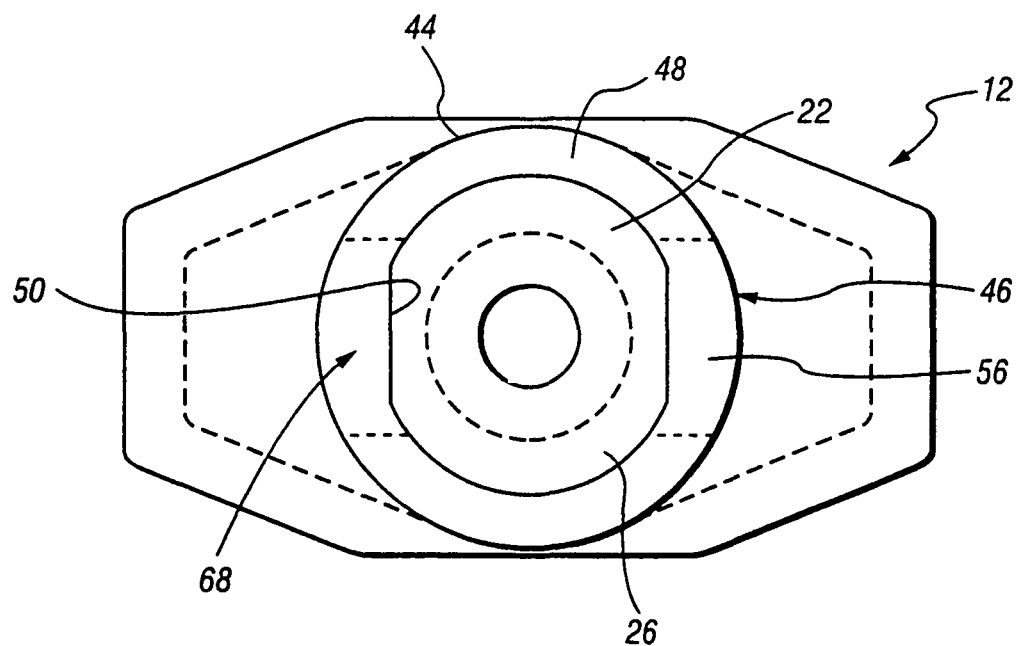
*Fig. 3*

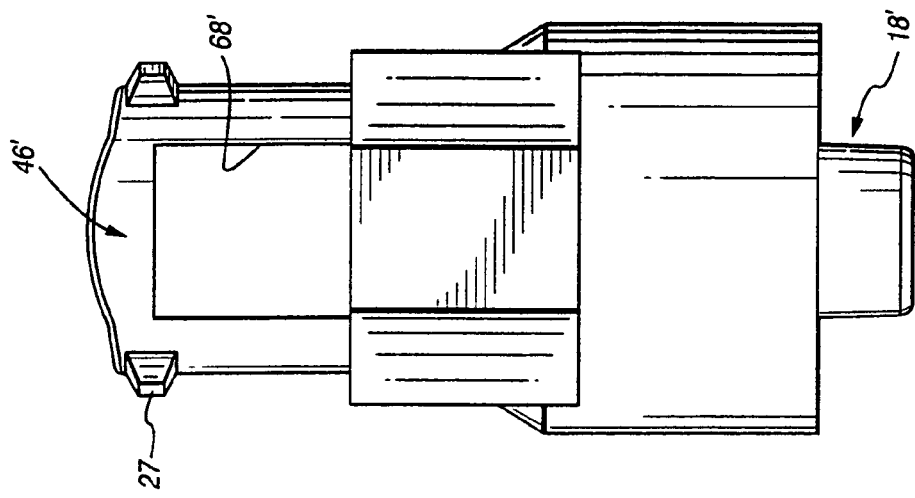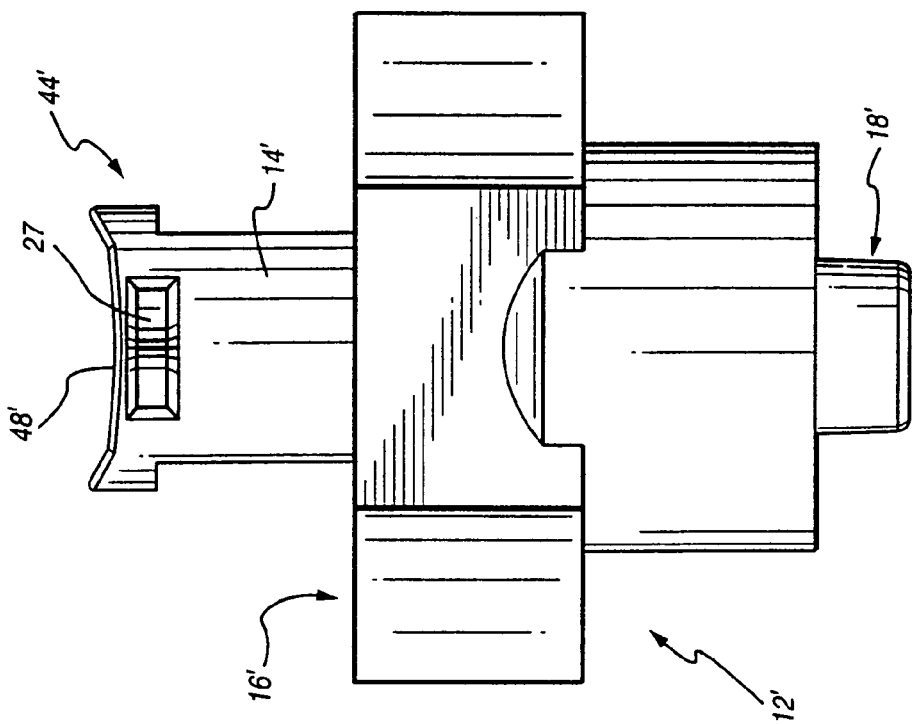

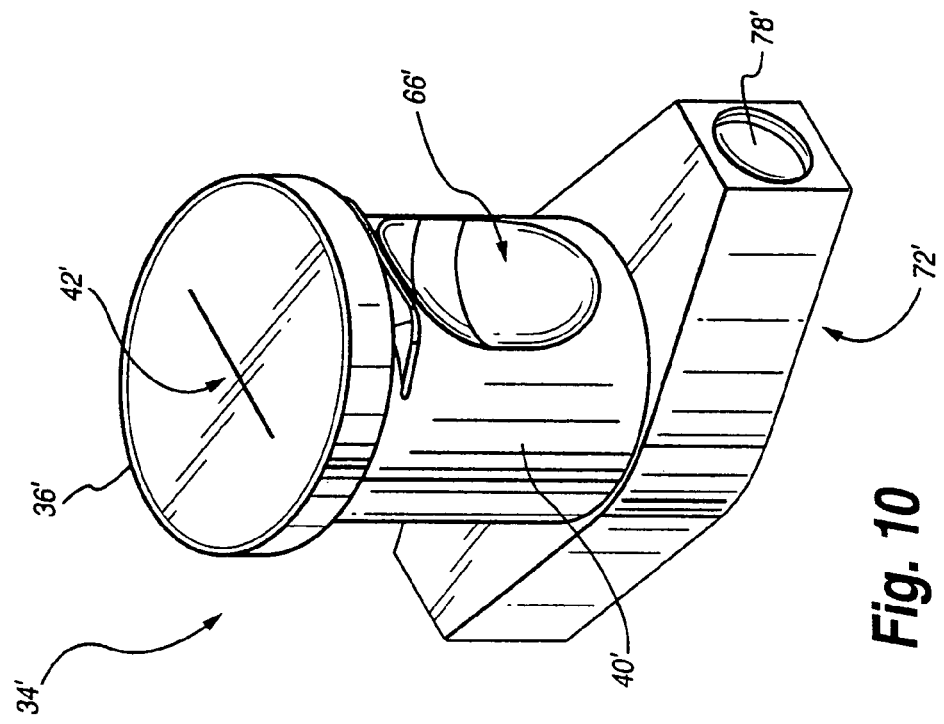
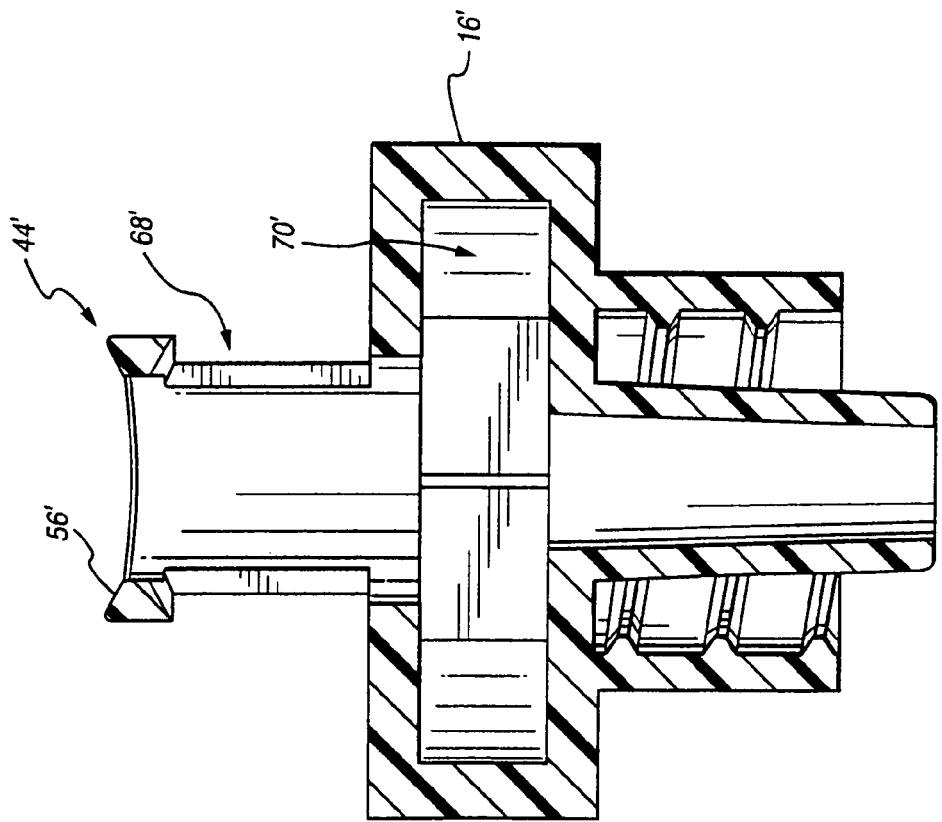

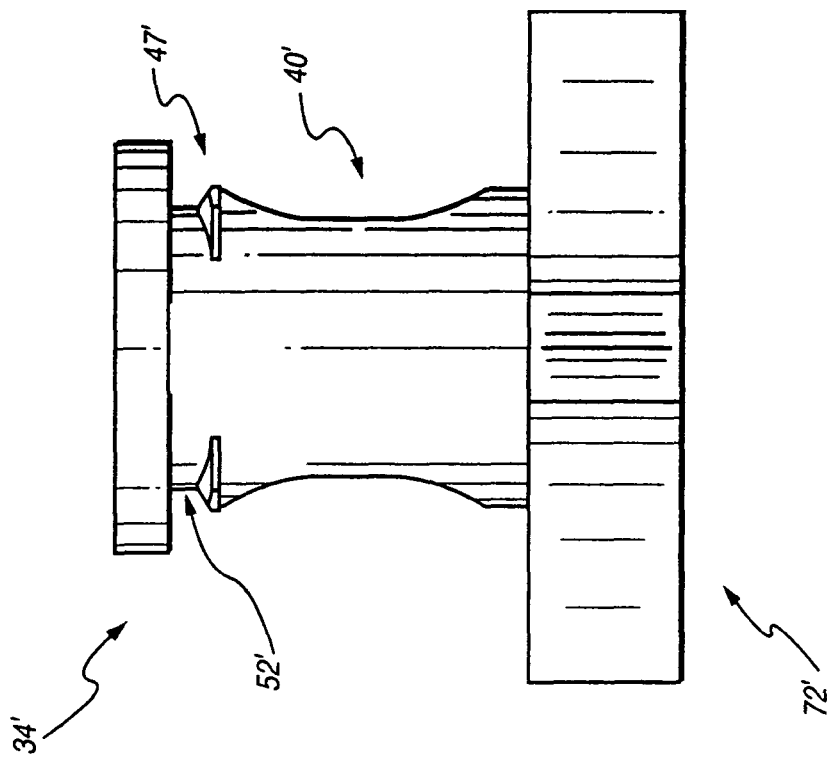
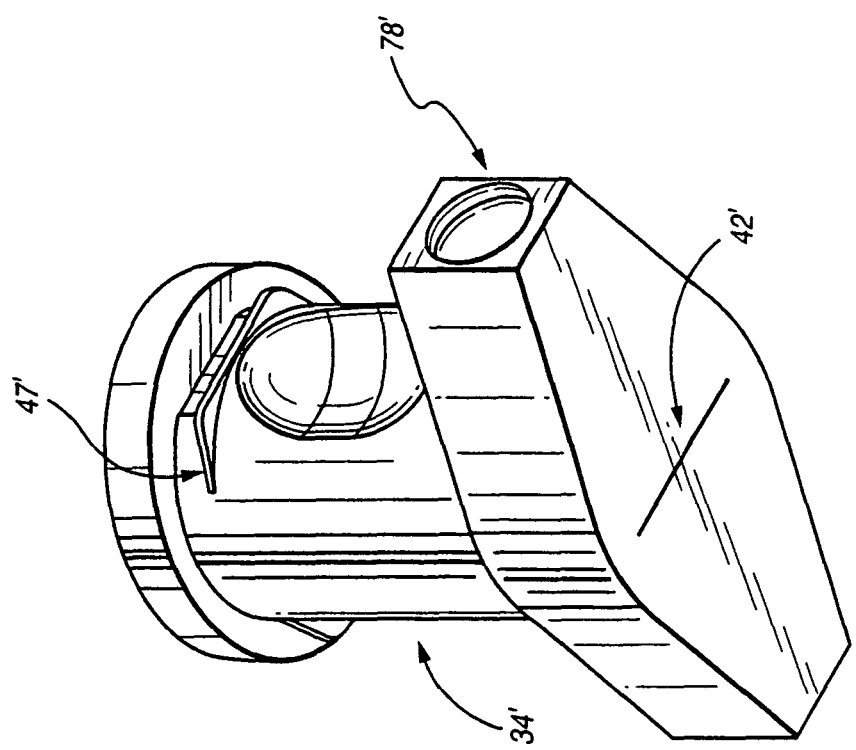

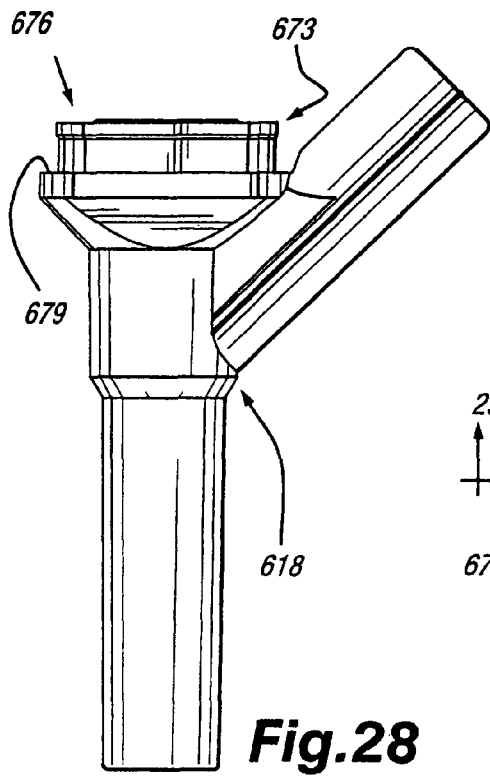
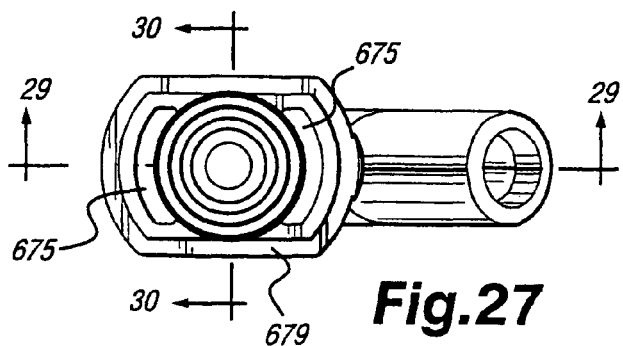
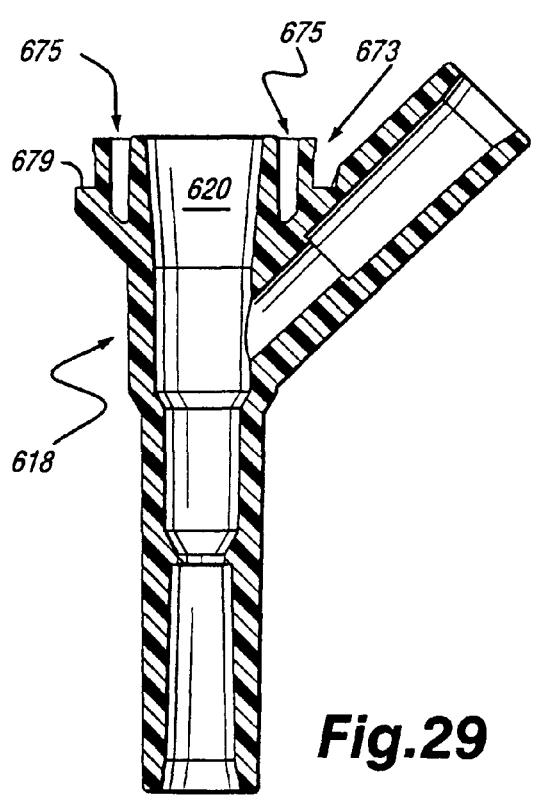
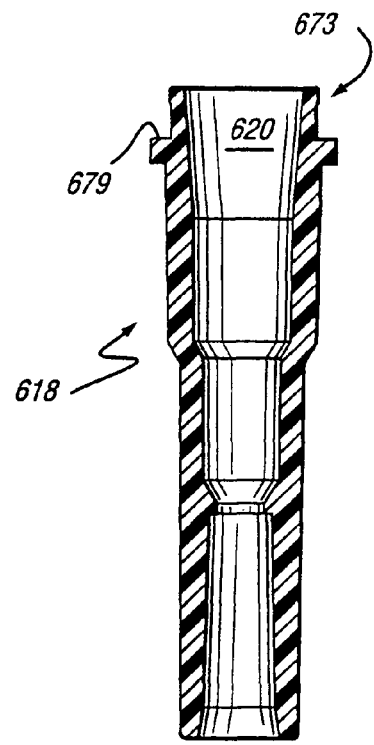
Fig.28
Fig.27
Fig.29
Fig.30

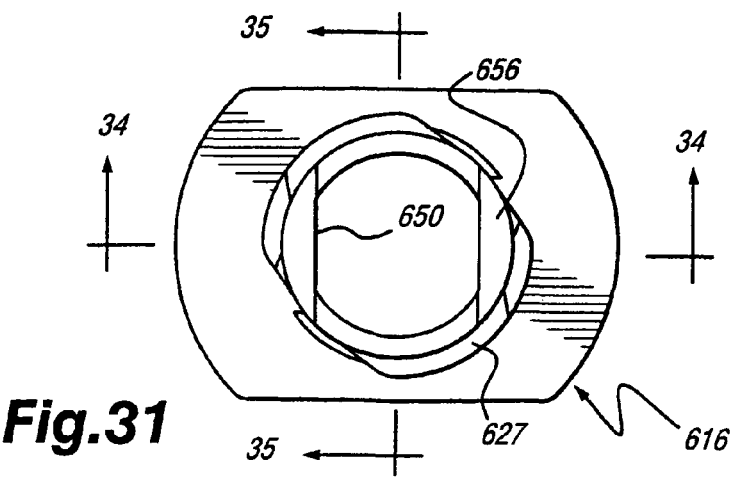
Fig.31
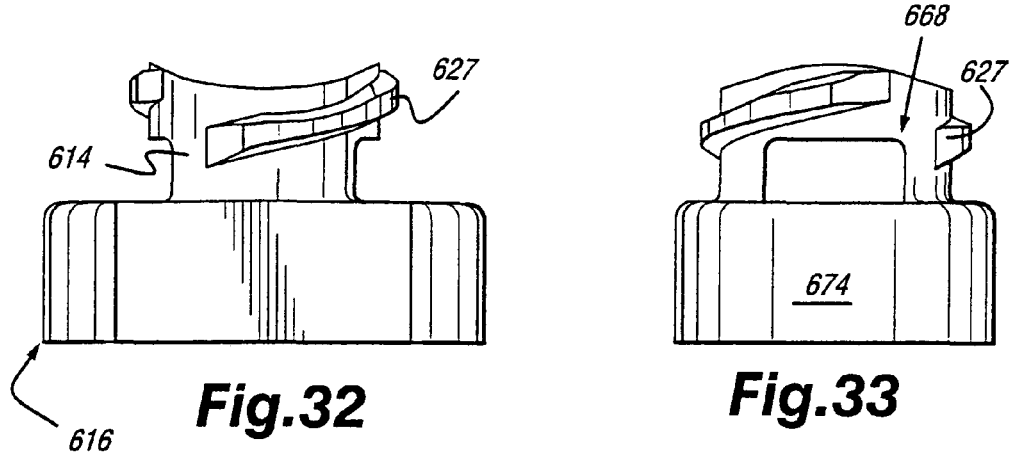
Fig.32  Fig.33
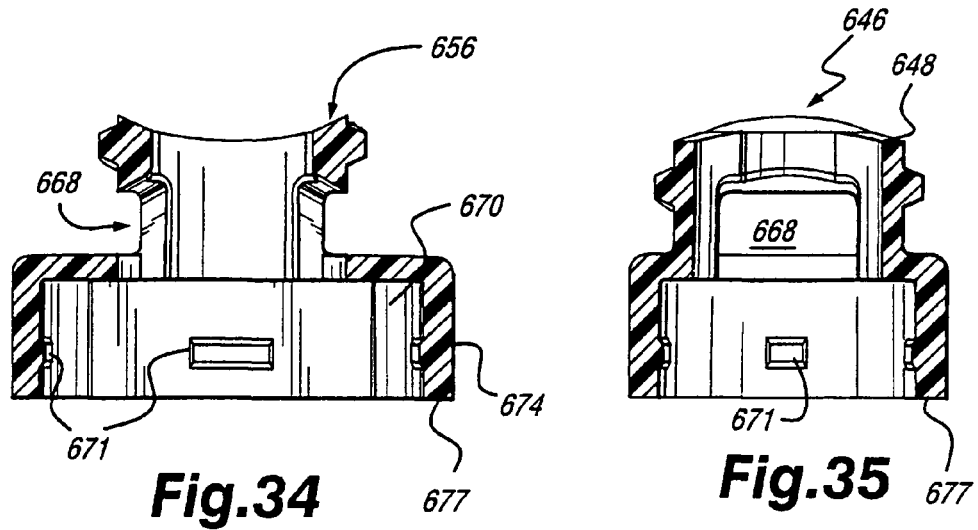
Fig.34  Fig.35

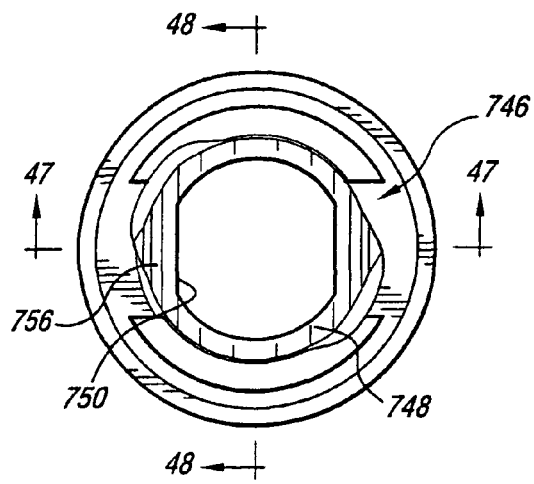
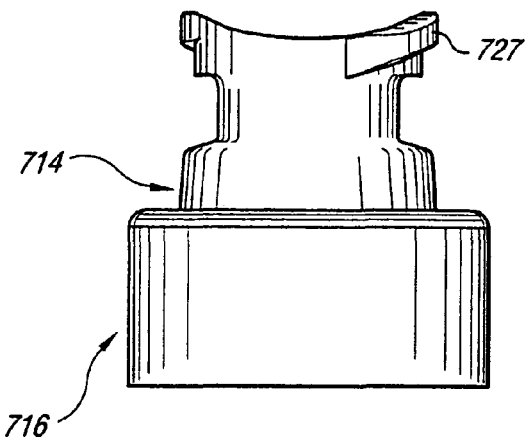
Fig. 44
Fig. 45
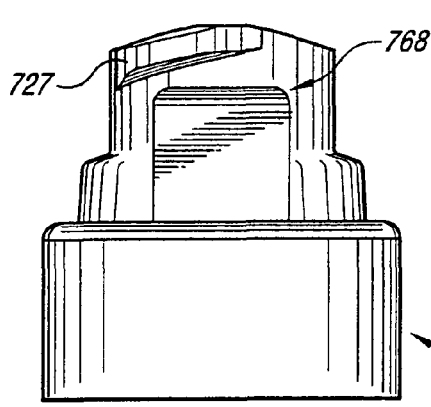
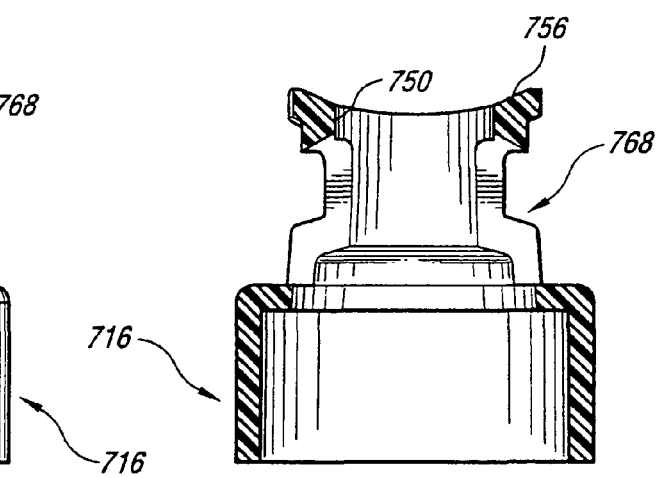
Fig. 46
Fig. 47
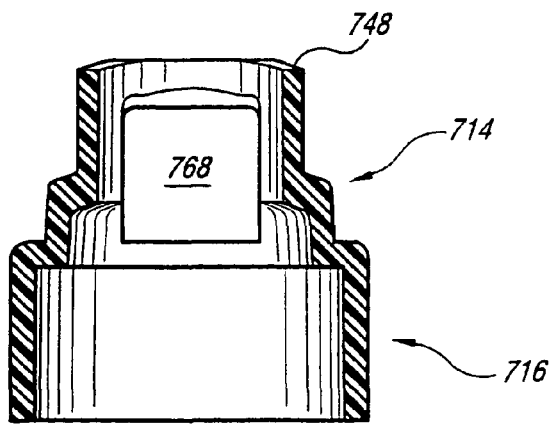
Fig. 48

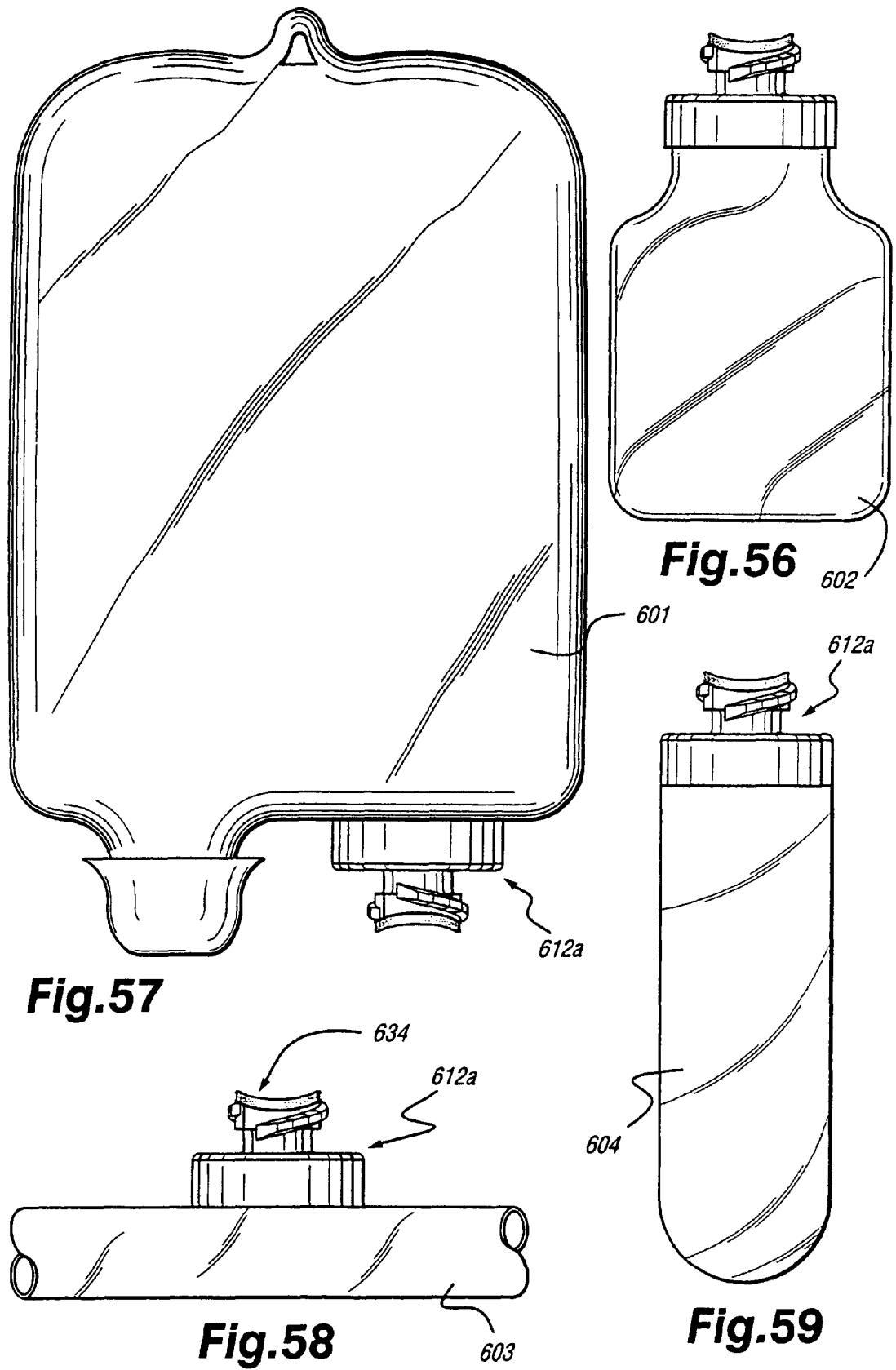

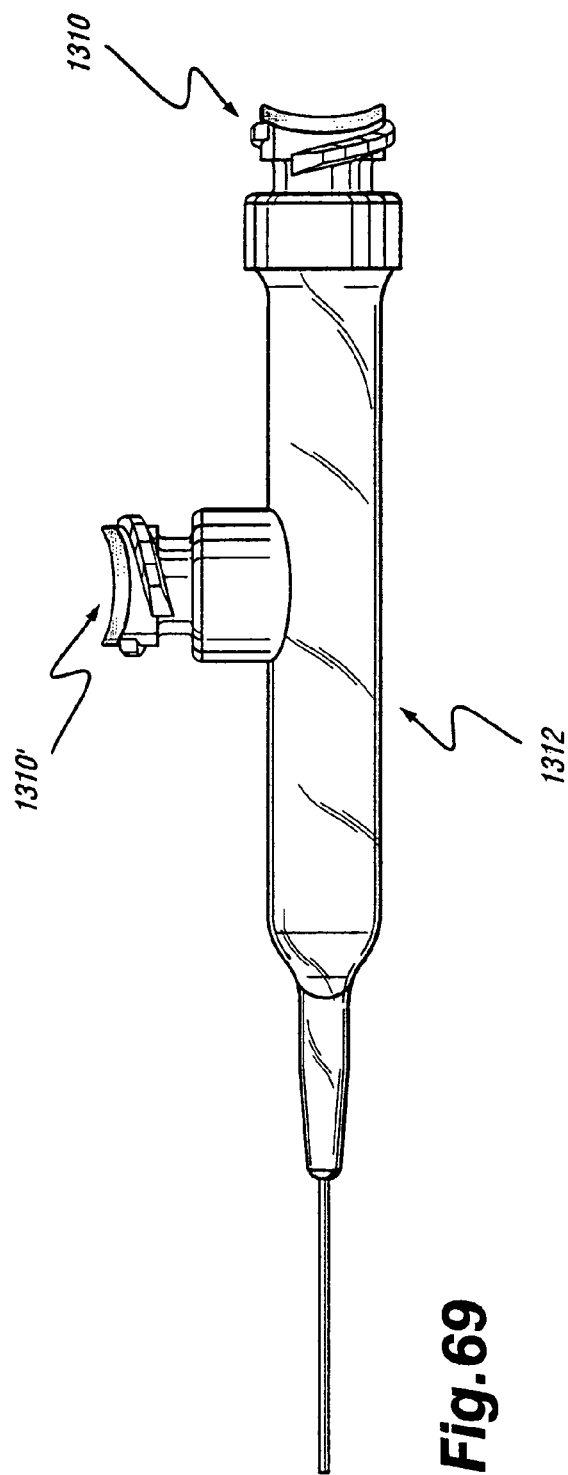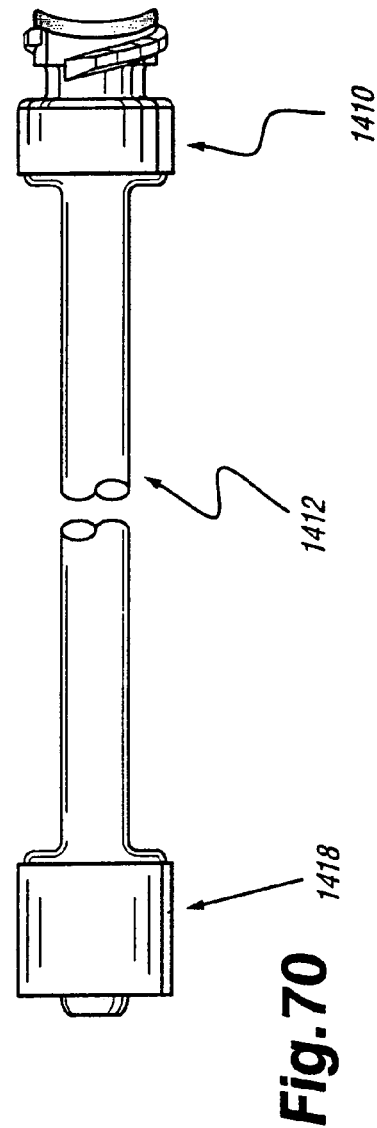
Fig.69
Fig.70

LUER RECEIVER AND METHOD FOR FLUID TRANSFER

This application is a continuation of U.S. patent application Ser. No. 09/635,153, filed Aug. 8, 2000, which is a continuation-in-part of U.S. patent application Ser. No. 09/322,037 (now U.S. Pat. No. 6,171,287), filed May 28, 1999, which claims the benefit of U.S. Provisional Application Ser. No. 60/087,162, filed May 29, 1998, and U.S. Provisional Application Ser. No. 60/101,998, filed Sep. 28, 1998, the entire disclosures of all four of which are incorporated herein by this reference.

BACKGROUND AND SUMMARY OF THE INVENTION

This invention relates to luer access devices for the engagement of conventional luer lock connectors and particularly to systems using penetration of a luer tip of a luer lock connector into a septum to achieve access for medical fluid transfer.

The high cost of the nascent "needle free" medical fluid access systems is well known. Much of this cost is related to the widespread use of cannulae for penetration of septa or to the use of expensive luer activation valves and internal spike based systems.

The ideal medical fluid access device must be applicable to all medical fluid delivery or blood access systems including IV lines, saline wells, arterial lines, hemodialysis lines, and any other site wherein fluid access for blood withdrawal or drug and fluid injection is desired and must have the following nine important characteristics:

1. Backward compatibility with conventional blunt cannulae.
2. Absence of flow limitation below the rate of flow through the luer cannula.
3. Absence of substantive negative pressure upon withdrawal of the luer lock connector from the device.
4. Low force of insertion of the luer tip into the device.
5. Absence of substantive kickback after luer tip slip insertion so that a luer tip will remain in a resting advanced position after insertion.
6. Small footprint and low profile (as is associated with conventional simple reseals).
7. Isolation of fluid flow to the central flow path within the device.
8. The basic design must provide a configuration which can be deployed without fluid dead-space in connection with the fluid interface. (Dead-space, such as that associated with the fixed lumen of central spike, will leave residual blood in the device if it is used for blood withdrawal).
9. Manufacturing cost similar to conventional standard reseals. (These simple devices were the basic access sites for fluid access for over 2 decades and constitute the cost basis for the optimal target manufacturing cost of any new system which aspires to become the new universal standard.)

It is an object of the present invention to provide a medical fluid access device, which can provide all of these nine characteristics and which can become the new universal standard for medical fluid access.

U.S. Pat. No. 5,466,219 (the disclosure of which is incorporated by reference as if completely disclosed herein) provides background for the present invention and discloses a septum with a central slit having a low penetration resistance adjacent an upper septum portion and tight sealing adjacent a lower septum portion. This type of septum design allows penetration by a large diameter cannula, such as a luer tip, to be achieved with an acceptable penetration force at the atmospheric interface while providing tight sealing in a lower portion of the septum. U.S. Pat. No. 5,474,544 (the disclosure of which is incorporated by reference as if completely disclosed herein) also provides background for the present invention and discloses a luer penetration receiving septum which eliminates the need for cannulae and needles. This invention discloses an elongated solid septum with a central slit. The septum includes a solid centrally slitted portion projecting centrally within the housing. This portion has a reduced transverse dimension lateral to the long transverse axis of the slit which effectively reduces the lateral deflection diameter of the septum after a luer tip has been received into a central slit so that the septum and housing and the penetrating luer taper can be contained within the confines of a cylindrical luer lock connector. The preferred embodiment includes slots in alignment with the long transverse axis of the slit to receive a portion of the laterally displaced septum volume on penetration by the luer tip. The use of properly positioned slots allows the lower portion of the septum to have sufficient mass lateral to the slit to reliably rebound to its resting shape thereby rapidly closing the slit when the luer tapered cannula has been withdrawn.

Referring to FIG. 18, there is schematically shown therein a structure 2010 that corresponds to a mock-up prop device that was made for showing the concept of the invention of U.S. Pat. No. 5,474,544. That device was formed by drilling out lateral portions of the septum 2034 to define cavities 2068 for receiving displaced septum portion(s) resulting from insertion of a male luer into the septum 2034. More particularly, to form a luer receiver having a septum with an extension of reduced width, a commercially available injection site for receiving a narrow blunt cannula was drilled out from each side with a thin circular grinding wheel oriented in parallel to the slit and coming in through the housing 2012, perpendicular to the slit to form cavities 2068 for receiving displaced septum portions when a male luer is inserted into the septum 2034. It is evident that to ensure a patent fluid passage to the patient, in a commercial form the septum would be performed to have the desired extension and the housing walls would not be drilled through, e.g. the cavities 2068 would be defined entirely by the reduced thickness of the septum extension 2040, or cutouts in the housing wall would not extend entirely therethrough. In this structure, the septum 2034 was fully received within the housing 2012 and cavities 2068 are defined lateral to the septum extension 2040.

The present invention includes an improved septum and housing configuration which is inexpensive to manufacture and which provides features increasing the rebound to the resting "closed slit" position thereby reducing the potential for leakage when used in situations of high pressure, such as arterial lines or hemodialysis lines. The present invention also provides a configuration which is associated with a reduced penetration force requirement for penetration of the septum, even with a flat faced large diameter luer tip, and which reduces or eliminates the negative pressure associated with luer tip withdrawal.

Generally the luer penetration receiver comprises a housing having an inlet and an outlet. The housing includes a proximal portion sized to be received and threaded into the conventional cylindrical luer lock end. An elongated elastomeric septum defining a longitudinal axis is provided having a sealing portion within the housing. The septum includes a target portion comprising an upper septum portion and a lower septum portion. The upper portion preferably projects above the housing and defines an atmospheric face. The lower portion is positioned adjacent the housing inlet. A slit extends through the septum from the sealing portion to the atmospheric face. The slit defines a longitudinal axis along the longitudinal axis of the septum and a long transverse axis along the transverse axis of the septum. The septum can include opposing lateral slits or grooves which separate the upper portion from the lower portion. The septum can further include an extension which projects centrally within the housing and has a reduced transverse width perpendicular to the long transverse axis of the slit when compared to the upper portion.

The septum preferably occludes the housing inlet. The upper portion of the septum preferably has a cross-sectional area greater than the cross-sectional area of the luer tip. The inlet is configured to provide opposing inlet wall platforms positioned below the upper septum portion. (The platforms can also extend around the septum to be circumferential). The septum upper portion preferably rests on the upper surface of the inlet wall platforms. At least a portion of the opposing platforms are positioned below opposing lateral portions of the upper portion of the septum lateral to and in relative alignment with the long transverse axis of the slit. The platforms preferably include opposing projections, which project into the opposing slits in the lateral wall of the septum. The opposing projections within the opposing slits preferably have upwardly sloping surfaces and the surface is highest adjacent the lateral edge of the septum to lever the opposing portions of the lateral septum portions upwardly with the leverage force being directed toward and along the long transverse axis of the slit thereby providing rapid resealing of the slit upon withdrawal of the luer tip from the slit. In association with the wedge effect of the sloping surfaces below the upper septum portion, the advancement of the tip against the central portion of the septum face induces relative upward deflection of the lateral portions of the septum by tipping the lateral walls upward as the central portion of the face deflects downward. In the preferred embodiment, the inlet wall platform is circumferential and extends from a low position of opposing wall troughs adjacent and perpendicular to the ends of the central slit, to a high position defining opposing wall peaks extending along an axis in relative alignment with the long transverse axis of the slit. This septum and inlet configuration facilitates penetration by the large diameter luer tip by allowing modest central downward deflection while tipping opposing lateral portions of the face upward thereby inducing a "facial valley" with laterally opposing upwardly sloping septum portions of the face aligned with the central slit. This induced configuration focuses the insertion force to wedge open the slit in opposing vectors perpendicular to the slit. Further, the upward deflection of the opposing lateral portions of the septum effectively reduces the lateral cross-sectional area of the upper septum portion at the atmospheric face thereby facilitating capture of the septum by the surrounding luer lock housing during penetration. Upon withdrawal of the luer tip, the leverage force discussed supra causes the slit at the atmospheric face to be forcibly closed. An important and unexpected benefit of using focused levered upward lateral deflection to seal the uppermost portion of the slit is that this configuration places the seal in a mechanically receptive position to be easily penetrated by even a flat large diameter luer tip. In addition, this configuration allows the resting concavity at the face to be minimized. If preferred, the upper portion of the septum can be molded in a "mushroom" configuration with the lateral walls thereof sloping downward and the undersurfaces of those lateral walls sloped downwardly, and the septum subsequently slit in this configuration. With this configuration upward deflection of the lateral walls can be induced by lateral portions of the housing that are not elevated and in fact could have a horizontal or even slightly laterally downwardly sloping configuration provided the downward slope is less than the downward slope of the undersurfaces of the lateral walls of the upper portion of the septum. This configuration will induce wedge compression at the slit adjacent the surface of the septum without a significant facial valley.

To provide additional sealing, the septum can have a region of focused compression of a short segment of the slit below and adjacent to the upper portion of the septum and preferably immediately adjacent the portion of the slit sealed by the leverage inducing platforms described supra. A second region of focused compression can be provided adjacent the extension or adjacent a distal end of the septum. The septum can include a lower portion mounted between the opposing platform projections which are aligned with the long transverse axis of the slit and which can project into the corresponding matching grooves in the lateral wall of the septum (which can be the same lateral grooves noted above which separate the upper and lower housing portions). The septum has a lateral transverse dimension intermediate the projections slightly greater than the corresponding internal dimension intermediate the opposing projections between which the septum is positioned. The septum is thereby slightly compressed transversely along a short longitudinal segment of the slit by the opposing projections perpendicular to the slit. This compression can be focused along a short segment of the slit by configuring the projections to have a narrow projecting vertical dimension at the projection ends such as is provided by a relatively pointed end. As described for the upper face, the upper surface of the platform projections are sloped to facilitate vertical deflection or expansion of the septum during insertion of the luer tip. This can also be provided for the lower surface of the projection. This is beneficial because the cylindrical luer lock connector is severely constraining relative to the potential space available for lateral deflection and any vertically deflected volume (especially upward and away from the housing inlet) can reduce the width of the lateral space required. While the focused compression induces resistance to penetration by the luer tip, this resistance can be easily overcome because of the matched shape of the projections and septum allows for expansion around (above and below) the projections into septum expansion receivers such as horizontal slots. A region of reduced resistance to the upwardly wedging force along the septum, such as is provided by extending the opposing lateral slits, intermediate the projections can be provided. The extended lateral slits and the focused compression just below the point wherein the central slit is levered closed allows the upper portion to be wedged upward without pulling open the central slit below the wedge.

When the luer tip is pushed against a septum face with the aforementioned configuration, a facial valley develops, easy penetration occurs, and, upon penetration, the opposing upper portions of the septum lateral to the long transverse axis slit are displaced laterally. To be useful as a luer lock receiver, it is very important to note that despite the receipt of the large diameter luer tip, the extent of lateral expansion of the septum must be contained within a minimal space so that the luer penetration receiver can be threaded into the limited confines of the cylindrical luer lock connector. This is true for both the septum portion contained within the housing and any septum portion above the housing. Also despite the tight space limitations and the need for tight sealing of the slit, lateral expansion of the slit by the luer tip must not be greatly inhibited so as to minimize the force of luer tip penetration into the septum. In the present invention, the housing and the septum are configured to present to each other a reduced vertical cross-sectional surface area for compressive contact between the housing and the septum during lateral septum expansion. This reduces the magnitude of the penetration force required to achieve lateral expansion of the septum thereby minimizing the penetration force. Using narrow opposing platform projections of the inlet wall can minimize this vertical cross-sectional area and facilitate expansion into an associated slot inferior or superior to the projection. By positioning the housing inlet adjacent the upper portion of the septum and by eliminating or reducing any housing structure lateral to the outer wall of the septum upper portion, the functional equivalent of a circumferential slot is achieved for the septum upper portion, allowing ease of lateral displacement of the septum upper portion above the inlet platforms. Alternatively, slots, or cutouts interposed between narrow vertically oriented posts may be used either lateral to the septum upper portion and/or lateral to the septum lower portion. This configuration allows much of the laterally expanded septum mass to be displaced around (above, below, or between) the posts rather than being compressed against it.

As noted previously, the septum further can include an extension having a smaller cross-sectional area than the upper portion projecting centrally within the housing proximal portion to the septum target portion. The slit extends centrally through the septum extension. Providing a slot or a cutout of the lateral wall of the septum extension can provide the smaller cross-sectional area of the extension of the septum. These slots or cutouts can be positioned in parallel alignment with the long transverse axis of the slit between the surrounding housing and the lateral wall of the septum extension. The septum slot or cutout provides room for the expansion of the septum within the confines of the proximal portion of the housing.

In one presently preferred embodiment, the septum further defines an enlarged enhanced sealing region adjacent the distal end of the septum. The slit of this sealing portion is tightly sealed. This may be achieved by a compression seal (of the type disclosed in U.S. Pat. No. 5,466,219). Alternatively, another enhanced sealing configuration may be used. If the compression seal is used, the sealing portion preferably has a greater cross-sectional area lateral to the slit than either the lower portion or the upper portion. The larger area provides room for ease of lateral septum displacement despite compression over a longer length of the slit. Since the enhanced sealing portion may be positioned slightly distal to the maximum intussuseption length of the cylindrical luer lock connector, an improved seal can be provided in this portion by a longer compression seal along the slit since it is not necessary to tightly constrain or minimize the vertical compressive interaction between the housing and septum in the manner discussed supra for the upper, the lower, and the extension portions of the septum. Alternatively, another short focused region of septum compression can be provided along the housing or a septum sealing portion such as a duckbill portion (of the type disclosed in U.S. Pat. No. 5,474,544) may be used.

It is an object and purpose of the present invention to provide an inexpensive, improved luer lock receiving septum having a configuration which provides rapid and tight resealing and yet allows penetration of the septum by the luer tip with a low penetration force.

It is yet a further object of the present invention to provide a deflection inducing member to provide opposing upward deflection of a septum portion to lever closed a slit at the face of the septum.

It is also an object of the present invention to provide a septum face having a minimum effective diameter during luer penetration while providing a maximum diameter of the initial target for luer tip advancement.

Another object the present invention is to provide an elongated septum having a central slit which includes an upper target face of enlarged diameter wherein the septum includes a central lower septum extension projecting about the slit below the inlet and into a housing so that the narrow extension can be more easily penetrated by entry into the narrow extension through the larger face and further so that there is provided sufficient room for both the laterally displaced extension of the septum, the luer taper, and the housing to be received into a conventional luer lock connector.

It is a further object of the present invention to minimize or eliminate the negative pressure deflection normally associated with the withdrawal of the large diameter luer cannula from an enclosed fluid filled lumen by providing isolation from the portion receiving the luer cannula by a distal sealing portion or by providing a septum extension around the slit which functions as a resting fluid displacement member and which inhibits fluid from entering the insertion zone after withdrawal of the luer cannula.

It is further the purpose of the present invention to provide a face, which is comprised of a homogeneous elastomer, which can be comprehensively wiped. (This is similar to the conventional simple reseal used in medicine for decades) The present invention has no open crevices or inaccessible spaces, which have contiguity with the luer, access face, or slit, or fluid path. There is no circumferential piston-to-cylinder space or crevice at the luer contact face of the valve as is associated with the conventional luer access valves in wide use. This space has the greatest potential for colonization. It comprises a circumferential crevice, which is in direct contact with the septum face and it contacts the end of the luer tip and is in direct contiguity with the fluid path. Drops of fluid at the septum outer face will contact both the circumferential crevice and the slit so that contamination contiguity from a microbiologic perspective is operative with the first activation and at any time during subsequent use. Bacteria and fluid gaining entry into the circumferential crevice are displaced back and forth and are not accessible to wiping. Parenteral nutrition fluid gaining entry to the crevice provides a perfect culture medium for rapid bacteria growth. This growth is inaccessible to wiping and is pistoned back and forth in direct contact with fluid droplets on the outer face and the slit itself for potential entry into the patient's blood stream.

It is further the purpose of the present invention to provide a long slit, which provides for a secure seal of the fluid path to reduce the potential for bacterial egress.

It is further the purpose of the present invention to provide a high surface sealing force as by compressive sealing which is applied and focused directly at the surface by the lever action on the upper septum portion. This allows maximum tight sealing exactly at the surface interface with the surrounding environment so tiny open crevices do not form at the surface exit point of the slit. This helps to prevent the egress of droplet contamination at the surface of the slit. This is advantageous over transverse compression alone since a central slit will not lever closed as tightly directly at the surface by transverse compression applied below the upper surface of the septum. Indeed if the surface is induced into a convex configuration by transverse compression then there can be a tendency for slight gapping of the slit at the surface.

It is further the purpose of the present invention to provide a septum with relatively high mass so that the slit is more securely and more robustly sealed in a range of usage situations.

It is further the purpose of the present invention to provide a simple configuration having only a septum and outer housing, and wherein there are no internal parts in contiguity with the fluid path.

It is further the purpose of the present invention to provide a wiping action of the long septum on the luer tip, which wiping action can be exploited further by adding an antimicrobial agent to the elastomer as discussed below.

It is further the purpose of the present invention to provide a design wherein the entire contact between the luer tip and the valve is with the elastomer.

It is further the purpose of the present invention to provide an antimicrobial barrier associated with the elastomer such an antimicrobial coating of the elastomer (as is known in the art) or as by molding the septum from an antimicrobial elastomer (such antimicrobial elastomers are known in the art). This assures that a comprehensive barrier is provided at all surfaces potentially contacting the luer tip during insertion. Since the luer tip contacts only the elastomer during and after insertion, there is no need to coat or otherwise apply antimicrobial to or within the housing structure although it may be applied if desired.

It is further the purpose of the present invention to provide a distal seal in combination with a long slit which therefore allows a syringe attached to a luer tip extending through the septum to be decompressed upon partial withdrawal within the septum to avoid blood spurting during blood sampling. (The background of the prevention of blood spurting during pressurized blood sampling can be reviewed in U.S. Pat. No. 5,114,400, the disclosure of which is incorporated by reference as if completely disclosed herein).

This invention also relates to medical containers including drug vials, and blood collection containers. There has been a longstanding need for luer access containers which can be manufactured at a very low cost, which provide a strong bi-directional seal during and after luer penetration, which are comprised of conventional materials for which drug compatibility has been already established, and which do not require the addition of an internal spike for penetration of the stopper, which by its nature adds complexity and cost. Also such internal spikes remain in contact with the drug once the initial activation has been performed so that issues of compatibility and the internal spike arise if the drug vial is intended for multiple access over several days as with many conventional drug vials.

The present invention comprises a container such as a drug vial including an open end sealed by a stopper. The stopper is preferably comprised of a medical grade conventional elastomer such natural rubber, for example. Alternatively, and especially for use in evacuated containers, a medical grade silicone or polyisoprene may be used, and may have a hardness of 30-40 Shore A, for example. The stopper is held in place by a stopper retainer which, for containers which serve as drug vials, is preferably comprised of metal crimp retainer. Alternatively, a rigid plastic retainer such as polycarbonate may be used. In the preferred embodiment, the retainer includes a portion for attachment about the open end of the container although the retainer may be integral with the container open end. The stopper is mounted with the retainer such that the retainer and stopper present a upper elastomeric portion having a target elastomeric face for engagement with the luer tip and further to present a rigid surrounding portion about the face which is sized and configured to receive the threads of the luer lock connector.

The stopper preferably includes a pre-slitted portion and may be slitted from both the upper surface and the lower surface, the slits preferably do not extend completely through the stopper so that a complete seal is provided for long term storage. The upper and lower slit may be formed by slitting, and may be slitted using the "anvil and blade method", as is known in the art, to stretch and induce a very thin membrane. Alternatively the slits may be molded, as by the providing of a projecting fine metal leaf into the stopper during molding, as is known in the art. In one preferred embodiment, the first portion of the upper slit is molded and then the lower slit is extended by inserting an anvil into the upper slit and then further slitting the lower portion using a blade to a predetermined point adjacent the upper face. In one embodiment, the lower slit is pre-molded and the anvil is sized with the approximate diameter of a luer cannula and can be inserted into the face opposite the lower slit, achieving precise and focused stretching of the membrane before the blade is advanced to extend the lower slit to further thin and weaken the membrane. Alternatively, both the upper and lower slits can be pre-molded and either the upper slit or lower slit then extended by the insertion of a luer diameter anvil into the opposing slit to stretch the membrane over the anvil and then applying a blade to further thin the membrane.

If the slits are molded, the stopper can be subsequently placed with the retainer and/or open container end in a slight state of compression so as to seal the molded slit. The upper and lower slits may be formed so that an obliquely oriented membrane separates them so that the upper slit ends adjacent an oblique membrane to facilitate more easy rupture by the advancing luer during operation. In one embodiment the membrane is positioned at a point wherein the luer tip forcefully engages only one portion of the membrane when the threads of the retainer have been well engaged with the luer lock threads so that the rupture of the membrane is facilitated by the mechanical advantage provided by the threading process against a narrow focused region of maximally stretched membrane.

In another embodiment a membrane-cutting cap is provided wherein a cutting member is provided within a cap member such as a luer cap. The cap includes a projecting membrane-cutting member such as a spike or narrow sharp edge blade to perforate the membrane prior to luer access. The cutting surface can be recessed within the cap so as to be inaccessible to human fingers.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which:

FIG. 2 is a top view of the septum of the luer penetration receiver of FIG. 1 without the housing;

FIG. 3 is a top view of the housing of the luer penetration receiver of FIG. 1 without the septum;

FIG. 5 is a side elevational view of the housing of FIG. 4;

FIG. 6 is an end elevational view of the housing of FIG. 4;

FIG. 9 is a cross-sectional view taken along line 9-9 of FIG. 7;

FIG. 10 is a perspective view from above of a variant of the septum of FIGS. 1 and 2;

FIG. 11 is a perspective view from below of the septum of FIG. 10;

FIG. 12 is a side elevational view of the septum of FIG. 10;

FIG. 27 is top plan view of the luer receiver Y-site housing base of the embodiment of FIG. 26;

FIG. 28 is side elevational view of the luer receiver Y-site housing base of the embodiment of FIG. 26;

FIG. 29 is a cross-sectional view taken along line 29-29 of FIG. 27;

FIG. 30 is a cross-sectional view taken along line 30-30 of FIG. 27;

FIG. 31 is top plan view of the luer receiver housing body of the embodiment of FIG. 26;

FIG. 32 is a side elevational view of the luer receiver housing body of the embodiment of FIG. 26;

FIG. 33 is an end elevational view of the luer receiver housing body of FIGS. 31 and 32;

FIG. 34 is a cross-sectional view taken along line 34-34 of FIG. 31;

FIG. 35 is a cross-sectional view taken along line 35-35 of FIG. 31;

FIG. 44 is top plan view of the luer receiver upper housing body of the embodiment of FIG. 43;

FIG. 45 is a side elevational view of the luer receiver housing body of FIG. 44;

FIG. 46 is another side elevational view of the luer receiver housing body of FIGS. 44 and 45;

FIG. 47 is a cross-sectional view taken along line 47-47 of FIG. 44;

FIG. 48 is a cross-sectional view taken along line 48-48 of FIG. 44;

FIG. 56 is an elevational view showing a housing body and septum in accordance with the invention mounted to a housing base defined by an drug vial, in accordance with another exemplary implementation of the invention;

FIG. 57 is an elevational view showing a housing body and septum in accordance with the invention mounted to a housing base defined by an intravenous fluid bag, in accordance with a further exemplary implementation of the invention;

FIG. 58 is an elevational view showing a housing body and septum in accordance with the invention mounted to a housing base comprising blood tubing access port, in accordance with yet a further exemplary implementation of the invention;

FIG. 59 is an elevational view showing a housing body and septum in accordance with the invention mounted to a housing base defined by vacuum blood or specimen collector, in accordance with yet another exemplary implementation of the invention;

FIG. 69 is an elevational view showing two luer receivers mounted to a housing base defined by an a catheter, in accordance with a further exemplary implementation of the invention;

FIG. 70 is an elevational view showing a housing body and septum in accordance with the invention mounted to an intravenous line, in accordance with a further exemplary implementation of the invention;

DESCRIPTION OF THE PRESENTLY PREFERRED EXEMPLARY EMBODIMENTS

Figure 1:
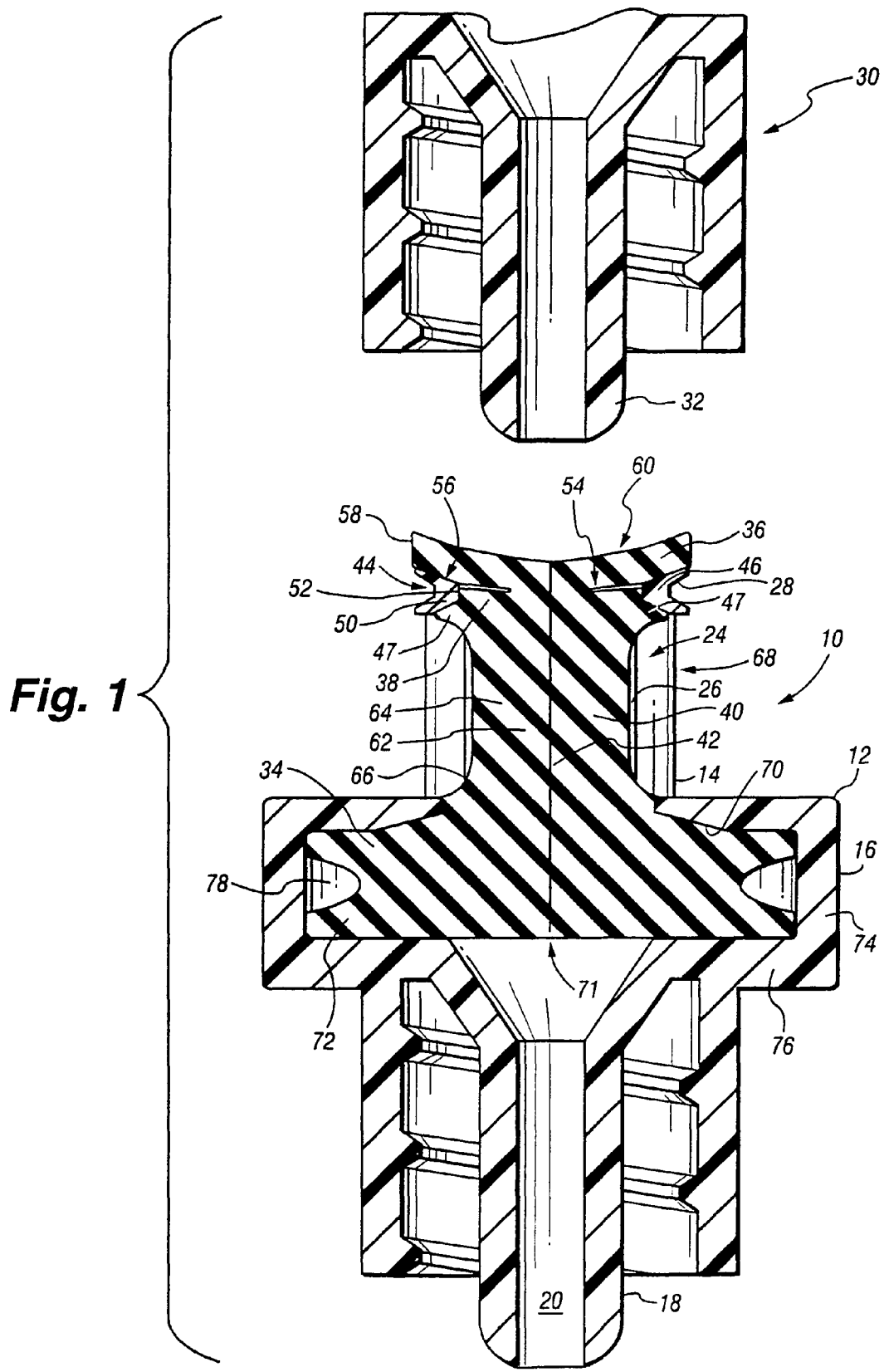
FIG. 1 is a longitudinal half-section of the luer penetration receiver of the present invention where the section is taken perpendicular to the central slit and wherein the receiver is rotated such that the wall slots are positioned to the right and left sides.

As shown in FIGS. 1, 2, and 3, the luer lock receiver 10 comprises a housing 12 including an proximal portion 14, a central portion 16, and a distal portion 18 having a distal lumen 20. The proximal portion 14 has an inlet 22, and interior walls 24 defining an intermediate space or bore 26 and outer threads 28 and is sized to be threadably received into a conventional luer lock 30 with male luer tip and a surrounding female threaded end. Bore 26 is sized to receive a conventional luer cannula 32. A septum 34 has a proximal portion that, in this embodiment, includes a widened upper portion 36 and a narrower lower portion 38. The septum 34 further has an extension 40 that is received intermediate the interior walls of the housing 12. A central slit 42, sized to snugly receive the luer cannula 32, is provided to extend from adjacent the upper face of the upper portion 36, through the proximal portion of septum 34 and at least partly through the extension 40. In the embodiment of FIG. 1 the slit extends through the extension 40 into a distal septum portion 72 (discussed below). However, as is also discussed herein below, the slit is preferably incomplete as shown at 71 to provide a hermetic seal prior to first penetration. The septum can be formed of polyisoprene, although other similar medical grade material may be used including silicone rubber. The preferred durometer falls within the range of conventional durometers of medical septae for IV and arterial line tubing reseals in wide use and employed for penetration by cannulae including blunt cannulae. One example of acceptable elastomeric septum material is the material which is used to form the blood access septa of the SAFESET™ arterial line marketed by Abbott Laboratories (List No. 42644-06). The septum elastomer durometer can, for example, be in the range of 30.

The housing inlet 22 includes an inlet wall platform or ring 44 defining platform elevations 46 positioned parallel to the long transverse axis of the slit 42. The upper surface of the platform 44 slopes upwardly from opposing trough portions 48 (FIG. 3). The trough portions 48 are positioned adjacent and aligned perpendicular to the ends of the slit 42 to create a low point of the housing inlet 22 adjacent the ends of the slit 42. The opposing platform elevations 46 can be configured and oriented such that they readily engage the internal threads of the connector 30 adjacent the highest point of the platform 44. The platform elevations include opposing internal projections 50 oriented to project toward the bore 26. The projections 50 are preferably narrow and can be tapered or pointed so the septum lower portion 38 can be easily compressed laterally against the narrow projections 50 and can be expanded around the projections 50 when the luer tip is advanced through the slit 42 (as will be described). The septum 34 has opposing grooves 52 to receive the projections 50. The lateral transverse dimension of the septum 34 intermediate the grooves 52 (and perpendicular to the slit 42) is slightly greater than the corresponding intermediate internal lateral dimension of opposing projections 50 so that the septum 34 is slightly compressed transversely by the opposing projections 50. When at rest, the septum lower portion 38 is preferentially not substantially compressed along an axis extending between trough portions 48 since this would potentially bias the slit toward the open position.

As shown in FIG. 1, a parallel slit 54 extending from grooves 52 of the lower septum portion intermediate the opposing projections 50 can be provided to further reduce the force required for expansion of the lower septum 38 and allow for enhancement of the upward wedged configuration to be described. A portion 47 of the lower septum 38 can expand into the slot 68 provided under the circumferential platform 44. Opposing angled upper surfaces 56 of the projections 50 are provided along the platform elevations 46. The angled upper surface 56 fit into lateral slits or grooves 52 and upwardly wedge the opposing lateral elevated septum portions 58 of septum upper portion 36 to define a curved face 60 with the central slit 42 aligned between elevated septum portions 58. The slit is positioned centrally and aligned with the longitudinal axis of the curved face 60. The central slit 42 is tightly closed by the levered force of the wedged elevated septum portions 58 which is focused upon the central slit 42.

The septum extension 40 has a transverse width and thus cross-sectional area smaller than the transverse width (and cross-sectional area) of upper portion 36. The extension 40 includes lateral walls 62 aligned with and adjacent the central slit 42. The extension 40 is positioned within bore 26 and includes a thinner portion 64 with a transverse width, and therefore cross-sectional area, smaller than the transverse width (and cross-sectional area) of the bore 26 to define opposing septum slots or cutouts 66 which are aligned with opposing wall cutouts 68 in the proximal housing 14. Where a threaded shroud 30 is to be received over and about housing 12, the volume of the cavity(ies) or voids defined by the combined volume of the cutouts 66, if any, and the cutouts or slots 68, if provided, is such that at least the volume of the portion of the septum 34 laterally displaced by insertion of the male luer tip can be accommodated, so that the septum and housing and the penetrating luer taper can be contained within the confines of a cylindrical luer lock connector.

The central housing portion 16 defines opposing lateral slots 70 for receiving an enlarged sealing septum portion 72.

The sealing septum portion 72 is compressed at an increased distance from the central slit 42 by opposing walls 74 transverse to the long transverse axis of the central slit 42 to enhance the sealing of the slit 42. The sealing septum portion 72 fits relatively flush against the wall 76 adjacent the slit 42 to minimize downward deflection associated with penetration of the sealing septum portion 72 into the lumen 20 to minimize the potential of negative pressure deflection within lumen 20 upon withdrawal of the luer cannula 32. Lateral deflection can be enhanced by reducing or eliminating the compression of the most distal segment of the sealing septum portion 72 immediately adjacent the lumen 20. Additional opposing cutouts 78 can be provided in the lateral portion of the sealing septum 72 to allow a portion of the septum extension 40 mass to more easily expand downward into the slots 70. The sealing septum portion 72 serves to isolate the proximal housing bore 26 which actually receives the greatest volume of the luer cannula 32 from the fluid filled distal lumen 20 to prevent the development of negative pressure within the lumen 20 upon withdrawal of the luer tip 32. The septum extension 40 isolates the slit 42 from the proximal housing bore 26 and serves to displace the fluid volume from this bore thereby also inhibiting flow into the bore 26 and the attendant negative pressure deflection even when an isolating distal sealing septum 72 is not provided.

In operation, the luer cannula 32 penetrates by entering at the curved face 60 and tips deflecting or lateral portions 58 of the upper septum portion 36 upward to be captured within the cylindrical luer lock connector 30. Further downward advancement of the luer cannula 32 also expands the lateral walls of the upper septum portion 36 to compress against the opposing narrow projections 50. This compression is focused by the opposing narrow projections 50 and can be overcome by the insertion of the luer tip because of the matched shape of the inlet platform 44 and septum 34 allows for expansion around (above and below) the inlet platform 44. Despite the focused compression force at this region, penetration is easily achieved through this region by the receptive configuration of the levered septum upper portion 36 and by expansion of the septum 34 around the narrowed projection 50 above and below the platform 44. As the luer cannula 32 advances further, the lateral walls 62 of the septum extension 40 are then deflected into the spaces provided by the septum cutouts and the housing slots. A portion of the septum extension 40 is also deflected into slot 70. As the luer cannula 32 is advanced distally through slit 42, it displaces the sealing septum portion 72 laterally to open fluid communication between the luer cannula 32 and the distal lumen 20.

The length of the proximal housing portion 14 is sized to allow the luer lock connector 30 to be fully threaded onto the proximal portion 14. In one embodiment the length of the septum is provided so that the luer taper tip upon maximum penetration reaches to a position within the slit 42 just proximal to the end of the sealing septum. The large relative diameter of the luer cannula 32 will hold a portion of the central slit 42 open beyond the tip of the cannula 32 so that precise positioning is less critical. This can be employed to further reduce the potential for the induction of negative fluid pressure deflection upon withdrawal of the luer tip.

The presently preferred width of the curved or atmospheric face 60 can be in the range of about 8 mm by 7 mm with the long axis extending along the long transverse axis of the central slit 42. The central slit 42 can have a length along its long transverse axis of about 3-5 mm. The lateral housing slots 68 can be about 7 mm wide by 4 mm in length. The platform upper surfaces 56 can be angled upward in the range of about 30-45 degrees. The lateral grooves 52 and extending lateral slit 54 in the lower septum portion can be about 2 mm-2.5 mm in depth (when measured at the point along face 60 of maximum depth of the grooves 52 and lateral slits 54). The septum 34 as mounted with the extension can be about 8-11 mm in length. The upper portion of the septum can be about 1-1.5 mm in thickness but may be extended to 2 mm if desired. The sealing portion can be in the range of 2-15 mm in length. Each of the lateral walls of the septum extension can be about 2.5-3 mm in width if opposing cutouts 68 through the proximal housing walls are provided. It should be clear that these dimensions represent only presently preferred dimension ranges and other ranges can be employed or may be learned by practice of the invention. Moreover, the extension cutouts could be more deeply concave in the transverse plane resulting in very thin lateral walls adjacent the central slit.

Referring again to FIG. 1, a simplified embodiment can be provided having the septum configuration of FIG. 1 with an upper portion 36 and a lower portion 38 but without an extension 40. The septum is sealed into the housing 14 along the ring 44. This configuration is particularly suited for use with a luer docking station or other simple luer lock receiving systems which do not require protection against leakage under very high internal pressure (although a means for enhanced sealing as adjacent ring 44 can be included if enhanced sealing is desired).

FIGS. 4-16 illustrate a modified version of the embodiment of FIGS. 1-3, in which corresponding structures are illustrated using the same reference numerals denoted with the prime symbol ('). In this version, the extension cutouts 66' are more deeply concave in the transverse plane resulting in thin lateral walls adjacent the central slit 42'. Furthermore, in this adaptation, rather than providing thread(s)/groove(s) 28, luer ears or projections 27 are defined on the exterior surface of the housing proximal portion 14' for engaging the luer threads of connector 30. Otherwise, the structure illustrated in FIGS. 4-16 generally corresponds to that shown in FIGS. 1-3. In particular, the housing 12' includes proximal portion 14', a central portion 16' having cutouts 68', and a distal portion 18'. In this example, cutouts 68' are defined entirely through the housing wall. The inlet end of the housing includes an inlet wall platform or ring 44' defining opposing trough portions 48' and platform elevations 46'. The platform elevations 46' include opposing internal projections 50'.

The septum 34' has a widened upper portion 36', an extension 40' and an enlarged distal sealing septum portion 72' including opposing cutouts 78' which allow a portion of the septum mass to more easily expand into housing slots 70'. FIGS. 10, 11,13 and 14 most clearly depict the deflection reservoirs or cutouts 78' provided in the distal septum portion 72'. As in the embodiment of FIG. 1, a slit 42' is defined longitudinally through the septum 34'. In this example, however, slit 42' is defined all the way through the septum 34', as can be seen from FIG. 11.

The septum 34' has opposing grooves 52' to receive projections 50'. Portions 47' of the septum 34' extend under projections 50' whereas opposing angled upper surfaces 56' of projections 50' fit into grooves 52' adjacent slits 54'. This wedges elevated septum portions 58' of upper septum portion 36' to define a curved face 60' with the central slit 42' aligned between septum portions 58'. As with the structure shown in FIG. 1, the central slit 42' is tightly closed by the levered force of the wedge septum portions 58', which is focused upon central slit 42'.

As will be recognized from a consideration of the luer receiver disclosed with reference to FIGS. 1-16, above, the luer receiver of the invention is intended and may be adapted for universal use. To that end, the luer receiver can be constructed as a two or more part housing, for example, a housing body and housing base that capture the septum therebetween. Alternatively, the septum may be inserted into an integral housing structure.

Figure 17:
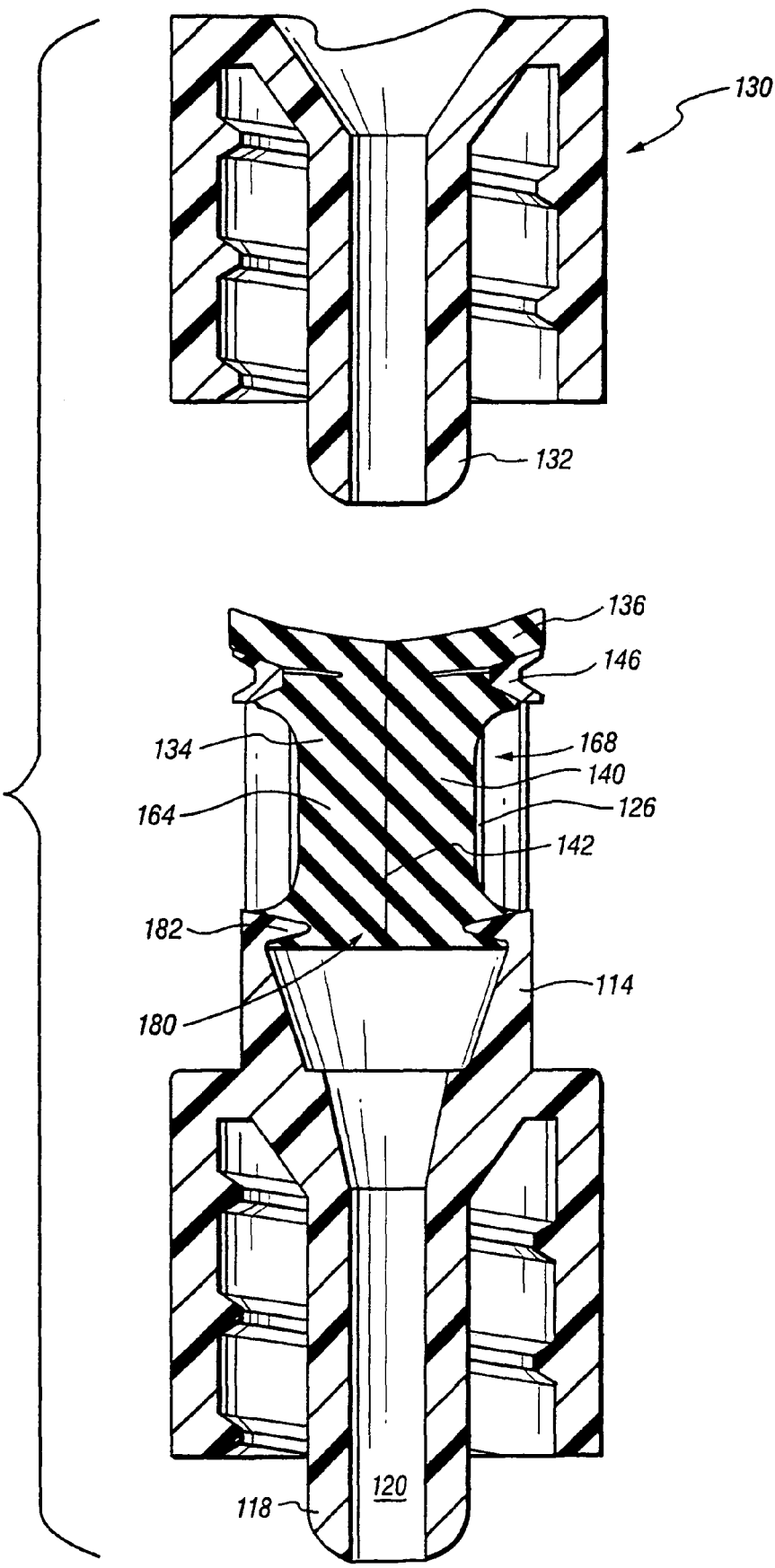
FIG. 17 is a longitudinal half-section of another embodiment of the present invention wherein the section is taken perpendicular to the central slit and wherein the receiver is rotated such that the wall slots are positioned to the right and left sides.
Figure 17A:
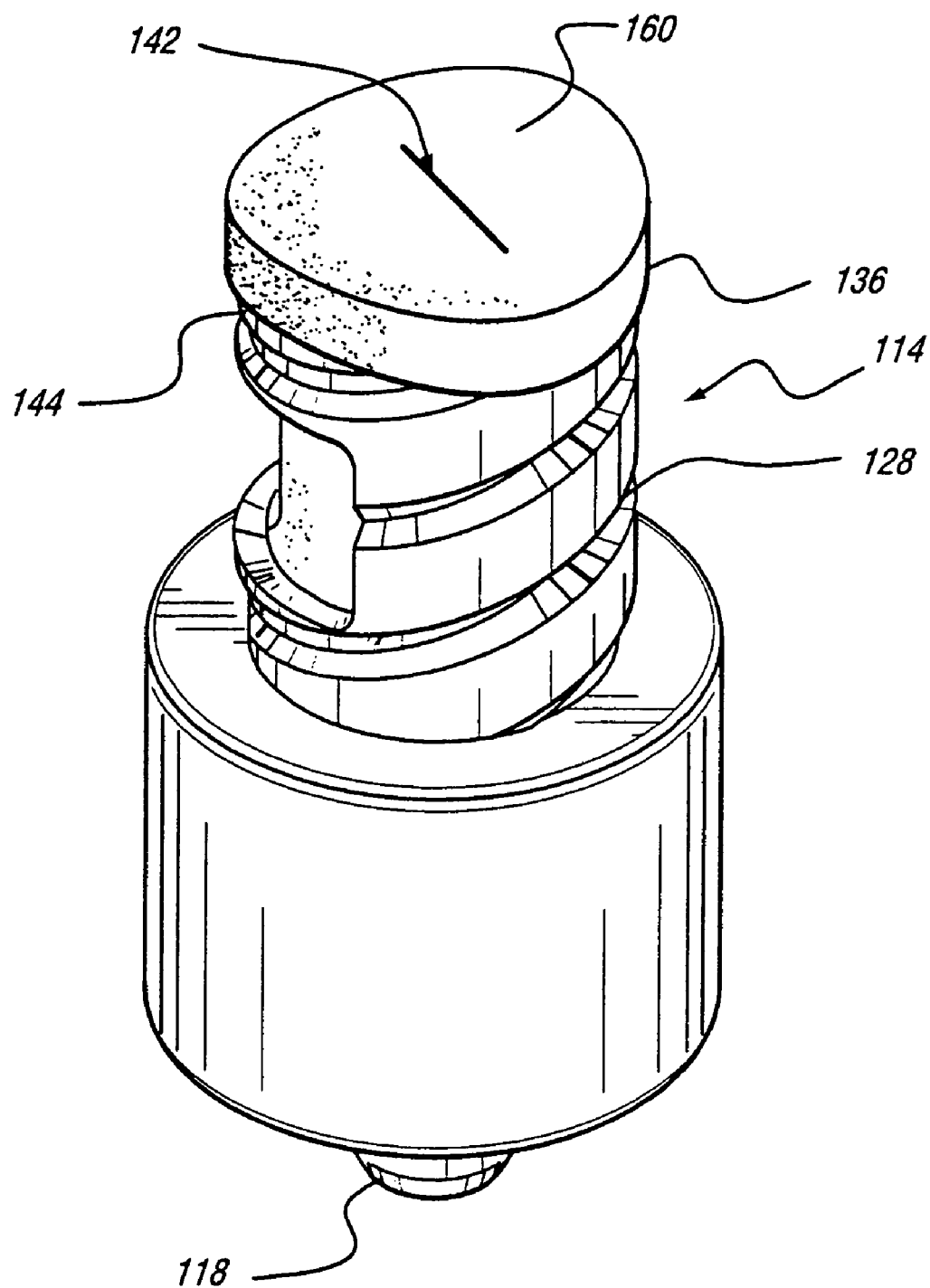
FIG. 17A is an isometric side view of the embodiment of FIG. 17.
Figure 18:
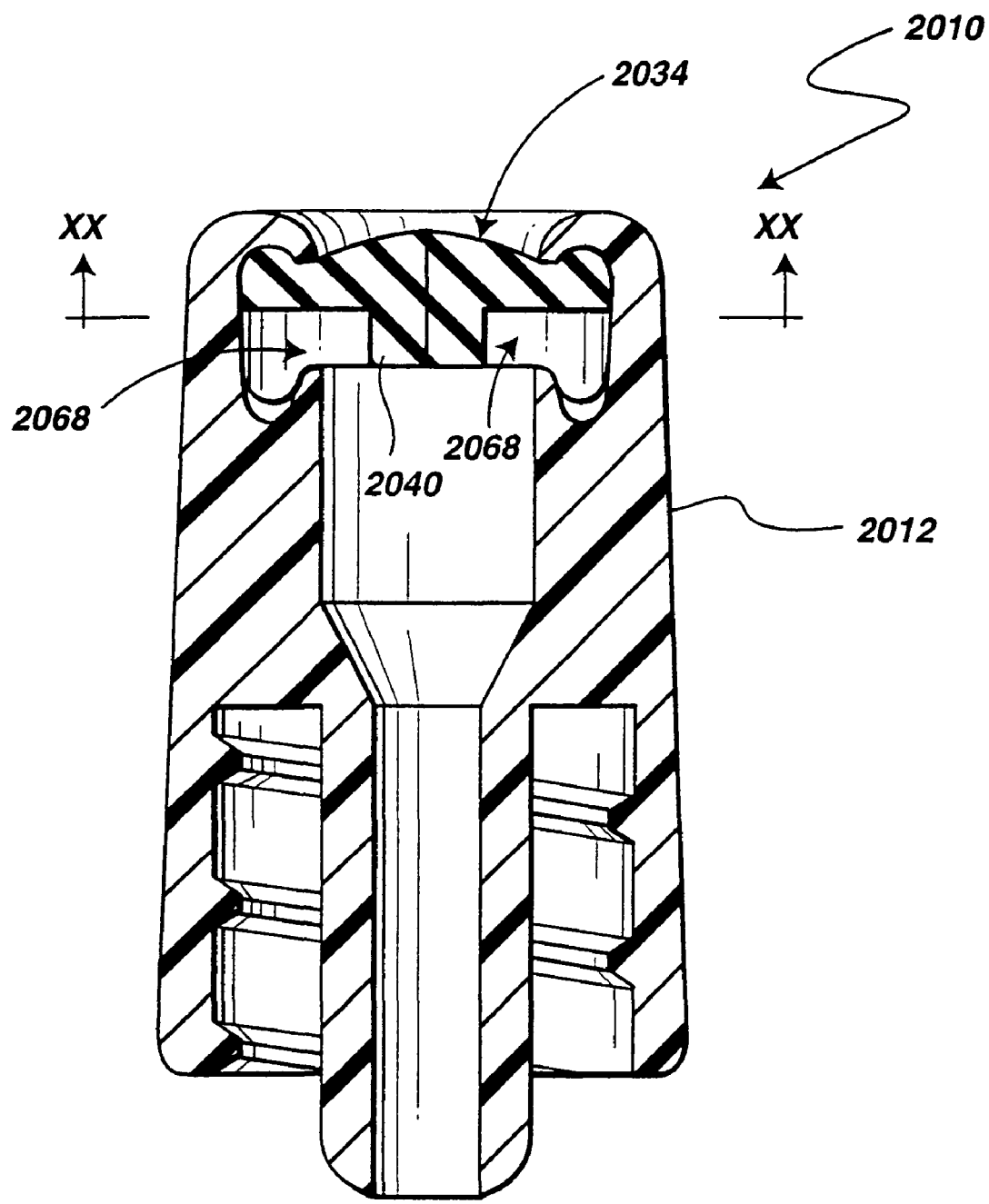
FIG. 18 is a longitudinal cross-section of a mock-up prop device created to show the concept of U.S. Pat. No. 5,474,544 wherein the section is taken perpendicular to the central slit.

Referring to FIG. 17, a another embodiment of the present invention is shown. The corresponding components of the embodiment in FIG. 1 are designated with the same or similar reference number advanced by 100. The upper housing and septum are identical to the corresponding components of FIG. 1. However, this embodiment shows an extension with a distal focused sealing region 180 within the housing midportion 114. The focused sealing region 180 includes narrow lower projection 182 which compress the extension 140 between lower projections 182 which function in a manner similar to that described for the projections 50 of FIG. 1.

The housing slots can be covered and a means for rebounding the thin lateral walls of the cutout extension could be provided intermediate the extension walls and the slot cover. A highly compressible filler, such as the type disclosed in U.S. Pat. No. 5,474,544, could be provided lateral the extension (See, e.g. FIGS. 21, 22, and/or 25). This could be used as another means to rebound the extension walls and also means to prevent fluid flow within the portion of the housing receiving the luer tip and to provide an expansion member, which fills the volume, vacated by the luer tip upon withdrawal.

FIGS. 19-25 show various alternative septum configurations for mounting with housing structure having a similar proximal portion to that of the housing 10 of FIG. 1. These figures illustrate the incorporation of different septum extensions and sealing members along with the basic upper septum configuration of FIG. 1.

Figure 20:
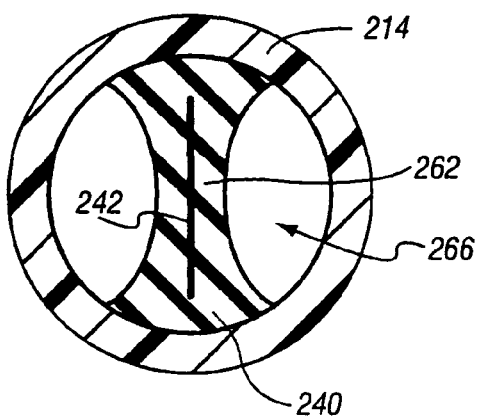
FIG. 20 is a view taken along line 20-20 of FIG. 19.
Figure 19:
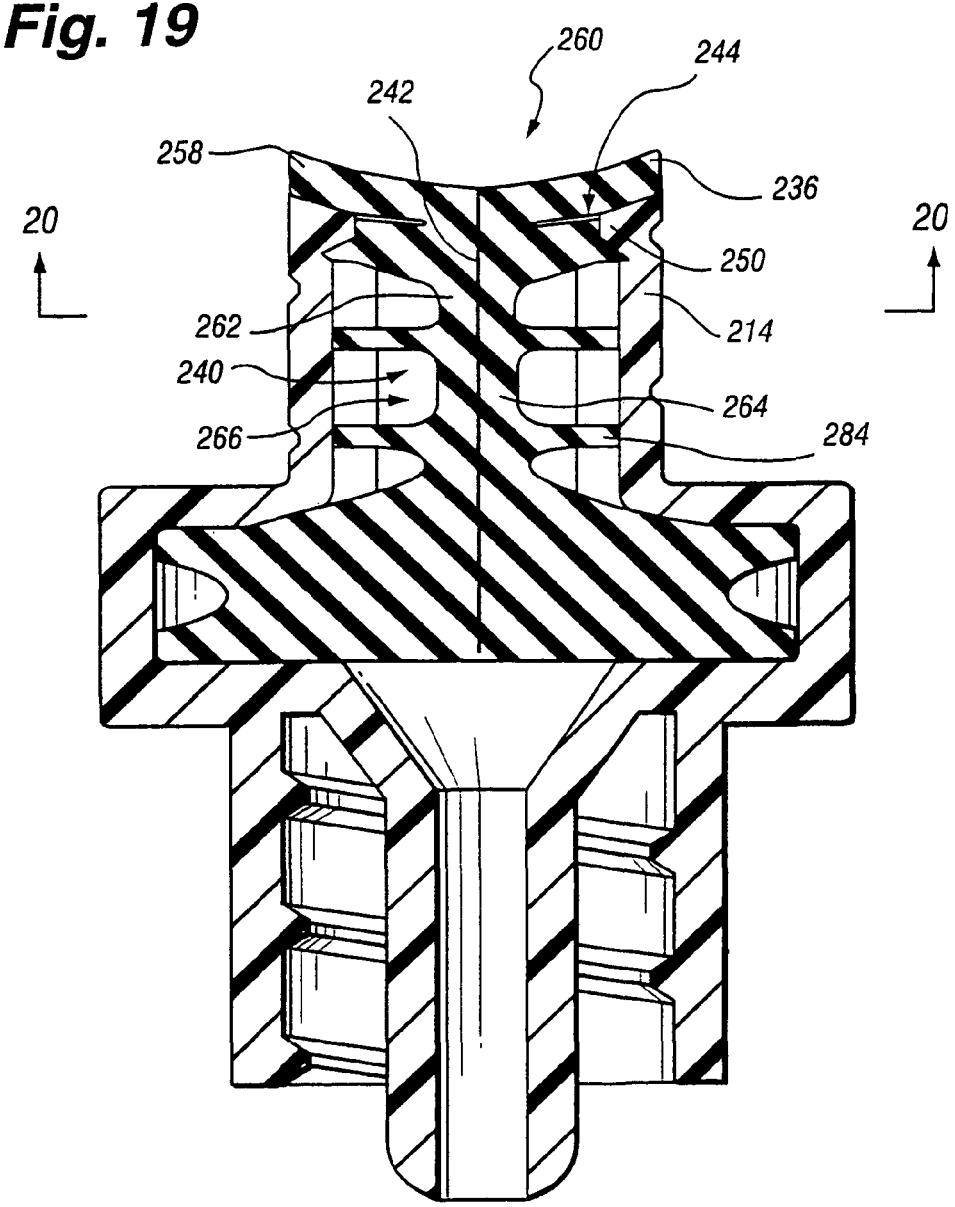
FIG. 19 is a longitudinal half-section of another embodiment of the present invention wherein the section is taken perpendicular to the central slit.

FIG. 19 and FIG. 20 show an embodiment having an extension 240 with deeper concave septum cutouts 266 and very thin portions 264 of lateral septum walls 262 which are supported by narrow transverse discs 284 which extend between the concave lateral septum walls 262 and housing 214. The housing 214 is of substantially uniform thickness throughout its circumference (except for external thread receiving recesses 228). The cutouts 266 are deeper than the septum cutouts 66 of FIG. 1 to accommodate the additional volume of the proximal housing 214 within the transverse axis of deflection of the septum lateral walls 262. The discs 284 function to enhance the decreased rebound force associated with the loss of elastomeric mass associated with thinning the septum walls 262 in this region so that withdrawal of the luer cannula, discs 284 rebound the lateral walls 262 to return the slit 242 to a closed position. The combination of thinner lateral septum walls 262 and discs 284, helps to reduce the need for the provision of corresponding cutouts in the proximal housing 214 or limits the need for such cutouts to penetrate transversely all of the way through the lateral housing wall. This configuration is made possible by the projecting members 250 and platform 244 which comprise holding members holding the thin walled extension 240 up by engaging the lateral portion of the proximal portion of the septum (upper portion 236 including elevated portions 258 and the lower portion intermediate projections 250) to hold the extension against forcible longitudinal pressure during advancement of the tip against the septum face. These holding members thereby prevent longitudinal collapse of the thin portions 264 of lateral septum walls 262 of the extension 240 during luer insertion.

Figure 22:
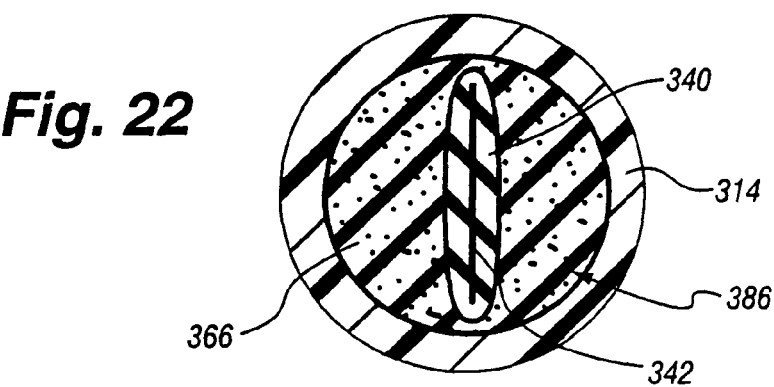
FIG. 22 is a view taken along line 22-22 of FIG. 21.
Figure 21:
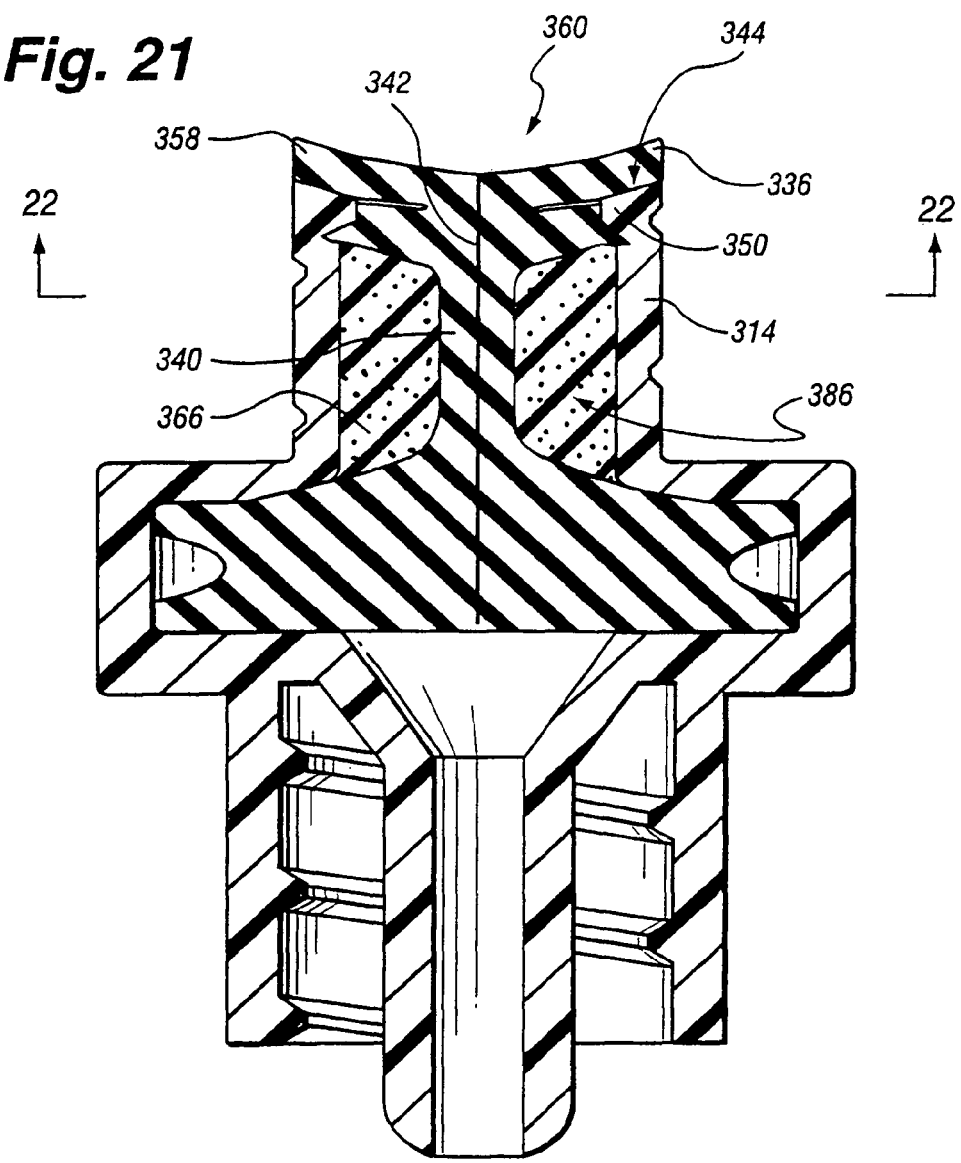
FIG. 21 is a longitudinal half-section of another embodiment of the present invention wherein the section is taken perpendicular to the central slit.

FIG. 21 and FIG. 22 show alternative embodiments with a modified extension 340 and cutouts 366. The embodiment is otherwise unchanged from the embodiment of FIG. 19. The modified cutouts 366 can be filled with a highly compressible material 386 having a high resting volume and a low compressed volume such as medical foam rubber to eliminate any residual resting dead space and to facilitate deflection back to the resting position upon luer cannula withdrawal. The extension 340 now is configured as a thin rectangular rod or beam surrounded by the highly compressible member 386. If the cutouts 366 are so filled the need for the transverse discs as shown in FIG. 19 is obviated.

Figure 24:
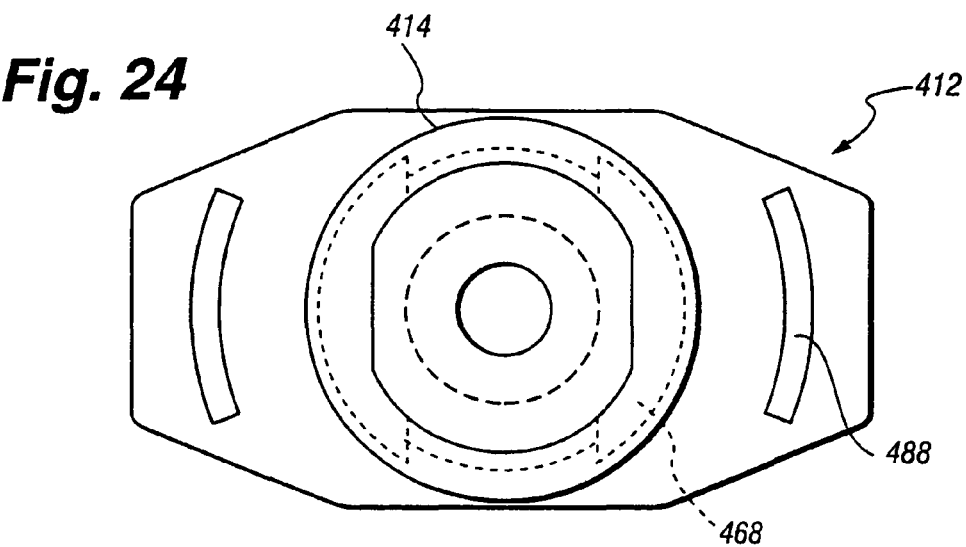
FIG. 24 is top plan view of the luer receiver of FIG. 23.
Figure 23:
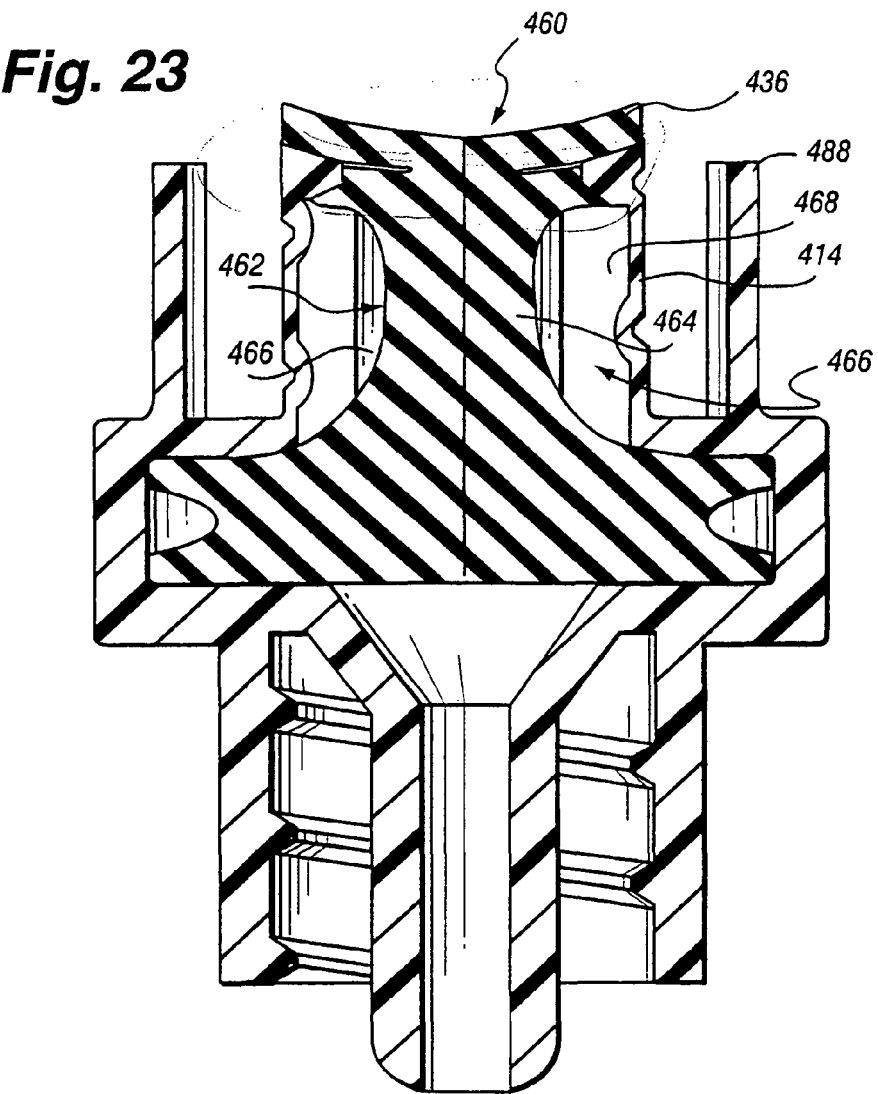
FIG. 23 is a longitudinal half-section of another embodiment of the present invention wherein the section is taken perpendicular to the central slit.

FIGS. 23 and 24 shows the basic configuration of FIG. 19 wherein the cutouts 466 in the septum extension are less deep and corresponding transverse housing cutouts 468 producing recesses directly within the proximal housing 414 are provided. Opposing outer struts 488 are provided to provide outer support for the luer lock connector when it has been threaded onto housing 414.

Figure 25:
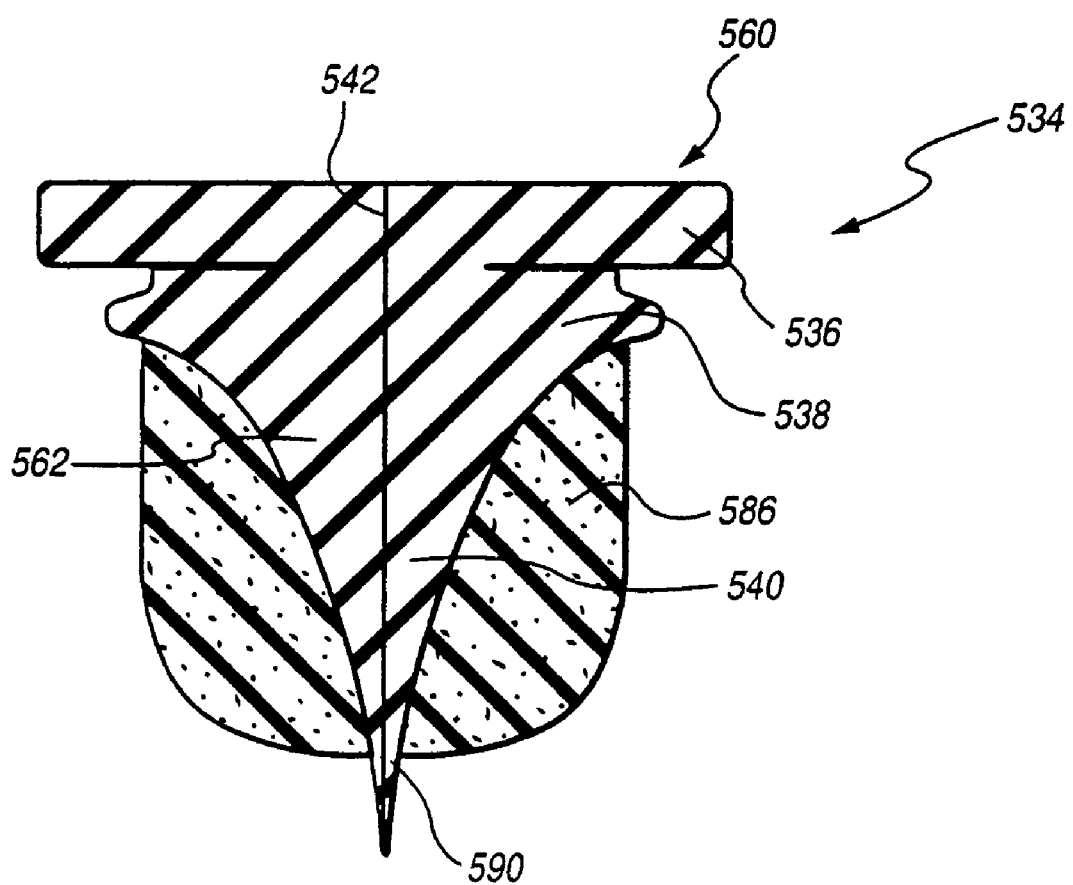
FIG. 25 is a sectional view of a septum provided in accordance with a further alternate embodiment of the invention.

FIG. 25 shows another septum embodiment 534 having a septum extension 540 mounted with a lateral highly compressible member 586. The septum 534 is configured for mounting within a housing such as that shown as the proximal housing 414 of FIG. 23 or 214, 314 of FIGS. 19-22. Note the provision of the compressible member intermediate the proximal housing and septum extension to fill the lateral receptive space between these structures formed by their respective cutouts. In aggregate, the tiny air spaces of the foam rubber are functionally analogous to open cutout spaces in that they receive the expanded mass of the lateral walls 562. While the enlarged sealing member of FIG. 1 serves to isolate the distal fluid chamber from the septum cutouts, if the sealing member is not provided or is not configured to provide this function, the compressible member serves to maintain resting displacement of fluid from the cutout area lateral the extension thereby minimizing negative fluid deflection upon withdrawal of the luer cannula. A distal duckbill valve sealing member 590 projects from the extension 540. The duckbill valve also minimizes negative fluid deflection as it opens and closes with minimal material displacement and precludes fluid counter flow upon luer withdrawal.

A general description several presently preferred embodiments of the invention is as follows:

A luer receiver for receiving a luer lock connector, the receiver includes a housing defining a longitudinal axis and an elastomeric septum mounted with the housing, the septum defines a longitudinal axis and includes an upper portion defining an upper face, an elastomeric septum extension projects distally from the upper portion within the housing. The septum includes a sealed perforation extending through the upper portion and at least partially through the extension. The sealed perforation is preferably a sealed slit and positioned centrally along the longitudinal axis of the septum and centrally along the longitudinal axis of the extension. The slit defines opposing internal walls which contact each other to seal the slit, the internal walls preferably extend from the upper portion into the extension and thereby comprises an uninterrupted sealed slit entirely through the central portion of the extension without resting deadspace so that fluid is not retained in the slit when the luer cannula is not within the slit. The extension preferably has a smaller transverse width than the upper septum portion and can include diametrically opposing cutouts defining outwardly facing concavities which may be oriented in the longitudinal axis or transverse axis or along both axes. The thin extension walls provide for the displacement of the lateral walls of the extension to occur within the boundaries of the threaded luer lock connector. However an unexpected result of this thinning is a particularly favorable penetration force curve for the insertion of the luer tip. The luer tip "pops through" the narrow upper portion including any narrow zone of focused compression to enter the zone of the extension which provides for easy penetration. However, because the extension is preferably of narrow width and is comprised of a soft and elastic elastomer to allow easy elastic displacement, the extension is held to prevent longitudinal collapse when a forcible longitudinal force is applied against it to enter the sealed slit. For this reason the receiver further includes a holding member, such as the upper portion of the housing which can be configured to form a plateau or buttress or which can project into a recess in the upper portion or can otherwise hold the upper portion, the holding member holds the extension against excessive downward deflection or collapses into the housing despite its preferred configuration with limited side wall thickness and therefore limited longitudinal support. The holding member holds the upper portion adjacent the proximal end of the housing so that the upper portion is held in a position adjacent the end when the luer tip is forcibly pressed against the upper portion. The extension, which is preferably integral with the upper portion, and thereby held by the upper portion in a receptive position to receive the large luer tip into the slit of the extension because the extension is positioned in a relatively fixed position along the longitudinal axis of the housing by the upper portion. Indeed the extension can be seen to be suspended from the upper septum portion and from the holding member.

In a preferred embodiment the extension comprises an elastomeric rod or beam including a central slit which is closed along its entire length and held in a suspended position from a septum mounted with the proximal end of the housing, wherein the slit is connected with the perforation through the septum. This configuration allows the large diameter luer cannula to penetrate into the narrow and thin walled rod from the upper portion of the septum without longitudinally collapsing the rod. The rod thereby provides an enclosed and sealed perforation or slit, which is closed along its entire length projecting distally within the housing toward the outlet.

The septum preferably includes at least one sealing region positioned along the septum where the perforation or slit is tightly sealed. In a preferred embodiment a plurality of sealing regions are provided. These regions can be provided by configuring at least one of the septum and the housing such that the opposing inner walls of the slit press more tightly against each other within these regions than along the slit immediately adjacent the outer face. This allows easy penetration at the outer face but ensures tight sealing. The regions of increased pressing can be provided by using thicker elastomeric walls adjacent the region or by configuring the housing and the septum such that the housing squeezes against the septum to thereby deflect the opposing walls into more tight opposition within the regions. At least one of the sealing regions is preferably of a length less than one half the total length of the slit and is defined by a focused region of compressive force applied to the septum by projecting compressing members of the housing.

In the preferred embodiment the two opposing slit walls of the septum which define and bound the closed slit are preferably deflected by the advancing luer tip laterally to a greater extent than they are deflected downwardly into or within the housing. Furthermore, rather than solely swinging open about a laterally fixed axis so that the opposing walls face downward in the open position, the opposing slit walls preferably spread transversely apart to a greater extent than they swing downward upon receipt of the luer tip such that the slit walls continue to face substantially toward each other after the luer tip has been inserted into the slit. This feature is important since downward displacement into the housing increases the septum mass within the housing thereby further compromising the limitations of space previously discussed. If the slit walls swing downwardly the thickness of the downward projecting walls is added to the volume of septum which must be laterally displaced by the penetrating luer tip. As taught supra, the upper portion of the septum is preferably of greater diameter than the portion immediately below the upper portion. The upper portion is preferably circular and is preferably buttressed by a wall or plateau, which is preferably a complete ring but may extend only partially about the circumference of the upper portion. The upper portion is held in place along or adjacent the lateral wall of the upper portion to prevent downward displacement of the lateral portion of the upper portion. The lateral portion of the upper portion is preferably more fixedly held against downward displacement than the more central portion adjacent the slit so that central downward deflection toward the housing bore is induced by pressing a luer tip against the central portion. However the septum and housing are configured such that the portions of the septum lateral to the long axis of the slit deflect laterally to a greater extent than they deflect downwardly into the housing. The housing is configured to provide for this lateral deflection of the septum above, within and/or about the housing.

In a presently preferred embodiment an axis of maximum transverse displacement of the extension is provided along a transverse axis defined perpendicular to the midpoint of the long transverse axis of the slit. The focused nature of the maximum displacement is achieved by providing a slit, which is nearly equal to the size of the luer tip, so that the midpoint of circular cross-section of the luer tip predictably falls at the midpoint of the slit. The regions of reduced housing wall volume and/or reduced septum wall volume are then positioned to be aligned within the axis of maximum displacement. As previously shown, the transverse section of the septum extension cutout can be concave to match the corresponding circular cross-section of the luer tip so that the center portion of the lateral wall of the extension is thinner than the more lateral portion. The corresponding degree or depth of the cutout in the internal wall of the housing facing the septum cutout can be matched so that the deflection of the extension can be accommodated by the space intermediate the lateral wall of the septum cutout and the inner wall of the housing cutout. Such housing cutouts can be seen to include many configurations and combinations such that the deflection of the lateral walls of the septum extension is accommodated within confines of the luer lock connector.

As discussed previously, in one embodiment the extension of the septum includes highly compressible members mounted adjacent the extension and preferably within the cutouts. These compressible members can be portions of the extension configured to be easily compressed such as vertical or horizontal thin walled discs projecting to the interior wall of the housing or can be provided by a filling material mounted within the cutouts which is inherently highly compressible. These compressible members are particularly for use when the cutouts in the housing wall do not extend all the way through the wall so that the extension is enclosed as by a complete circumferential housing wall provided about the extension. When thin discs are used the spaces or cutouts of the lateral wall of the septum extension are provided between the discs to accommodate lateral deflection when the luer tip is inserted into the slit. The use of laterally oriented narrow discs presents a minimum of cross-sectional area of the septum for compression against the interior wall of the housing. Preferably the discs are aligned with the long transverse axis of the slit. These discs may be slightly compressed against the housing at rest to more tightly seal the slit but are markedly compressed against the interior wall when the luer tip is received into the slit.

Medical liquid can be transferred between a medical liquid storage container and a chamber using a luer lock connector, the connector having a central male luer cannula defining an outer cannula wall, the connector being mounted in fluid connection with the container, the chamber having a luer receiver mounted with the chamber, the receiver including a housing having an inlet, the housing containing a sealing septum mounted adjacent the inlet, the septum having an upper portion including an outer face and a slit defining a long transverse axis extending through the face, the slit defining two lateral opposing walls defining two opposing inner faces bounding the slit, the opposing faces contacting each other to seal the slit, the septum including a distal septum portion projecting within the housing, the slit extending at least partially through the distal portion, the receiver including a member for engaging the upper portion of the septum, wherein the method includes steps of:
1. pressing the luer tip against the outer face, the member holding the upper portion of the septum in a position adjacent the inlet such that the upper portion is held while the luer tip penetrates into the slit and into the outer face of the septum,
2. deflecting the slit walls laterally such that the opposing inner faces directly press against the outer cannula wall after the luer tip has been advanced into the slit,
3. threading the luer lock connector about the housing such that the septum, the luer tip, and at least a portion of the housing are retained within the luer lock connector, and
4. flowing liquid through the luer tip and into the chamber.

Another method of transferring medical liquid between a medical liquid storage container and a chamber can be performed using a threaded luer lock connector, the connector having a central male luer cannula, the connector being mounted in fluid connection with the container, the chamber having a luer receiver mounted with the chamber, the receiver including a housing having an inlet, the housing containing a sealing septum mounted adjacent the inlet, the septum having an upper portion including an outer face and a perforation, the septum including a distal septum extension projecting within the housing the perforation being circumferentially enclosed by the extension and extending at least partially through the portion, the receiver including a member for engaging the upper portion of the septum, the method comprising steps of:
1. pressing the luer tip against the outer face, the member holding the upper portion of the septum in a position adjacent the inlet such that the upper portion is held while the luer tip penetrates into the slit and into the outer face of the septum and into the extension,
2. deflecting the extension laterally with the luer cannula such that the extension is elastically expanded within the housing in direct contact with the male luer cannula the cannula penetrating at least partially through the extension into fluid connection with the chamber,
3. threading the luer lock connector about the housing such that the upper portion of the septum, the luer tip, at least a portion of the extension, and at least a portion of the housing is retained within the threaded luer lock connector,
4. flowing liquid through the luer tip and into the chamber.

Another method of transferring medical liquid between a medical liquid storage container and a chamber can be performed using a threaded luer lock connector, the connector having a central male luer cannula, the connector being mounted in fluid connection with the container, the chamber having a luer receiver mounted with the chamber, the receiver including a housing having an inlet, The method can includes steps of:
1. Attaching an elastomeric septum having a perforation defining a longitudinal axis to the receiver adjacent the inlet of the housing.
2. Suspending an elastomeric rod from the septum into the housing the rod having a sealed lumen defined by opposing internal walls.
3. Inserting the male luer into the perforation of septum, the perforation directing the male luer into the lumen, the male luer deflecting said internal walls to open the lumen as the male luer passes into the rod.
4. Flowing liquid through the male luer and though the lumen into the chamber.

As noted above the housing and the suspended rod within the housing can be sized and configured such that the entire rod remains within the confines of the threaded luer lock connector when the male luer has been received into the lumen and the connector has been threaded onto the receiver. The rod and housing can be further configured such that the rod is entirely contained within the housing when the connector has been threaded onto the receiver.

Many additional modifications are included within the scope of this teaching. For example, an embodiment (not shown) for penetration by a male luer can include a combined integral housing and septum comprised of a single elastomer having regions of different durometers wherein the central penetrable portion has a low durometer such as 20-30 and the outside thread-able portion has a high durometer such as 70-80. In such a structure wherein the housing and septum have no definable boundaries, the cutouts nevertheless preferably comprise elongated concave cutouts or recesses within a distally projecting elastomer wherein the cutouts extend longitudinally lateral to a central and longitudinally projecting slit within the elastomer to allow deflection of the elastomer within the confines of the threaded luer lock connector.

Figure 26:
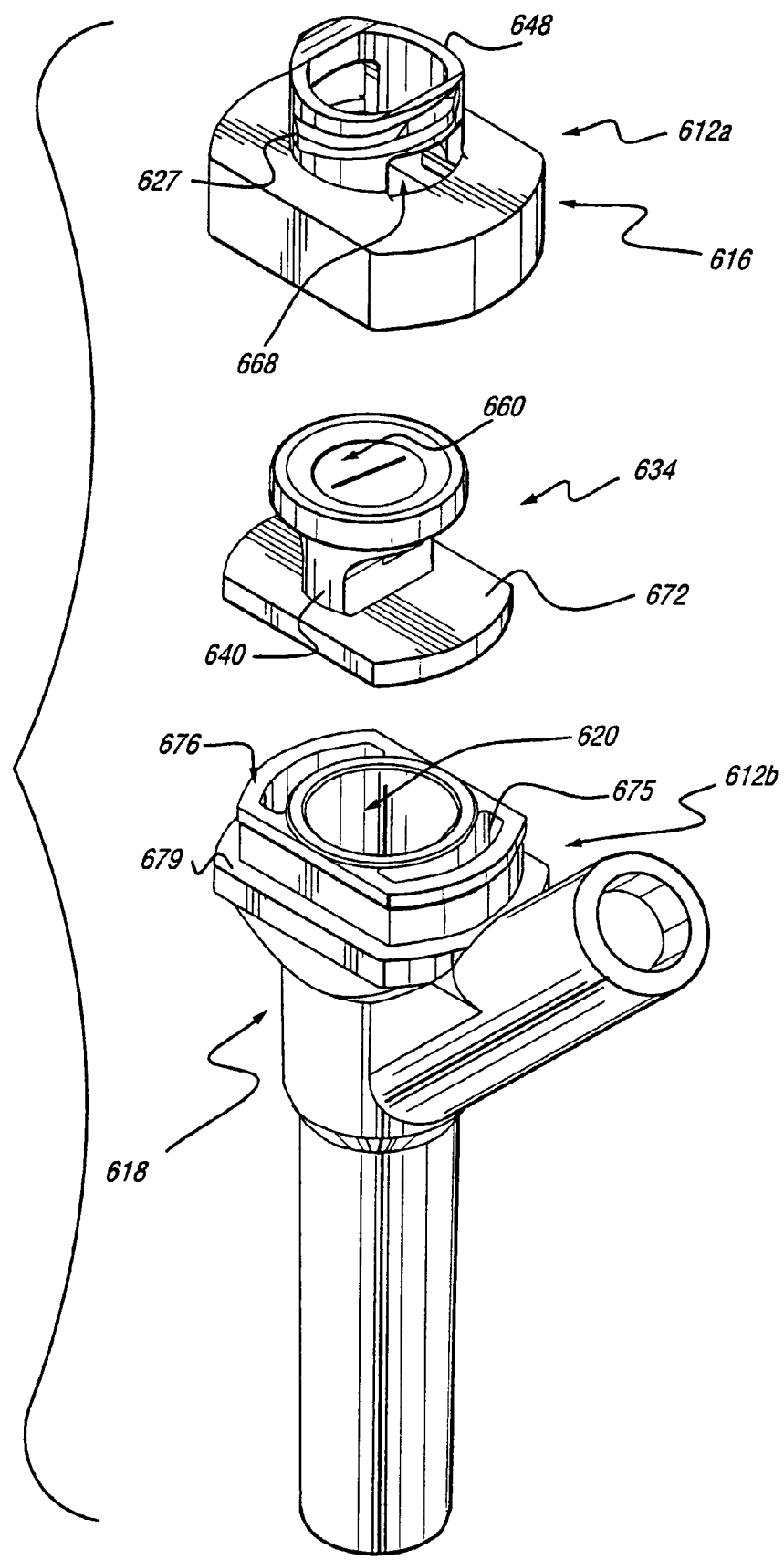
FIG. 26 is an exploded perspective view of a presently preferred embodiment of the invention incorporated in a Y-site.

Referring now to FIG. 26, there is shown therein an exploded perspective view of a presently preferred embodiment of the luer receiver of the invention, incorporated in a Y-site. More particularly, referring to the views of FIGS. 26-42, the luer receiver of this embodiment is constructed from a two-part housing including an upper housing body 612a and a housing base 612b. The upper housing body 612a includes proximal portion 614 and central portion 616. The housing base 612b comprises the distal portion 618 which in the illustrated embodiment is configured as a Y-site. The upper housing body 612a and housing base 612b have a complementary shape for being operatively engaged, capturing the septum 634 therebetween. Thus, in the illustrated configuration, the end wall 674 and side walls of the upper housing body 612a define a bottom peripheral surface 677 sized for engaging a complementary ledge 679 defined on housing base 612b. Furthermore, spaced projections 671 project inwardly of the central portion 616 of upper housing 612a for selectively being received vertically below a peripheral projection or rim 673 on housing base 612b, to snap lock the housing parts together.

Similar to the structure shown in FIGS. 4-16, projecting luer ears or tabs 627 are defined on housing proximal portion 614. Moreover, as in the prior embodiments, housing recesses or cutouts 668 are also defined in the proximal portion 614 of the housing for allowing lateral deflection the walls of extension portion 640 at cutouts or recesses 666.

As in the embodiments described above, septum 634 has an enlarged upper portion 636 for being seated on elevated portions 646 and trough portions 648 of the proximal portion 614 of the housing. Slots 654 are defined between upper septum portion 636 and lower septum portion 638 for allowing the upper septum 636 to deflect upwardly for being seated on upper surfaces 656 of projections 650 along the platform elevations 646.

The upper surface of septum 634 in this embodiment is defined as a dish-shaped upper surface 660. Thus, as shown for example in FIG. 40, the outside rim of the septum upper disk 638 is thicker than the center thereof. The dish shape serves two purposes. The first is to keep the luer tip centered on the top surface of the septum when accessing the Y-site. The second purpose of the dish shape surface is to create more interference with upper body 612*a* to reduce the chance that the septum upper portion 636 will pass through the top of the body during access.

A further feature of the embodiment illustrated in FIGS. 26-42 is the provision of support ribs 645 on the sides of septum 634. More particularly, septum 634 has lower septum portion 638 as a compression ring just below side cuts 654. This compression ring 638 is compressed in two directions by projections 650 of the upper body 612*a*. When the product is accessed, the compression ring is moved down and out of contact with a body thus relieving the compression. Ribs 645 give the compression ring the support necessary to re-engaged the compression ring after removal of the accessing luer.

To position and mechanically lock the luer receiver components together, the lower portion 672 of septum 634 has on a bottom surface thereof two protrusions 669 that project downwardly therefrom, extend generally in an arc, and are located near the outer periphery thereof. The bottom Y-site 618 has corresponding holes or receptacles 675 for receiving protrusions 669, to correctly position and laterally lock septum 634 relative to be housing parts 612*a* and 612*b*. Thus, during assembly, septum 634 is seated on upper wall 676 of Y-site 618 with protrusions 669 disposed in holes or receptacles 675. The housing body 612*a* is then firmly attached to the bottom Y-site 618 by snapping protrusions 671 past rim 673, with the septum 634 compressed between housing parts 612*a* and 612*b*. The upper surface 676 of bottom Y-site 618 provides support to the septum 634 close to the duckbill 643 defined at the distal end of slit 642. The protrusion of the septum 634 into the holes or recesses 675 of the Y-site 618 provides a mechanical entrapment to maintain the position of septum 634 within the housing provided by the combination of the Y-site and the upper body 612*a*. This reduces the chance the septum could be deformed and become unseated, thus compromising the fluid seal between the septum and Y-site structure. It also reduces the chance the septum could be removed from the housing.

Figure 36:
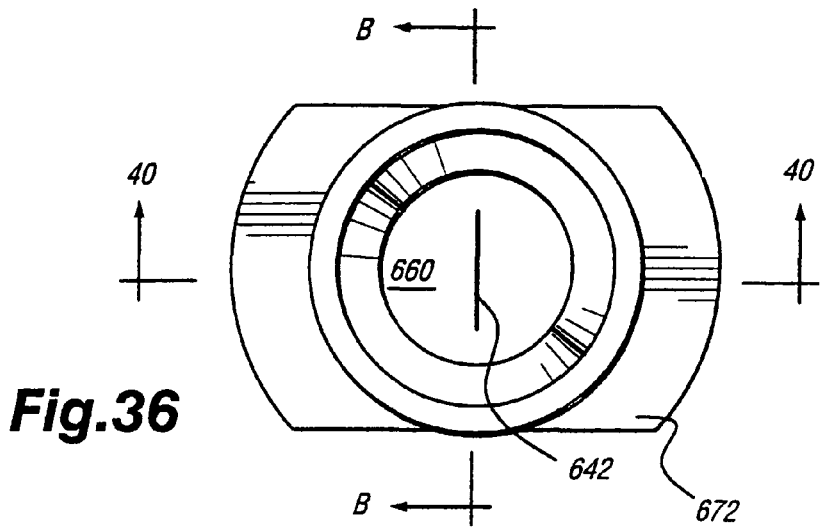
FIG. 36 is top plan view of the luer receiver septum of the embodiment of FIG. 26.
Figure 37:
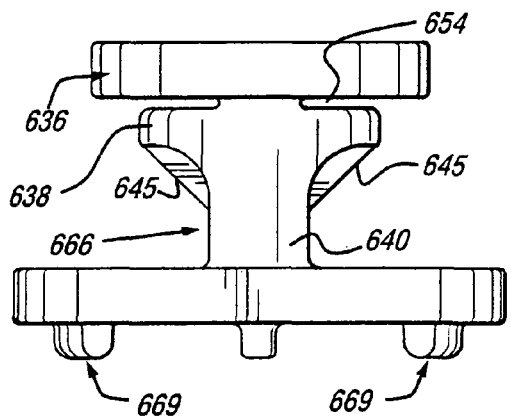
FIG. 37 is a side elevational view of the luer receiver septum of the embodiment of FIG. 26.
Figure 38:
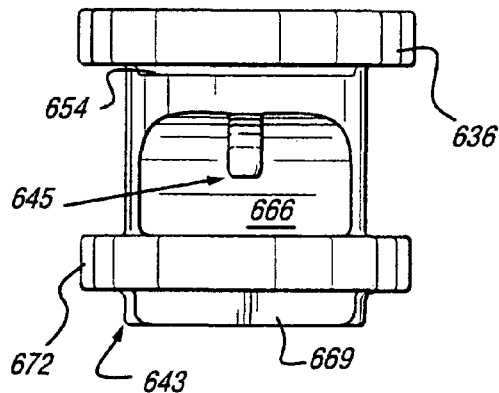
FIG. 38 is an end elevational view of the luer receiver septum of FIGS. 36 and 37.
Figure 39:
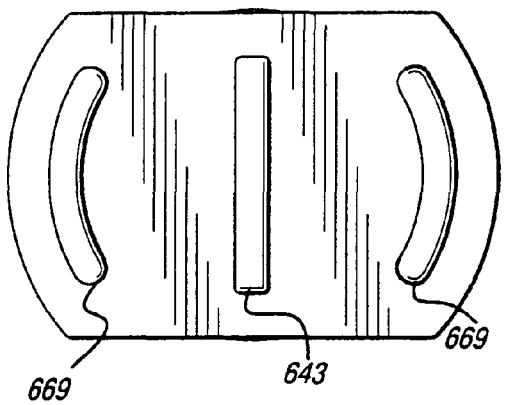
FIG. 39 is a bottom plan view of the luer receiver septum of FIGS. 36, 37, and 38.
Figure 40:
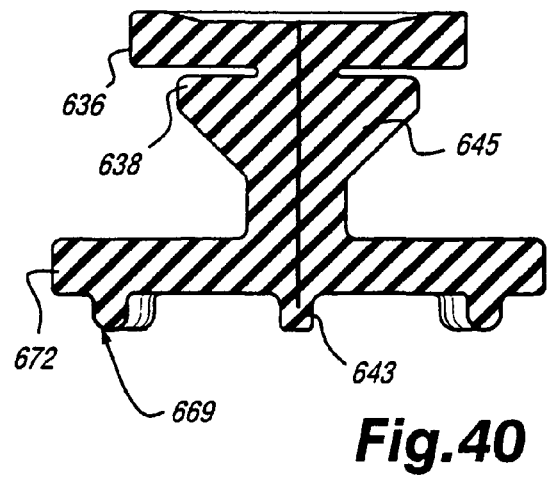
FIG. 40 is a cross-sectional view taken along line 40-40 of FIG. 36.
Figure 41:
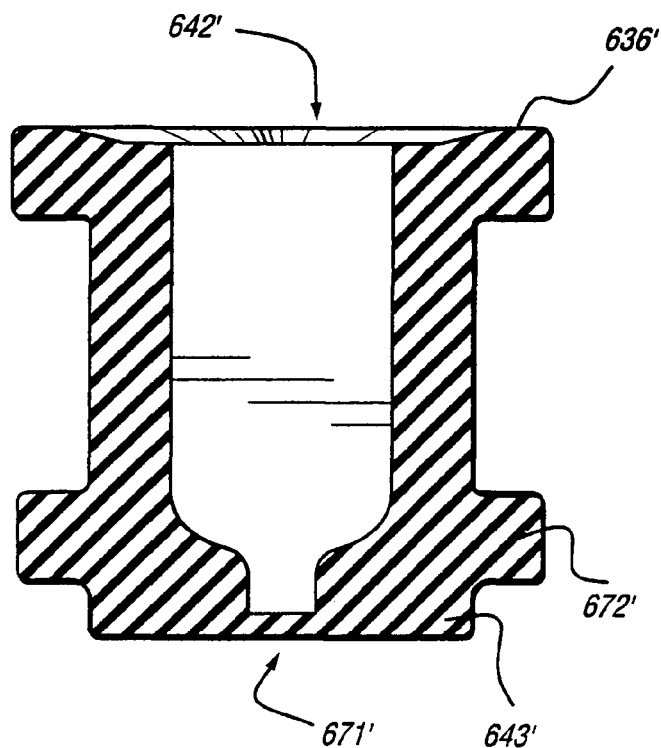
FIG. 41 is a cross-sectional view taken along line B-B of FIG. 36, showing an alternate slit configuration in accordance with the invention.
Figure 42:
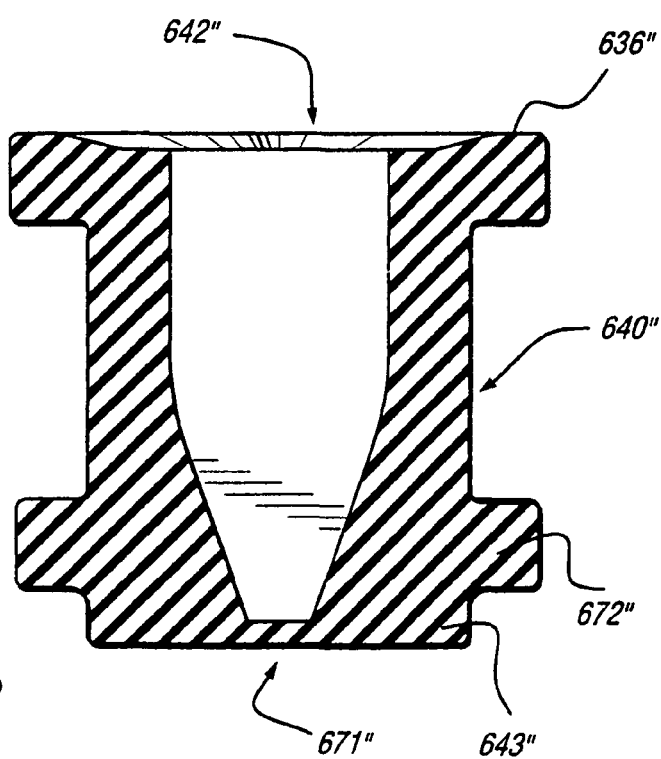
FIG. 42 is a cross-sectional view taken along line B-B of FIG. 36, showing a second alternate slit configuration in accordance with the invention.

Referring now to FIGS. 41 and 42 there shown therein cross-sectional views taken along line B-B of FIG. 36, depicting two alternate slit configurations in accordance with preferred embodiments of the invention. Slit 642 may have a substantially uniform slit width along the entire length thereof through septum 634. As an alternative, as illustrated in FIG. 41, the septum 642' reduces in width as a tapered step, so that the slit has its greatest width adjacent the septum upper portion 636' and then in the distal septum portion 672' there is a stepped reduction in width of septum slit 642', to a minimum width in duckbill portion 643'. This stepped reduction in slit width allows a wide luer taper to penetrate far enough to open the slit for fluid flow into Y-site passage 620, while still sealing on the shaft of a smaller blunt cannula which completely penetrates the septum. As shown, the slit 642' is preferably incomplete, having a residual membrane 671' which is ruptured when the slit 642' is opened by insertion of the luer tip.

FIG. 42 shows an alternate slit width reduction configuration in which slit 642" is tapered along approximately one half its length. As with the embodiment of FIG. 41, the slit 642" has its greatest width adjacent the septum upper portion 636" and then in extension 640" there begins a gradual reduction in width that continues through lower portion 672", to a minimum width in duckbill portion 643". This tapered reduction in slit width also allows a wide luer taper to penetrate far enough to open the slit for fluid flow into Y-site passage 620 while still sealing on the shaft of a smaller blunt cannula which completely penetrates the septum. Again, the slit 642" is preferably initially incomplete as shown at 671".

By way of example, the Y-site base of the FIG. 26 embodiment may be transversely dimensioned so that the peripheral ledge 679 has a width of about 0.038-0.039 inches (0.965-0.991 mm) and so that the Y-site at the ledge has a width of about 0.365 inches (9.271 mm) and a length of about 0.508 inches (12.903 mm). The Y-site base 618 may be longitudinally dimensioned so that it has a main body length of about 1.305 inches (33.147 mm), whereas the side arm, which is angled at about 45 degrees, has a length of about 0.795 inches (20.193) from the longitudinal axis of the main body. The housing body portion 616 has an interior transverse length at the distal end of about 0.442 inches (11.227 mm) and an interior transverse width of about 0.296 inches (7.518 mm). Finally, in this example, the septum distal portion 672 has a length of about 0.440 inches (11.176 mm), a width of about 0.294 inches (7.468 mm), and a thickness of about 0.050 inches (1.27 mm). Meanwhile, the interior height of the housing body portion 616 is about 0.136 inches (3.454 mm), but the height above protrusions 671 is about 0.0675 inches (1.715 mm), whereas the rim 673 of the Y-site has a vertical dimension of about 0.025 inches (0.635 mm), thus leaving about 0.0425 inches (1.080 mm) for the septum distal portion 672. It should be clear that these dimensions represent only presently preferred dimension ranges and other ranges can be employed or may be learned by practice of the invention.

Figure 43:
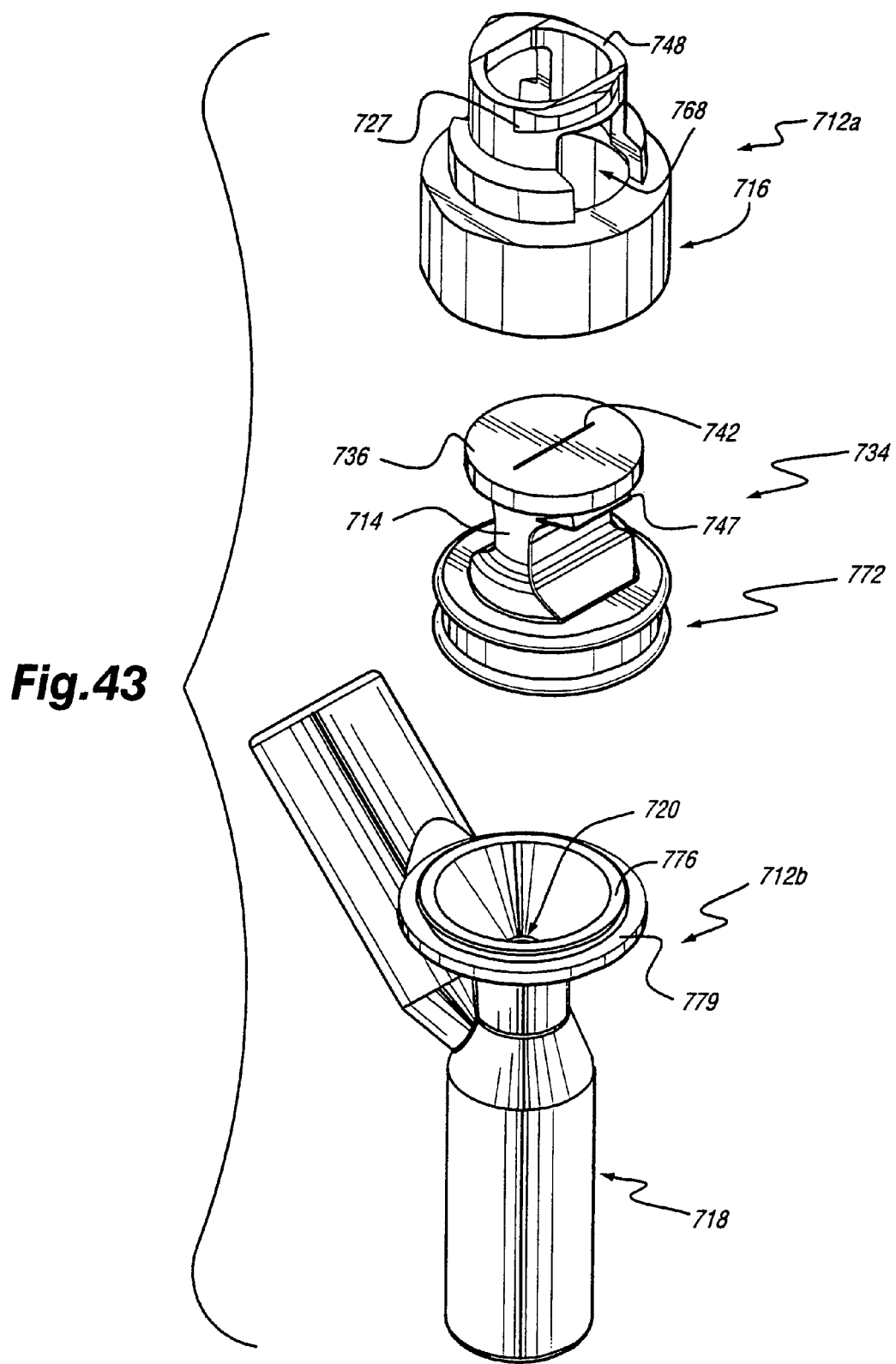
FIG. 43 is an exploded perspective view of another embodiment of the invention incorporated in a Y-site.
Figure 49:
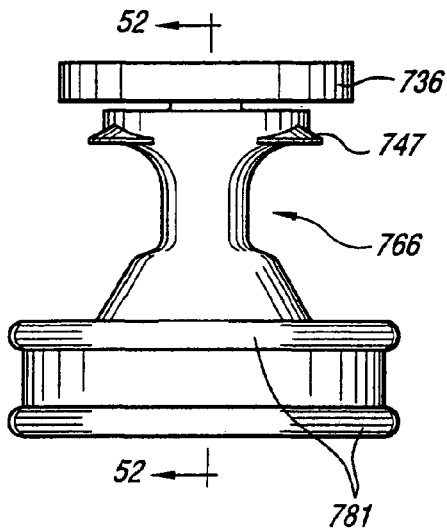
FIG. 49 is a side elevational view of the luer receiver septum of the embodiment of FIG. 43.
Figure 51:
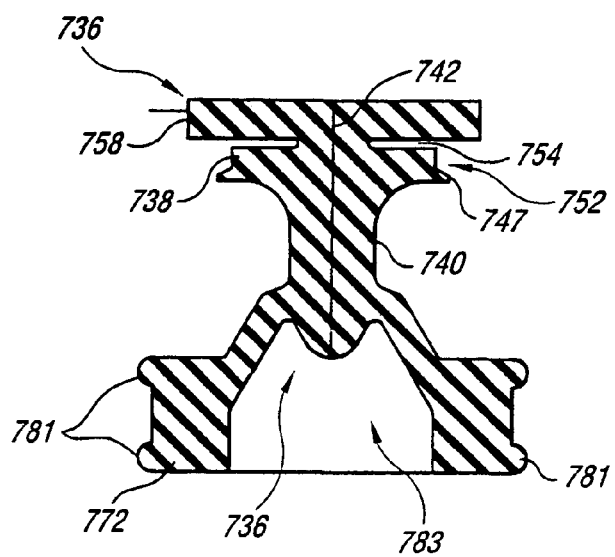
FIG. 51 is a cross-sectional view taken along line 51-51 of FIG. 50.
Figure 50:
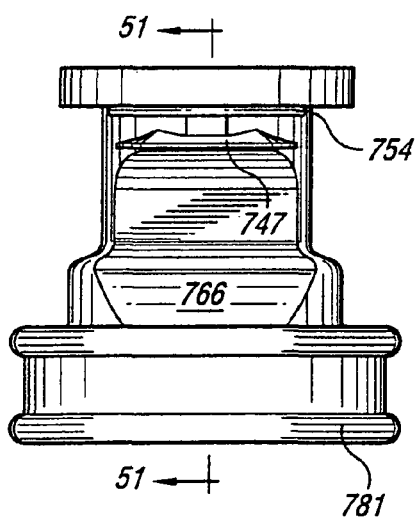
FIG. 50 is another side elevational view of the luer receiver septum of FIGS. 44 and 49.
Figure 52:
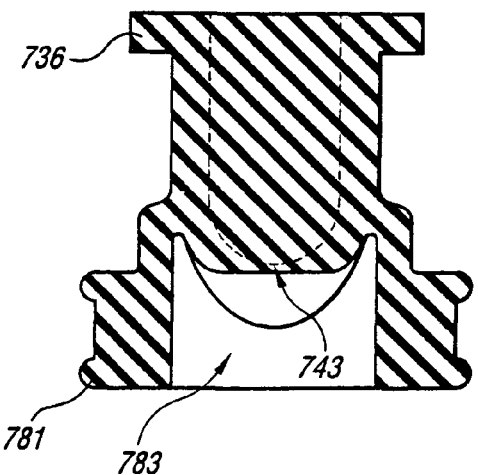
FIG. 52 is a cross-sectional view taken along line 52-52 of FIG. 49.

Referring now to FIG. 43, there is shown therein an exploded perspective view of another embodiment of the luer receiver of the invention, incorporated in a Y-site. More particularly, referring to the views of FIGS. 43-52, the luer receiver of this embodiment is constructed from a two-part housing including an upper housing body 712*a* and a housing base 712*b*. The upper housing body 712*a* includes proximal portion 714 and central portion 716. The housing base 712*b* comprises the distal portion 718 which in the illustrated embodiment is configured as a Y-site. The upper housing body 712*a* and housing base 712*b* have a complementary shape for being operatively engaged, capturing the septum 734 therebetween. Thus, in the illustrated configuration, the side walls of the upper housing body 712*a* define a bottom peripheral surface 777 sized for engaging a complementary ledge 779 defined on housing base 712*b*.

Similar to the structure shown in FIGS. 4-16, projecting luer ears or tabs 727 are defined on housing proximal portion 714. Moreover, as in the prior embodiments, housing recesses or cutouts 768 are also defined in the proximal portion 714 of the housing for allowing lateral deflection of the walls of extension portion 740 at cutouts or recesses 766.

As in the embodiments described above, septum 734 has an enlarged upper portion 736 for being seated on elevated portions 746 and trough portions 748 of the proximal portion 714 of the housing. Slots 754 are defined between upper septum portion 736 and lower septum portion 738 for allowing the upper septum 736 to deflect upwardly for being seated on upper surfaces 756 of projections 750 along the platform elevations 746. Grooves 752 for receiving projections are defined between the upper septum portion 736 and projections 747, which are received in cutouts 768 under projections 750

In this embodiment, a fluid seal is provided in the lower septum portion 772 by centerless radial compression. More specifically, a fluid seal is provided at duckbill 743 which is dependent on the radial compression of the septum without the septum having material in the center of the compression. Instead, there is a hollow central region 783 in the septum lower portion 772. Rings 781 can advantageously be added to enhance the seal. This configuration has the advantage that as the fluid pressure increases on the inside, the normal force the septum exerts on the housing increases thus enhancing the seal.

By way of example, the Y-site base of the FIG. 43 embodiment may be transversely dimensioned so that the peripheral ledge 779 has a width of about 0.031 inches (0.787 mm) and so that the Y-site at the ledge has an outer peripheral radius of 0.21 inches (5.334 mm) and an inner peripheral radius of about 0.179 inches (4.547 mm). The Y-site base 718 may be longitudinally dimensioned so that it has a main body length of about 0.892 inches (22.657 mm), whereas the side arm, which is angled at about 45 degrees, has a length of about 0.712 inches (18.085 mm) from the longitudinal axis of the main body. The housing body portion 716 has an interior transverse diameter at the distal end of about 0.363 inches (9.22 mm). Finally, in this example, the septum distal portion 772 has a diameter of about 0.370 inches (9.398 mm) or about 0.400 inches (10.16 mm) including rings 781, and a thickness of about 0.120 inches (3.048 mm). It should be clear that these dimensions are given only by way of example and other ranges can be employed or may be learned by practice of the invention.

The luer receiving valve of the instant invention is a robust valve capable of preventing leakage despite high internal fluid pressures adjacent the distal end of the septum. This leakage is prevented both with and without a penetrating luer tip in the slit. Leakage is prevented about the penetrating luer tip, in part by the relatively large mass of septum material juxtaposed with the penetrating luer tip despite the limited space available for such septum mass. As discussed supra, it is the unique matched configuration of the housing and septum which allows this higher juxtaposed septum mass to be accommodated and which allows a greater contact surface area between the septum and the side or shaft of the luer tip. In the preferred embodiment, upon full advancement of the luer tip into the septum, tight circumferential contact between the shaft and the septum is provided from the face of the septum to adjacent the tip so that sealing is greatly enhanced even under high back pressure situations such as a forced injection by a mechanical injector. In the preferred embodiment this increased mass for direct luer shaft contact is accommodated within the confines of the small circumferential luer lock by the unique combination and configuration of spaces or cavities or displacement reservoirs for focused displacement within the female luer lock when the luer tip is advanced into the septum. As discussed, the displacement reservoirs or cavities can be defined by cutouts or slots along the valve, which cutouts or slots can include portions of the housing or septum or a combination of septum and housing. These housing and septum cutouts or slots may be juxtaposed one with the other and also aligned with each other to provide a wider reservoir for greater accommodation of septum displacement. In the preferred embodiment the reservoirs are isolated from the slit and the fluid chamber and can be further isolated from the surrounding atmosphere.

As noted supra the deflection reservoirs are preferably isolated and sealed from the fluid chamber distal to the septum so that the displacement volume shift induced by the inserted luer tip is directed away from the fluid chamber. More specifically the displacement is directed into the reservoirs and not into the distal fluid chamber or pathway so that the rebound of the septum back out of the reservoirs does not induce a negative fluid deflection within the fluid chamber. In the preferred embodiment, the tight seal is provided intermediate the reservoirs and the fluid chamber by the enlarged region below the extension, which seals circumferentially with the housing. The seal can be provided by a compression seal with longitudinal compression and/or transverse compression of the septum with the housing and can be provided adjacent the distal end of the septum and/or adjacent the upper enlarged portion of the septum, if for example the reservoirs are covered laterally. If preferred, a circumferential seal adjacent the upper portion can be provided by bonding for example the lower surface of the upper portion to the plateau of the housing or by providing a compression ring above the support which compresses the peripheral edge of the upper septum portion between the ring and the circumferential support.

Figure 1A:
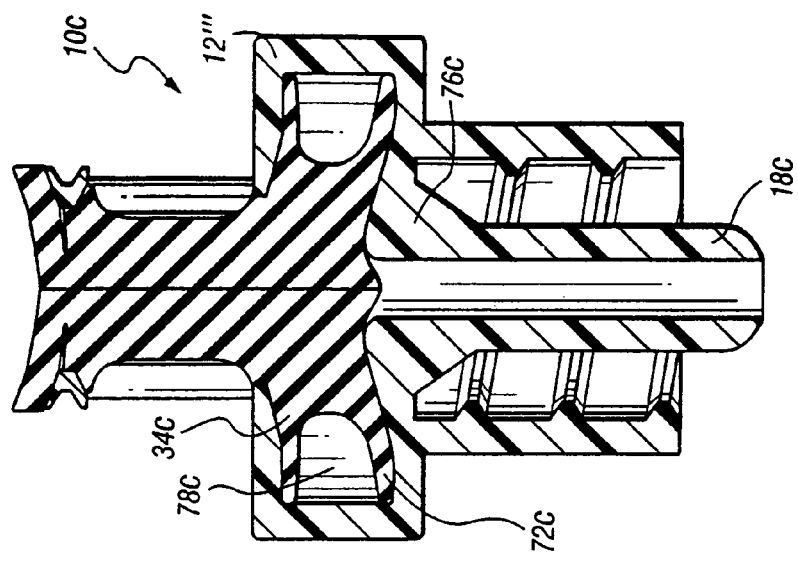
FIG. 1A is a longitudinal half-section of an alternate luer receiver housing and septum in accordance with the invention.
Figure 1B:
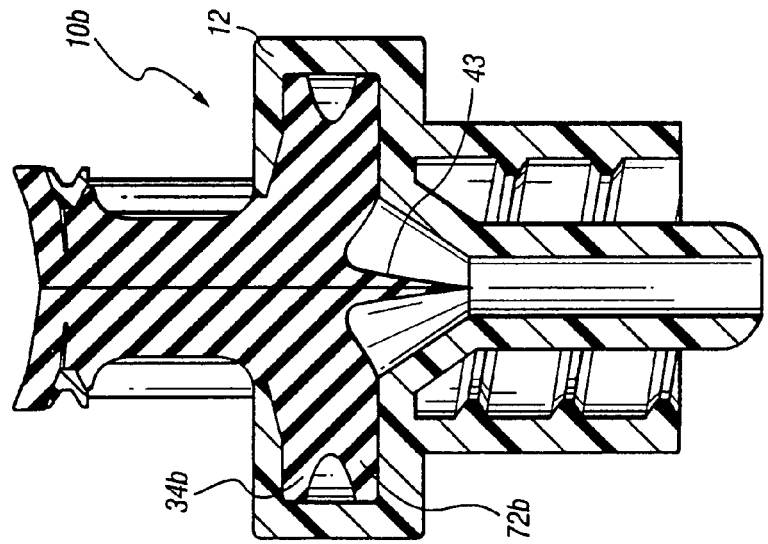
FIG. 1B is a longitudinal half-section of the receiver housing of FIG. 1 having a modified septum structure.
Figure 1C:
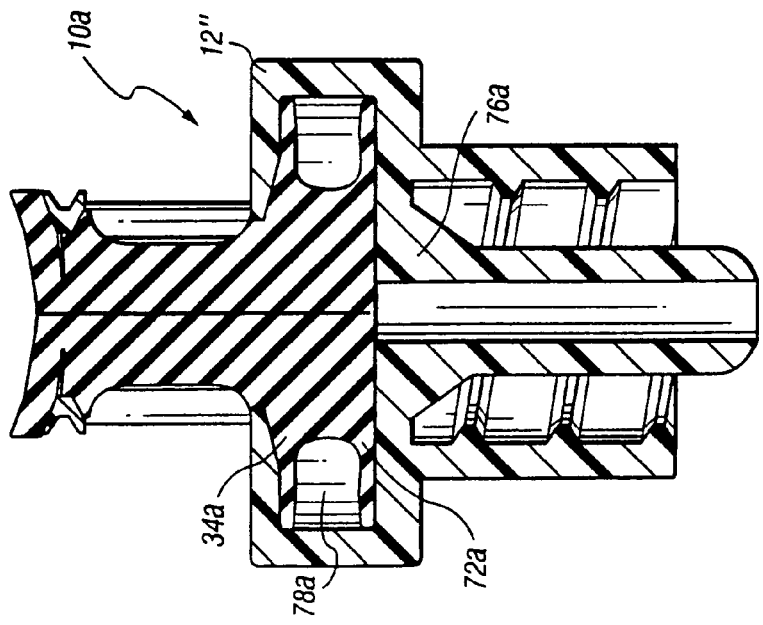
FIG. 1C is a longitudinal half-section of another alternate luer receiver housing and septum in accordance with the invention.
Figure 4:
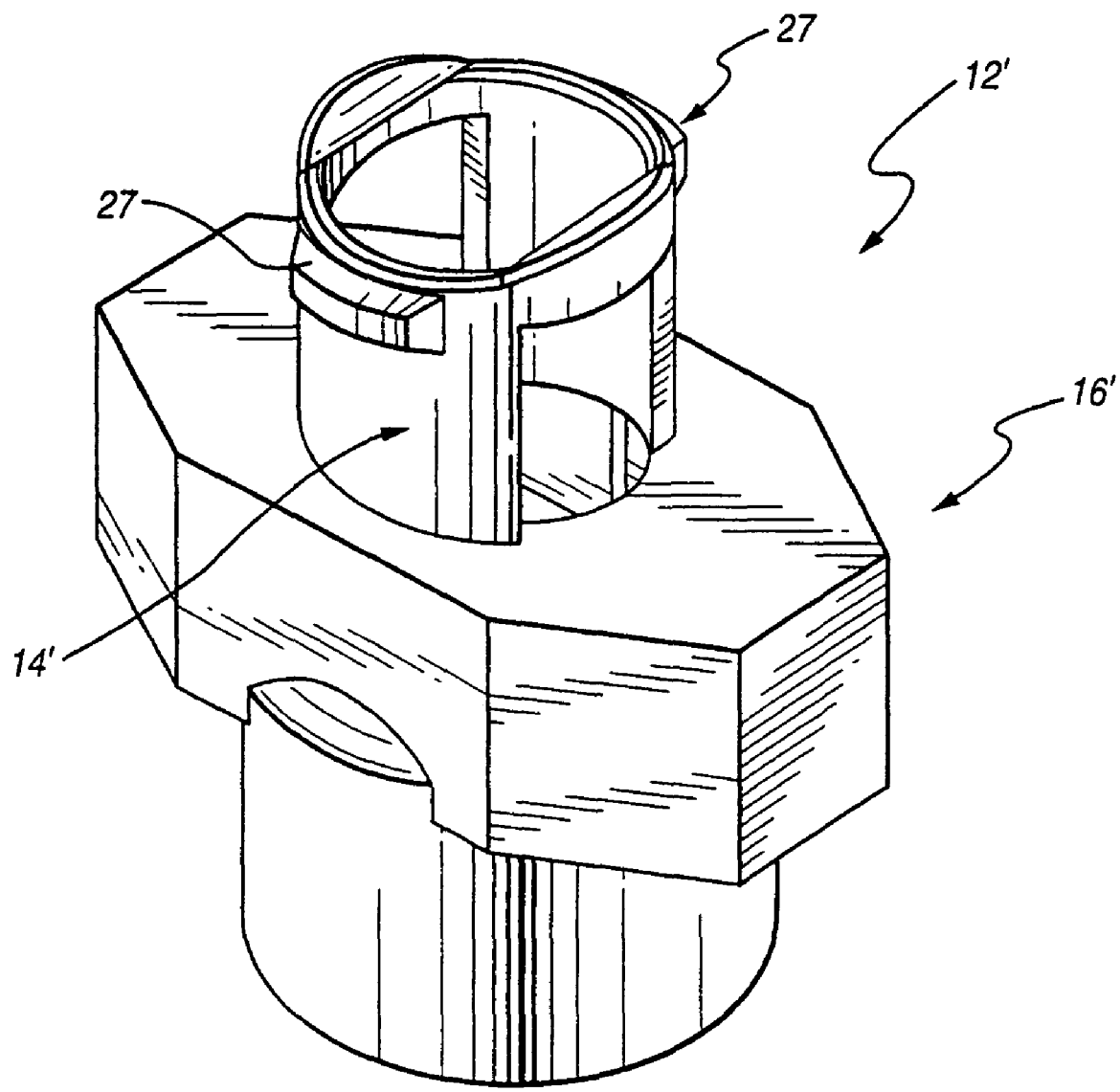
FIG. 4 is a perspective view from above of a variant of the housing of FIGS. 1 and 3.
Figure 8:
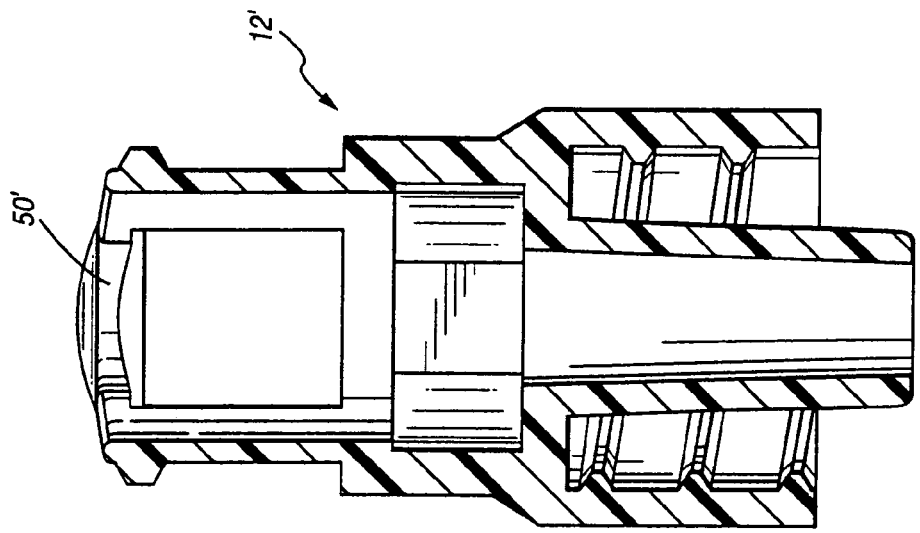
FIG. 8 is a cross-sectional view taken along line 8-8 of FIG. 7.
Figure 7:
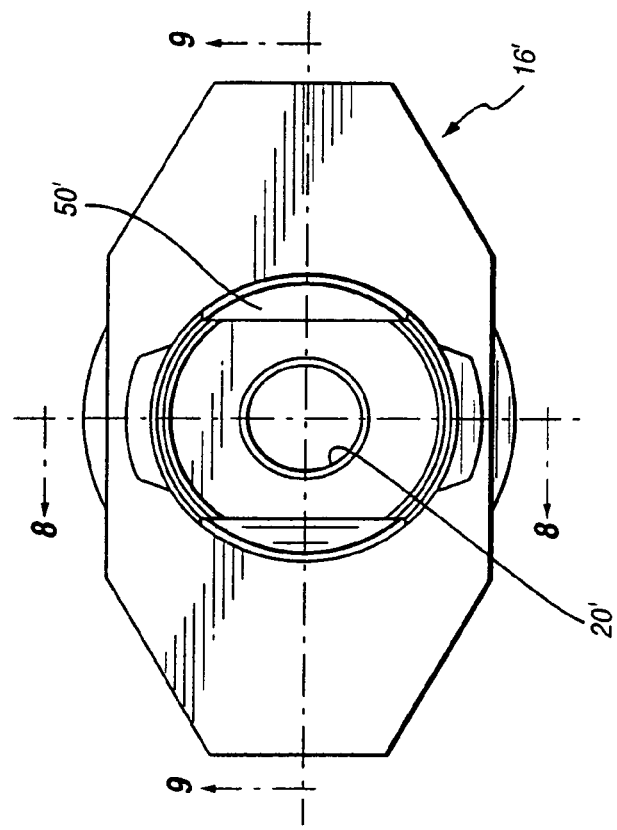
FIG. 7 is a top view of the housing of FIG. 4.
Figure 13:
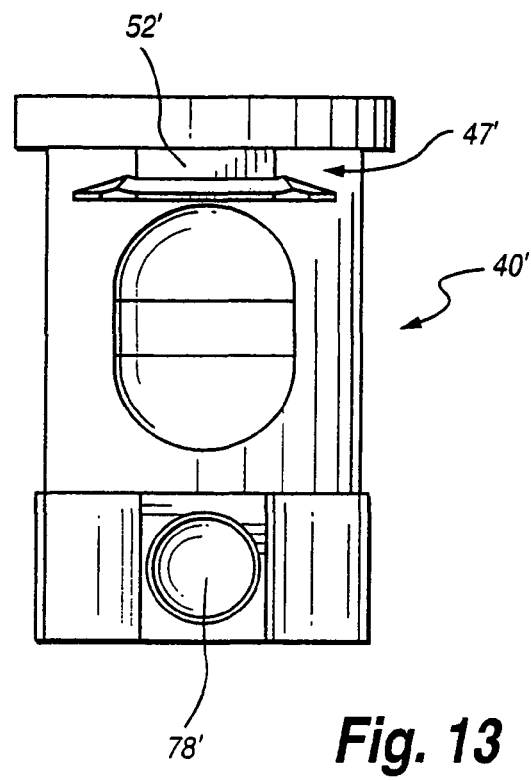
FIG. 13 is an end elevational view of the septum of FIG. 10.
Figure 14:
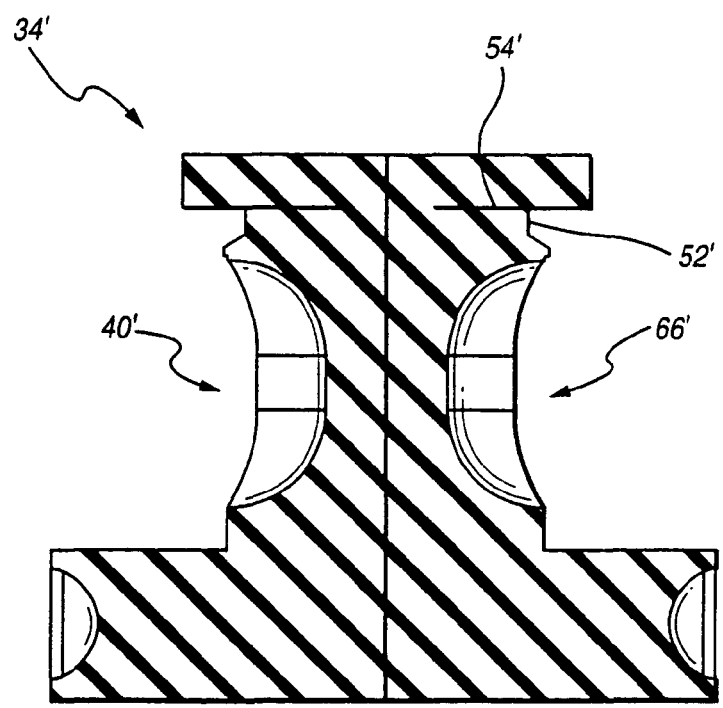
FIG. 14 is a cross-sectional view of the septum of FIG. 12.
Figure 15:
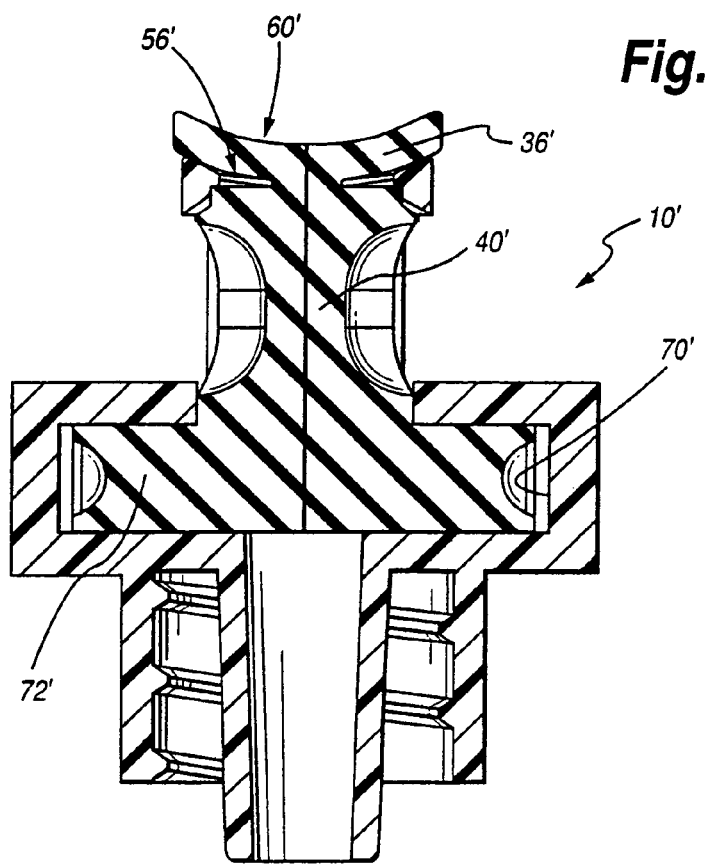
FIG. 15 is a cross-sectional view of the septum of FIGS. 10-14 mounted in the housing of FIGS. 4-9.
Figure 16:
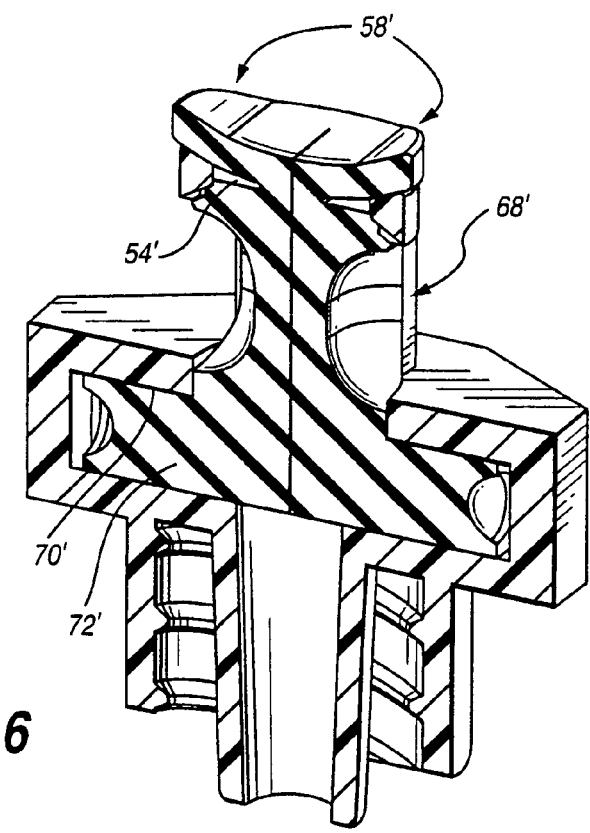
FIG. 16 is a perspective view of the cross-section depicted in FIG. 15.

A rigid floor, e.g. 76, 676, 776 can be provided adjacent the distal end of the septum which further prevents downward deflection of the distal end 72, 672, 772 of the septum 34, 634, 734 during luer tip insertion to further prevent the potential for rebound induced deflection of the distal end of the septum away from the fluid chamber when the luer tip is withdrawn. The floor can have a small central opening for allowing fluid to pass through the floor upon tip advancement; the opening can for example have a diameter equal to that of the flow channel of the luer tip, as shown by way of example in FIGS. 1A and 1C. Note that in the luer receiver 10a of FIG. 1A, the floor 76a of the housing 12" defines an opening having a diameter equal to that of the flow channel of the luer tip. Since downward deflection of the septum 34a is prevented or minimized as aforesaid, the lateral deflection reservoirs 78a of distal septum portion 72a are sized to accommodate the material of the septum distal portion deflected on luer insertion. The luer receiver 10c of FIG. 1C, is also configured so that the floor 76c of the housing 12''' defines an opening having a diameter equal to that of the flow channel of the luer tip. In this embodiment the floor 76c is inclined so as to direct displaced material towards the lateral deflection reservoirs 78c on luer insertion, to prevent or minimize septum 34c downward deflection. Again, the lateral deflection reservoirs 78c of distal septum portion 72c are sized to accommodate the material of the septum distal portion deflected on luer insertion.

The potential for rebound induced deflection of the distal end of the septum away from the fluid chamber when the luer tip is withdrawn can also be minimized by providing a distal duckbill valve sealing member projecting from the distal end of the septum. The duckbill valve minimizes negative fluid deflection since it opens and closes with minimal material displacement and precludes fluid counter flow upon luer withdrawal. An exemplary duckbill valve structure is shown in the luer receiver 10b of FIG. 1B. In this example, the housing 12 is as shown and described with reference to FIG. 1. The distal end portion 72b of the septum 34b is modified, however, so as to define a duckbill valve 43 that will project well beyond the tip of the inserted male luer. This provides a one way (check) valve limiting the flow to a forward direction out of the luer tip and is only open in the presence of fluid pressure from the luer tip. As is apparent, the closure of the duckbill valve upon cessation of fluid flow/pressure precludes fluid flow proximally into the slit of the septum 34b upon luer tip withdrawal and minimizes the potential for rebound induced deflection of the distal end of the septum away from the fluid chamber, thereby reducing or eliminating the negative pressure associated with luer tip withdrawal.

The provision of lateral deflection reservoirs 78 aligned with the slit and the provision of a rigid floor 76 intermediate the septum and the fluid chamber are means to deflect or direct deflection of the septum in a direction away from the fluid chamber during luer tip penetration. It is the combination of isolation of the septum extension from the fluid chamber and focused deflection of the septum away from the fluid chamber which achieves mitigation or elimination of the negative pressure deflection upon withdrawal of the luer tip by preventing elastic deflection of a portion of the septum into the fluid chamber upon advancement of the luer tip.

Figure 53:
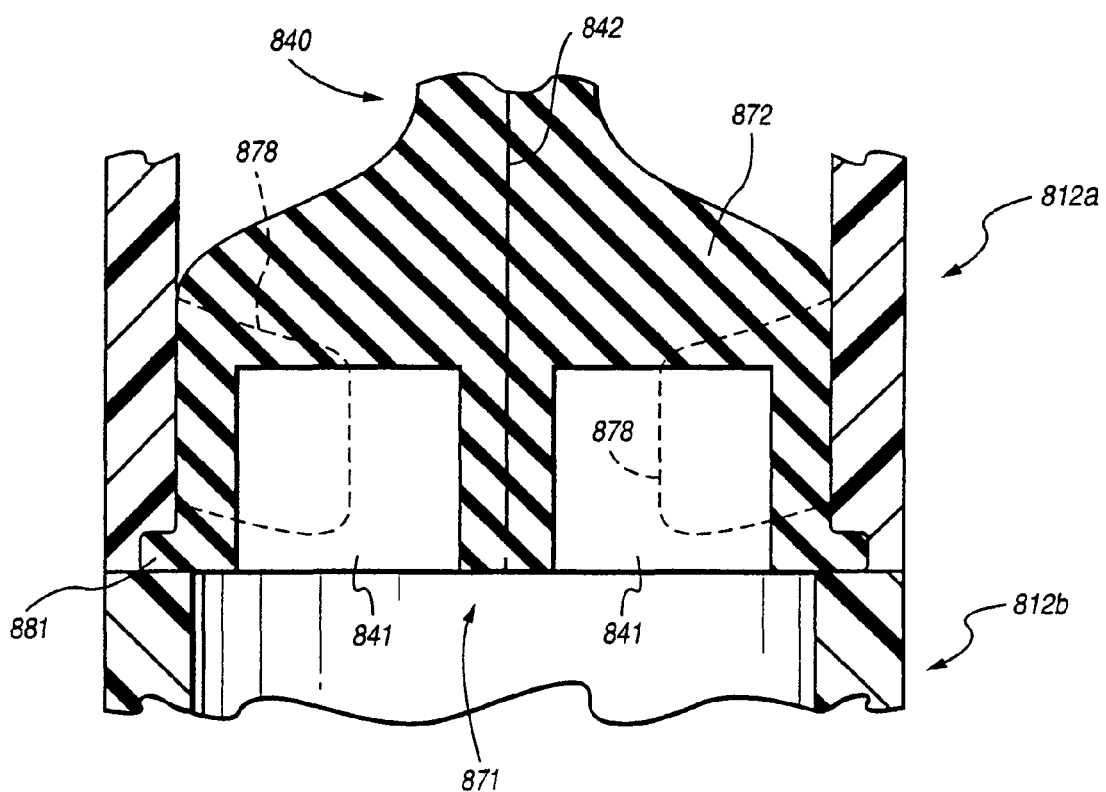
FIG. 53 is a cross-sectional view of a further alternate luer receiver septum embodying the present invention.
Figure 54:
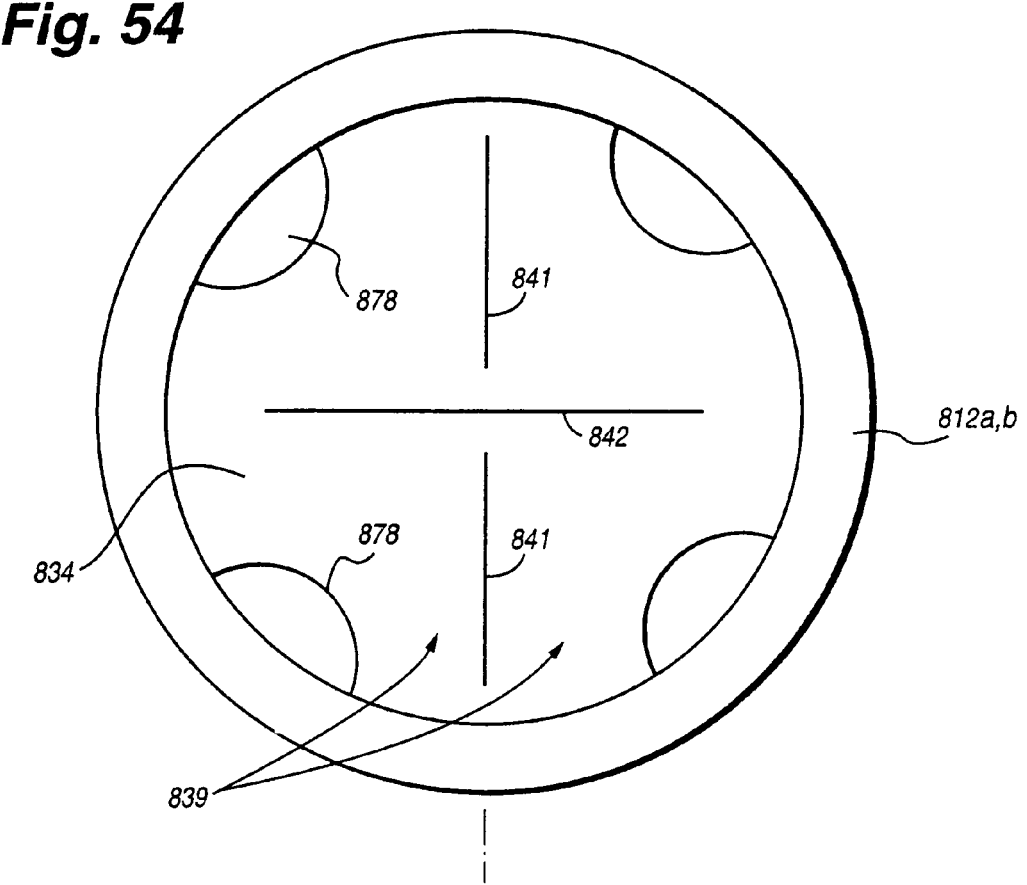
FIG. 54 is a schematic cross-sectional view of the luer receiver septum of FIG. 53, before luer tip insertion.
Figure 55:
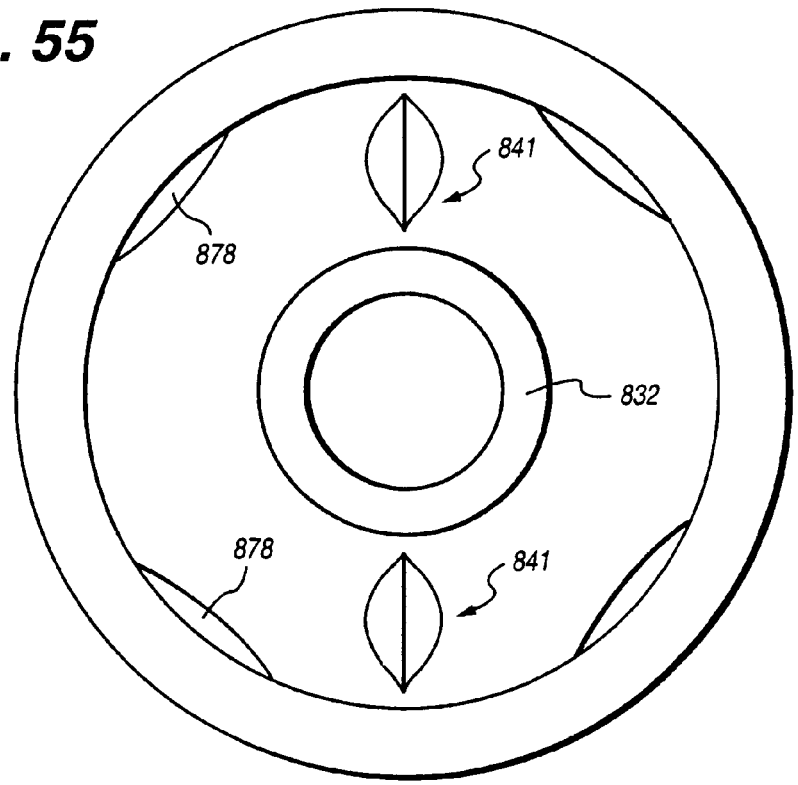
FIG. 55 is a schematic cross-sectional view of the luer receiver septum of FIG. 53, after luer tip insertion.

The septum can be modified to achieve a positive pressure deflection upon withdrawal of the luer tip by providing a portion of the septum which is interfaced with the fluid chamber and which is sized and configured to deflect away from or parallel with the flow chamber such that fluid enters a space adjacent the septum portion upon insertion of the luer tip and then forced back into the fluid chamber or flow channel upon withdrawal of the luer tip. The housing can be configured to divert the lateral deflection of the septum portion into an upward direction and/or the septum portion can be configured to deflect and open laterally adjacent the fluid interface. In one preferred embodiment, shown in FIGS. 53-55, a pair of slits 841 are provided in the distal portion of the septum 834 adjacent the fluid chamber. These are aligned to be perpendicular to the long transverse axis of the slit 842. The slits extend only partially through the septum to define opposing elastomeric columns 839 on each side of and perpendicular to the central slit. In one preferred embodiment the columns 839 are placed under a compression load by compression of the septum 834 against the adjoining lateral housing wall 812. This load is transmitted through the columns 839 to the central slit 842 to more tightly seal the central slit. The load is less than the threshold required to dilate the perpendicular slits 841. In the illustrated embodiment, to further maintain a pre-penetration hermetic seal, the slit 842 is incomplete, leaving a residual membrane 871.

When the luer tip 832 is advanced into the central slit, this places the columns 839 under a greater compressive load thereby deflecting open the perpendicular slits 841. Septum material is also deflected into lower cutouts or slots 878, as shown from a comparison of FIGS. 53 and 55. Substantially full insertion of the luer tip 832 ruptures membrane 871, if provided, while sealing ring 881, captured between housing parts 812a and 812b, maintains a seal about the outer periphery of the septum 834. As the perpendicular slits open during the luer insertion process, fluid will enter the cavities (FIG. 55) formed by the open slits 841. Upon withdrawal of the luer tip, the fluid will be forced back out of the cavities into the fluid chamber as they close. The perpendicular slits 841 can reduce the penetration force required to penetrate through the distal end of the septum by relieving the compressive force during luer tip penetration. In this way a perpendicular compressive force can be applied with a relief mechanism to allow both tight sealing by compression but yet maintain a lower penetration force. Furthermore, the expulsion of the fluid from the cavities upon luer removal reduces or eliminates the negative pressure typically associated with luer tip withdrawal.

Due to the unique features and functionalities of the valve of the resent invention, this valve provides superior infection prevention. Any portal to a patient represents a potential source of entry by the ubiquitous bacteria in the environment. The first consideration of a medical valve positioned at a patient portal site should be its potential to harm the patient by allowing bacterial ingress. Any valve design for access to a patient should be thoughtfully considered relevant its inherent potential (or the limitation thereof to reduce bacterial ingress at the portal site. Only if the valve does not pose an increased threat to the patient should its safety to healthcare workers be considered an advantage and the ideal valve should reduce the threat when compared with the gold standard traditional reseals which have been used for over two decades. Yet healthcare worker safety has been the recent focus of proposed legislation in California and elsewhere, in the rush to enhance the safety of healthcare workers the potential risk that more complex piston valves pose to certain vulnerable patient groups has been overlooked.

There is growing evidence that, while the new needle-less IV access systems in general are safer for the health care worker, they may be associated with an increase risk for the patient, especially a patient with a weak immune system, such as for example a breast cancer patient who has received chemotherapy or a bone marrow transplant. Since these patients have a low white blood cell count for defense against bacteria they are vulnerable to even low numbers of bacteria which may be introduced into the body through an artificial portal such as a IV access site. This is also true of transplant patients or patients with leaking heart valves or indwelling prosthetic valves or devices. In these patients, even a few bacteria introduced into the bloodstream can colonize the valve or device because the patient's defenses are not very active at the site of the artificial prosthesis or leaking valve. These important microbiologic considerations have been largely overlooked in the rush to make the transition from traditional IV systems which used needle penetration of elastomeric septa for access to the more mechanically complex, piston based needle-less systems widely used in the present art. The old traditional reseal systems were simple septa for receiving a sterile needle, they lacking moving parts and could be easily prepped over their entire upper face. The process was mechanically simple and similar to penetrating a needle into prepped skin. These simple reseals had no exposed internal pistoning parts which could be colonized about the exterior boundary of the bore of the housing as is present with several conventional luer access devices.

The present invention serves to overcome the problems of increased risk of patient infection while still providing complete protection for the healthcare worker. It is the purpose of the present invention to provide an enhanced barrier to prevent bacteriologic ingress and invasion at a patient access portal such as an IV terminal. The present inventor uses the term Patient Protection Portal "PPP" to emphasize that the present invention is designed to achieve enhanced barrier protection for the patient as well as providing healthcare worker safety.

One important mechanism to prevent bacterial ingress is the provision of a tightly sealed slit. The present invention provides sealing at plurality of levels of the slit and preferably provides compression to induce sealing of the slit along at least two levels of the slit. The present invention further provides a tight seal between the septum and the flow channel. Preferably this seal seals the outer perimeter of the extension against migration of fluid or air into or out of the fluid chamber about the outer perimeter. This seal can be provided by compression between the housing and the septum. The compression is preferably provided circumferentially about the housing. In this way the flow chamber is sealed from the outside environment at three levels, the upper face, the lower interface with the fluid chamber and about the perimeter of the septum. In one preferred embodiment a fourth area of sealing is provided immediately below the upper surface of the septum by focused compression below the "wedged closed" slit-surface interface. Further in one presently preferred embodiment a fifth sealing point is included with the addition of a duckbill valve at the end of the septum.

The enhanced sealing afforded by the high contact mass allows the valve to be incorporated into a wide range of medical devices wherein leakage about the shaft associated with a high back pressure or a high internal vacuum is prevented by the higher mass of the contacting septum as well as the higher contacting surface area of the septum along the slit which is facilitated by the long length of the slit. These devices include, for example, vacuum filled blood collectors, high pressure injection systems such as those used for contrast injection during radiographic procedures including angiography, and drug vials. It is highly desirable to provide luer lock access to hermetically sealed drug vials. However, while drug vials do not normally have a high resting internal pressure, the injection of diluent into a closed vial can be associated with the development of markedly high back pressures and leakage around the shaft and associated aerosolization of drug must be prevented during such a maneuver by tight sealing about the shaft of the indwelling luer tip.

As noted supra, this valve is intended for universal use. For this purpose the valve can be constructed as a cap with an upper housing portion, such as upper housing portion 612a, described with reference to FIGS. 26-40, containing the septum, e.g. 634, mounted on the proximal end of an open or closed chamber for storing or flowing fluid. Alternatively the septum can be inserted into an integral housing which includes both the upper housing which holds the septum and the lower housing which comprises the flow channel or fluid chamber. FIGS. 56-59 show examples to the adaptability of the invention to various containers and flow systems. In some environments, such as mounting on a blood tube 603 (such as a hemodialysis blood tube), the cap portion 612a containing the septum 634 is all that is required with the blood tube 603 providing the lower chamber or flow channel. A similar configuration can be seen with an IV bag 601 where the cap 612a, 634 is mounted to the bag for luer access to the bag comprising the fluid chamber.

FIG. 59 shows a blood or specimen collector 604 designed to receive a sharp needle, blunt cannula, luer slip connector, or luer lock connector. The container is preferably comprised of shatterproof plastic as is known in the art. The collector includes a luer-receiving valve, which defines a container cap, for example of the type provided by upper housing portion 612a and septum 634. The cap thus includes a housing 612a, which is preferably rigid, and an elastomeric portion 634 having a central slit mounted with the housing. The cap further includes an upper surface adjacent the proximal end and a distal end. The cap is sized to be bonded adjacent the open distal end of the receptacle and to occlude the distal end of the receptacle.

The diameters of many conventional adult blood collection containers are larger than that of conventional female luer lock end. For this reason the receptacle can have a reduced diameter at the proximal open end of the receptacle. Alternatively the housing of the cap may be adapted to provide a larger internal or outside diameter to engage the larger diameter adult tubes. The cap may be joined with the collection tube by intussusepting one of the cap and the open distal end of the receptacle into the other or by otherwise mounting the cap adjacent the distal end. A compression seal may be provided about the open proximal end of the blood collecting tube and the septum portion of the cap. It is preferable to minimize cost to have a single mold for septa which can be used for capping vacuum filled containers, drug vials, Y-sites, saline wells, catheter terminals, stopcocks, manifolds, intrauterine and intracranial pressure monitoring devices, and blood tubing ports. This can be achieved by using a single configuration for the upper portion of the housing adjacent the septum. The many diverse housing and flow channel structure below the septum can be adapted to accommodate and seal with the septum in the cap. In this way hospital personnel will always see a standard connection terminal, and will understand its function, and compatibilities. Also the process of designing and testing many different new molded configurations of septa for different applications is avoided. Indeed a breakaway membrane discussed supra, can be included as part of the standard septum design.

In operation the luer tip is inserted through the slit into the receptacle. The specimen is transferred into the receptacle and the luer tip is withdrawn, the septum automatically seals upon withdrawal of the luer tip.

It is advantageous for any standard receptacle used to collect blood, whether a rigid tube or flexible bag to have an interface for a luer lock connector. This is because blood is often initially collected from catheters using a syringe. If the syringe uses a luer slip, the tip can slip out of the catheter terminal potentially resulting in a blood spill potentially exposing the nurse or physician to blood. This is particularly true because the nurse or physician is pulling back on the plunger of a syringe to collect the blood. This pull can cause the luer slip to pop out. If the connection is arterial, as with a left heart catheter, blood can spurt out if the luer slip comes out of the terminal. In addition to aforementioned problems on the initial collection side, the luer slip also does not allow for optimal alignment of the luer slip with the collection container itself and the luer slip is also vulnerable to slipping out of the blood collection container. In addition, luer slip syringes are not in wide use in many parts of the hospital and therefore may not be readily available for blood collection as in an emergency. It is the elimination of incompatibility, which is one of the purposes of the present invention. For these reasons, the blood collector of the present invention allows for compatibility with luer lock connector, luer slip connectors, blunt cannulae, and sharp needles. It is intended that this functionality be universally available for virtually all connections or interfaces in the hospital environment.

When the valve is incorporated into vacuum filled containers 604 or other closed receptacles, e.g. a drug vial 602, which contain a pharmaceutical, diluent, or IV solution for example, the septum must be hermetically sealed for long term storage as by an unperforated membranous seal adjacent a portion of the slit. It is preferable that this seal be homogenous with the septum so that expense can be minimized. In one preferred embodiment discussed supra this was provided by assuring that the central slit was an incomplete slit, the slit extending only partway through the septum to a point adjacent one end of the septum (See reference numeral 71 in FIG. 1). A sharp projection, which may be mounted with the housing, can be provided to cut or otherwise disrupt the membrane to open the passage to the receptacle through the slit. Alternatively the septum and membrane can be configured such that the membrane tears open with a low penetration force so that even a blunt luer tip easily separates the hermetic seal so that the expense and molding considerations associated with a sharp disruption projection are not required. One method of achieving this includes the application of a thin elastomeric plug or coating to the septum, as to the upper septum surface, which is penetrated on the first penetration by the luer tip, as described below with reference to FIGS. 64 and 65. This plug can be comprised of silicone have a low tear resistance (as is known in the art) and easily torn. The plug can be slightly slitted at its upper or lower surface to facilitate tearing upon stretching of the plug.

Since the luer tip is very blunt, the large diameter of the tip would normally be seen as a disadvantage making the penetration force though an unperformed membranous seal more difficult. For this reason the present invention achieves the feature of tearing with a low penetration force by actually exploiting the relatively large diameter of the luer tip to achieve mechanical advantage for membrane tearing. More specifically, the present invention uses the large diameter of the luer tip in combination with strategically placed septum cutouts and or slits, to maximally spread apart the elastomer in a focused region adjacent a weakened portion of the membrane so that the seal will tear open. To facilitate this the elastomeric membrane across the slit is positioned along the slit such that the luer tip engages or transmits substantial stress to a specific region of the membrane. Using strategically placed cutouts is one means to predetermine the region to which the stress is focused since, as discussed supra, they can define the region of the septum, which is maximally stretched by deflection into the cutouts. By weakening a portion of this region ease of forceful disruption upon luer advancement is optimized and the stretching of the membrane and its disruption can be focused to a small region to minimize the penetration force required to achieve disruption. In one embodiment the slit terminates in an oblique membranous seal which can be formed by slitting the septum to a point adjacent the end of the septum wherein the septum distal end provides a parallel oblique projection. The short membranous segment remains unslitted and provides a hermetic seal. The slit therefore ends in a blind pouch obliquely oriented with respect to the face wherein the configuration of the end of the pouch is such that the luer tip engages the upper portion of the sealing membrane and stretches the upper end until it tears. The tear is then continued along the oblique membrane as the luer tip is further advanced. Additional weakening slits extending partially into the septum adjacent the membrane can be provided (as described above with reference to FIGS. 53-54) to additionally weaken the membrane against transverse stretching.

For both the penetration and activation designs the configurations discussed supra eliminate deadspace. This is most important if the valve is intended for bi-directional flow wherein blood withdrawal through the valve is a desired function or wherein blood or plasma is to be administered through the valve. Blood, because of its viscosity and the adherent properties of the fibrin, plasma proteins and red blood cells has the potential of sticking within deadspace and may be difficult to wash from these areas. Also, when used with blood conserving arterial lines or with hemodialysis lines for blood withdrawal it is important not to have any deadspace within the valve structure flow path or between the valve structure and the flow channel of the line since this will require the withdrawal of a prior discard sample before withdrawal of a blood sample for testing. As in the present invention, the limitation of flow to the central flow path and/or the provision of deadspace displacement material within any resting deadspace which interfaces with medical fluid during operation, addresses these issues.

If preferred other features can be added to enhance functionality. A feature which can be included is the provision of an incomplete slit at distal end of the septum (as providing a residual membranous closure 71 across the slit 42 where it would otherwise directly contact the flow channel 20 in the embodiment of FIG. 1). This allows the device to be used in situations wherein absolute sealed closure must be maintained prior to first penetration. To provide ease of disruption of the membrane it may be weakened in an axis parallel to the slit or a sharp member may be provided adjacent the membrane which contacts the membrane upon downward deflection of the septum.

Figure 60:
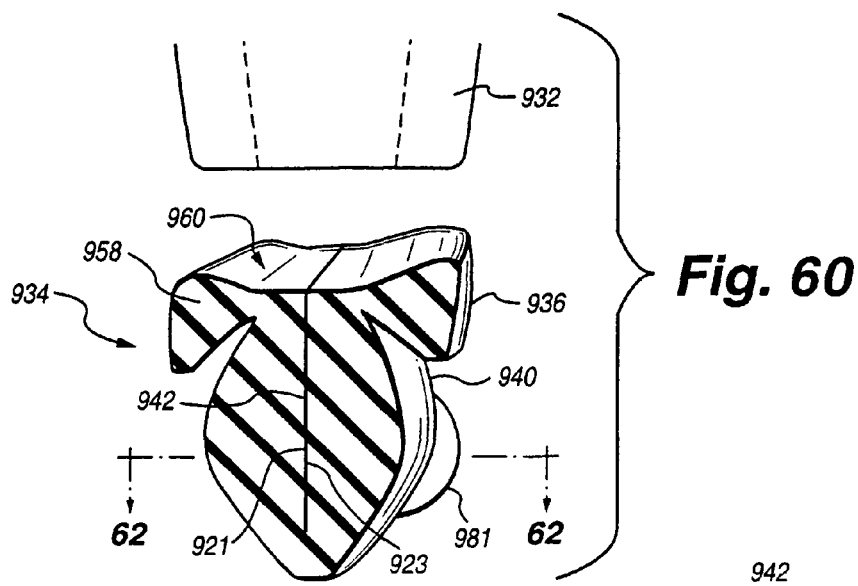
FIG. 60 shows a male luer tip and a septum in accordance with a further alternate embodiment of the invention.

FIGS. 60-63 show a luer receiving valve embodiment intended for luer activation of the valve mechanism induced by downward deflection of a septum and the application of a compressive force against at least one wall of a septum to open a central perforation or slit through the septum rather than by luer tip penetration into the septum as shown in the previous embodiments. The use of compressive force and contact members to open a central slit through a septum is discussed in U.S. Pat. Nos. 5,549,651 and 5,697,915 (the disclosures of both of these patents are included herein by this reference as if completely disclosed herein) which provide background for the present invention. As disclosed in the aforementioned patents the slit can be aligned centrally within the septum and the application of compression against the wall of an elastomeric septum wall can include compression against an internal septum wall, which will deflect the opposing walls of the slit apart along the same axis as the compressive force. Alternatively compression can be applied against an external wall which will deflect the opposing walls of the slit apart in an axis perpendicular or oblique to the axis of the compressive force. Generally, FIG. 60 shows a luer receiver wherein the septum is pressed against a contact member by forceful pressure of the male luer tip against the outer face of the septum. The septum is thereby squeezed such that compressive force is applied against the septum from two opposing directions both applying a compressive force along the longitudinal axis of the septum to deflect the slit into an open position along its entire length.

Figure 63:
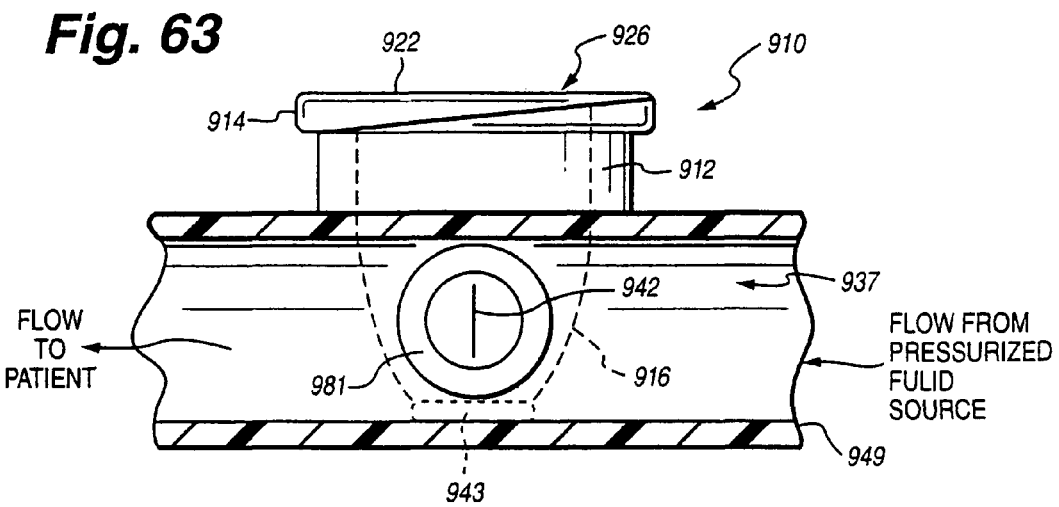
FIG. 63 is a schematic part cross-section view of a luer receiver for receiving the septum of FIGS. 60-62.

The luer receiver 910 includes housing 912 and an elastomeric septum 934 with an elastomeric distal extension 940 mounted within the housing 912. The housing includes an outlet 922 and a main cylindrical bore 926. The septum 934 includes a cylindrical portion 936 sized to slideably advance along and seal about the main bore 926. The septum 934 includes a slit 942 and an outer face 960 with opposing elevations 958 aligned with the long axis of slit 942. Opposing flexion recesses 954 are provided parallel to the long transverse axis of the slit, which allow the face 960 to flex upon forceful contact as will be discussed. The recesses 954 and indeed other portions of the receiver 910 intermediate the housing 912 and the extension 940 may be filled with a deadspace filler (not shown) with a high resting volume but a low compressed volume (such as medical foam rubber) to eliminate any resting deadspace within the housing 912. The slit 942 defines opposing internal walls 921 and 923 which are closed when the septum is mounted in its resting position with the outer face 960 positioned adjacent the proximal end 914 of the housing 912. The slit 942 exits the side of extension 940 surrounded by gasket 981, which is sized to be sealingly received in flow, channel wall 916. The slit 942 exits at the side of extension 940 into the flow channel 937. The slit 942 divides the extension 940 into sides 939 and 941 which alternatively can be thinned laterally (for example to define concave outer walls as for the extension of FIG. 1) to provide easier lateral deflection and reduced resistance to compression. Thinner walls can, for example, be used when a higher durometer (such as 40) silicone is used in manufacture. The luer receiver 910 includes distal contact members 943 at the end of the bore 926 and projecting toward the bore 926. In operation, as the luer tip 932 (FIG. 60) is pressed against the face 960 of the septum 934, the elevations 958 are pushed downward deflecting the face 960 of septum 934 to a greater extent parallel to the long axis of the slit 934 than perpendicular to said axis thereby flexing the face and biasing the upper portion of the walls 921 and 923 apart to open the slit 942 adjacent the face 960. The distal contact member 943 is positioned such that when the male luer 932 advances the septum 934 along the bore 926 against the distal contact member 943, the distal contact member 943 deflects the lower portion of the walls 921 and 923 apart such that the slit is opened along its entire length. The septum 934 is relatively soft and elastic and can be of elastic silicone having a durometer of about 20-40 so that the septum will easily compress against the distal contact member 943 but will rebound after being released. The order of closing along the slit 942 is reversed relative to the order of opening when the septum 942 rebounds to its proximal resting position so that the proximal portion closes first when the pressure is removed from the elevations 958. Thereby deflecting any residual fluid in the slit 942 toward the flow channel 637 to mitigate and indeed eliminate negative fluid pressure deflection within the flow channel 937 upon rebound of the septum 934. It can be seen that the slit 942 opens to the side of septum extension 940. This allows for dead space free mounting access in a side arm configuration as shown in FIG. 63 with the slit 942 exiting the side of the extension 940 directly into the flow channel 947 of tube 949.

Figure 62:
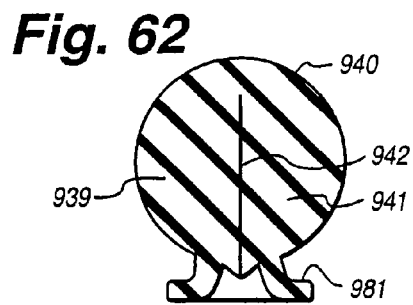
FIG. 62 is a view taken along line 62-62 in FIG. 60.
Figure 61:
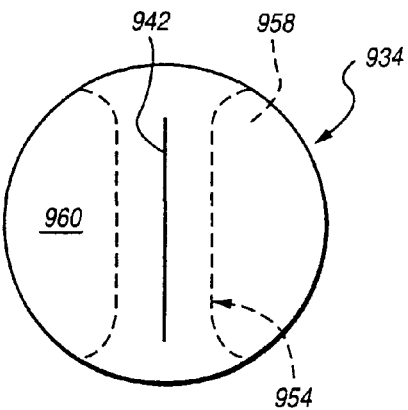
FIG. 61 is a plan view of the septum of FIG. 60.
Figure 64:
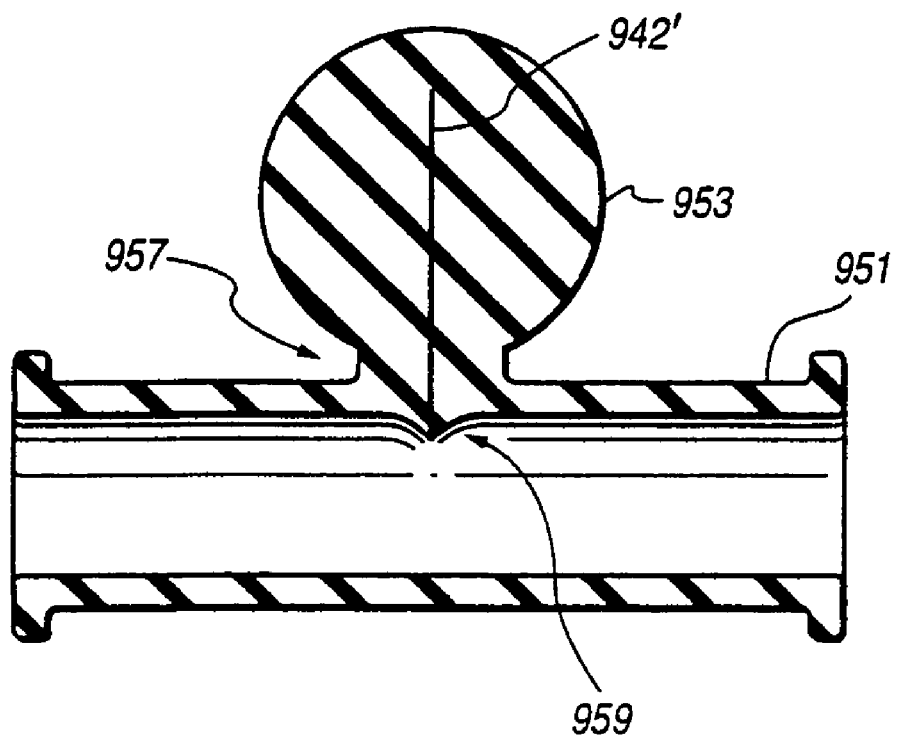
FIG. 64 shows a modification of the septum shown in FIG. 62.

FIG. 64 shows a modification of the gasket 981 shown in FIG. 62 to provide an extended gasket molded as an integral elastomeric tube 951 molded with the side of extension 953, the port exiting into the tube 951. This tube 951 is intended for intussuseption and sealing with a flow channel housing 949 of the type shown in FIG. 63 (not shown in FIG. 64) and can be encased with or otherwise surrounded by the flow channel housing 916. If preferred a rigid coupling, not shown, can be used to secure with the tube 951 at both ends. If the tube is encased within an outer tube, the encasement can for example be comprised of rigid polycarbonate or similar plastic, which is integral with a septum housing, e.g., 912. With the embodiment shown in FIG. 64 the slit 942' extends directly from the atmospheric face of the elastomeric septum to the side mounted flow channel within the integral elastomeric tube 951 thereby passing through and being completely enclosed and sealed within a single molded elastomeric structure thereby providing simplified manufacture. With this embodiment, a short neck 957 can be provided to project the exit port 959 and its enclosed slit 942' laterally toward a slightly more laterally positioned tube 951 and compression can be applied to the neck perpendicular to the slit 942' to distally seal the slit 942' in the neck when the luer tip is not advanced against the septum. This embodiment may be modified to achieve opening adjacent the atmospheric interface during advancement of the septum by the use of opposing laterally projection cams as shown for the preferred embodiment of U.S. Pat. No. 5,549,651 in the place of the mechanism of downward facial flexion discussed supra.

Although not shown, a similar side mounted gasket or sealing tube configuration can be used with the luer penetration receiver to provide deadspace free side arm mounting of the septum with a simplified one piece silicone septum-tube configuration. With this type of design the port can be a lateral projection of the extension of the type shown in FIG. 1. The port preferably projects about the slit and extends in an axis perpendicular to the cutouts of the extension. The slit narrows distally to limit the distal advancement to the luer to a point just above or adjacent the port so that upon advancement of the luer tip the luer tip remains vertical but the nascent open flow path which is wedged open by the luer tip turns to an obliquely or perpendicularly positioned open port. With such a design the neck (if provided) is preferably only a few millimeters or less in length so that the slit extending through the port is wedged open into the flow channel when the luer tip is advanced into the extension. The rigid housing can be simply the housing about the upper portion and extension of the septum as shown in FIG. 1 but wherein the housing ends distally with a circumferential or nearly circumferential mounting about the neck adjacent the port. Alternatively the housing can be joined with or be molded with a casing of the type discussed supra mounted about the side mounted tube. The housing, which can include slots as shown in FIG. 1, can be mounted to the entire one piece receiver which includes the silicone tubing and septum structure to provide rigidity for threading the luer lock about the proximal end of the septum and to provide focal compression in narrow regions (for example regions having a length of 1-3 mm.) adjacent the proximal end and adjacent the neck. Adjacent both compression regions, the housing and the receiver are sized and configured to provide compression in a vector perpendicular to the slit as it extends from the atmospheric interface to exit laterally at the port projecting from the extension into the integral tube.

Figure 65:
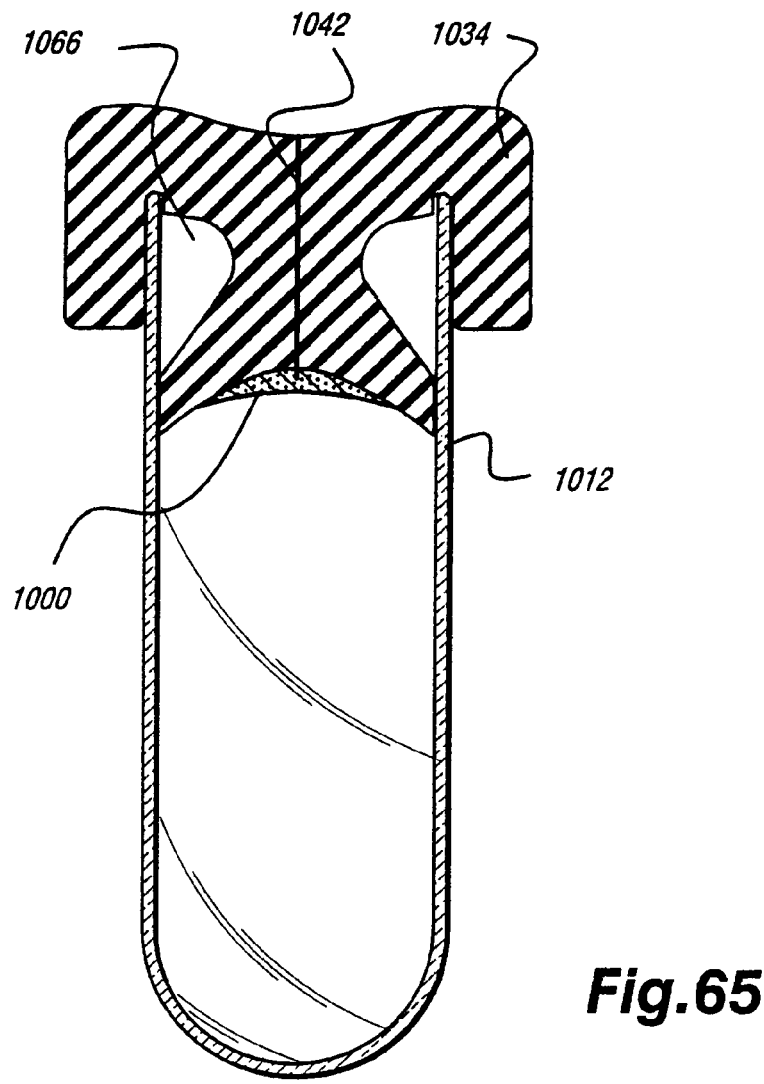
FIG. 65 shows a cross-section of a blood collector and septum in accordance with yet a further feature of the invention.
Figure 66:
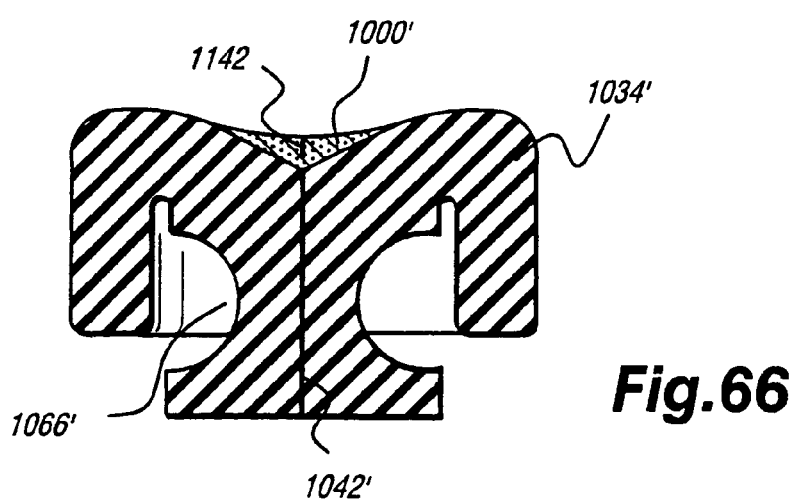
FIG. 66 shows a cross-section of a further embodiment of the septum of FIG. 65.

FIGS. 65 and 66 show, as a further embodiment of the invention, a blood collector and septum structures for use with a male luer. The collector has an open ended housing 1012 and a septum 1034 mounted with the housing 1012 and occluding the housing. The housing contents are preferably under vacuum, maintained by the sealing septum. Lateral cutouts 1066, 1066 are provided to focus the deflection of the septum. An elastomeric plug 1000, 1000', such as a silicone plug having a low tear resistance, is provided adjacent at least one end of the slit 1042, 1042'.

In the embodiment of FIG. 65, the slit 1042 is made after the plug 1000 has been bonded to the septum 1034. In the embodiment of FIG. 66, the septum 1034' is slitted (or molded with a preformed slit) and then the plug 1000' is bonded thereto and a second slit 1142 is made in the plug at the surface, to facilitate subsequent luer penetration. If preferred, the septum and plug can be initially molded together as a single unit of two silicone members and then slitted or they can be molded with the slits in place as desired. It is preferable that the septum have a high tear resistance as is conventional for the septa of blood collectors. The plug on the other hand is preferably comprised of silicone with a low tear resistance so that the partial slit through the plug is easily extended through the plug by the splitting effect of the large diameter male luer tip.

Figure 67:
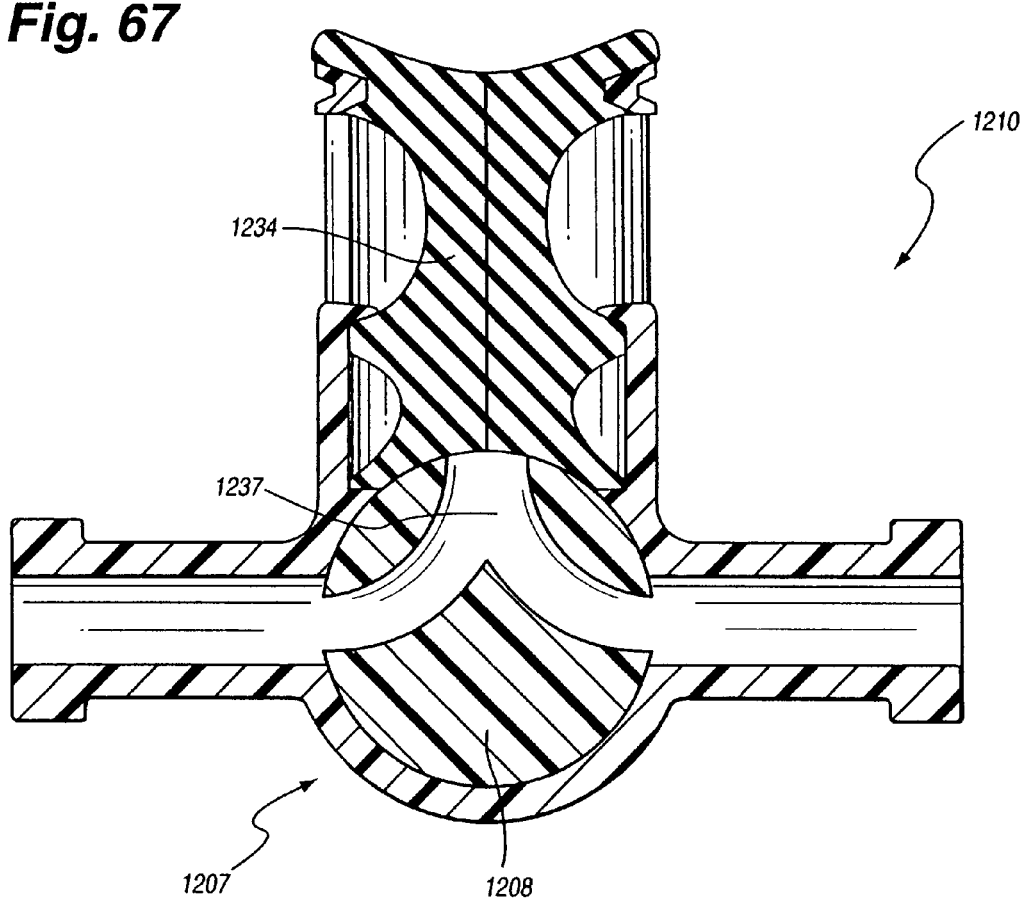
FIG. 67 is a schematic cross-section of a minimal deadspace stopcock with luer receiver in accordance with the invention.
Figure 68:
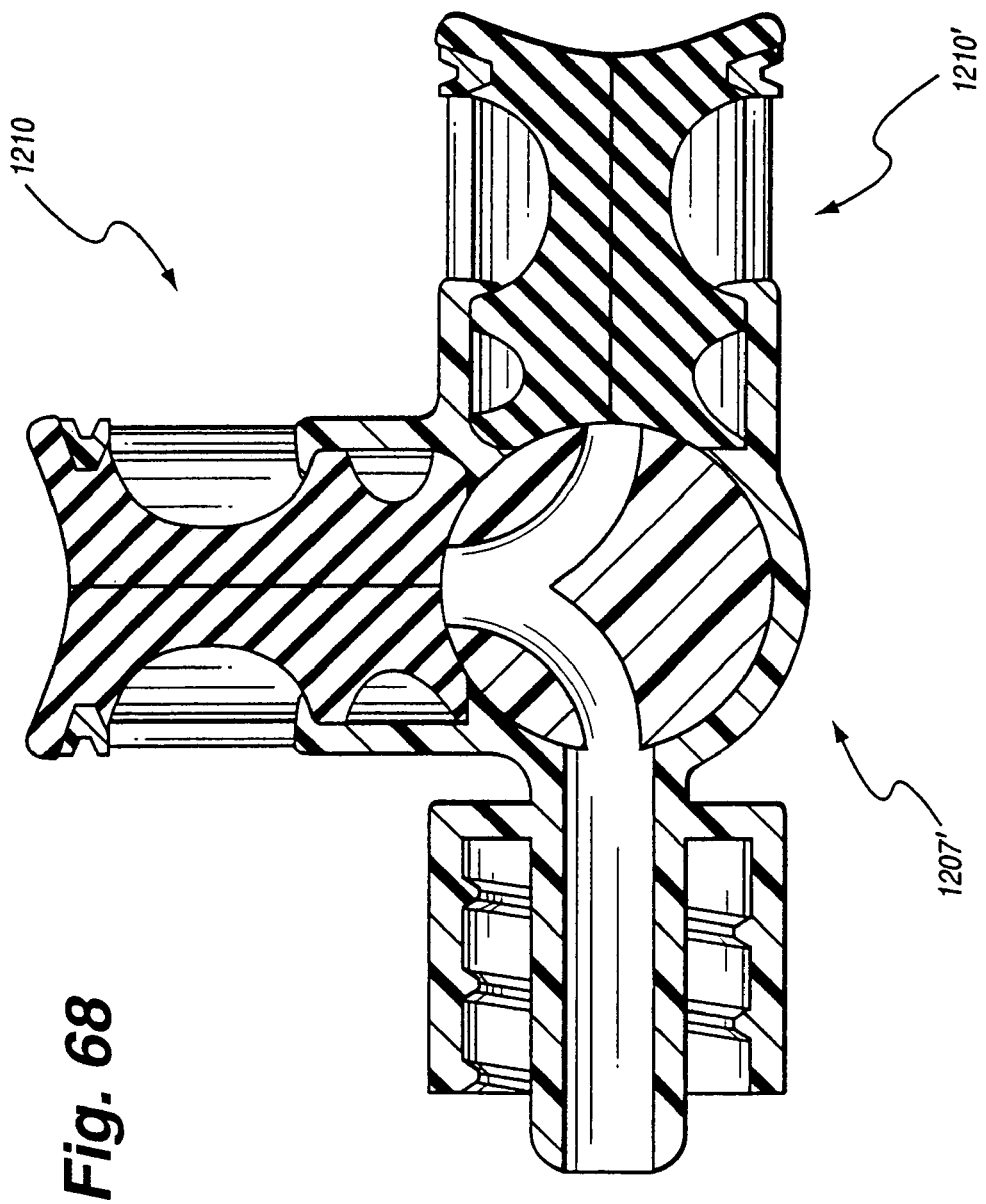
FIG. 68 is a schematic cross-section of another minimal deadspace stopcock having two luer receivers in accordance with the invention.

The medical valve of the instant invention can be applied to achieve a minimal dead space configuration at both the upper atmospheric surface and the fluid interface. This allows blood sampling without the collection of blood within the fluid chamber below the septum. An embodiment of a luer receiver 1210 integrated with a minimal deadspace stopcock 1207 is shown by way of example in FIG. 67. The stopcock 1207 has a ramped flow channel 1237 provided within the central rotating member 1208 of the stopcock below the septum 1234 to further allow ease of displacement of any residual blood from below the septum. Another embodiment, shown in FIG. 68 includes a plurality of valves 1210' mounted on the stopcock 1207'.

The present invention further allows the application of a universal safety feature for medical connection. The disconnection of medical devices represents an inherent risk to patients in the present conventional art, and the FDA has identified this risk. The FDA recommends checking connections for security but regrettably the luer lock connection, despite its name, is a simple threaded connection with the inherent potential for unwanted disconnection at any time. Such unintentional disconnection can result in bleeding, air embolism, etc. which can be silent (as when the patient is sleeping) and can result in death. The present invention, by its universal applicability and functionality and further as a function of its inherently low manufacturing cost, makes possible a new standard of patient luer connection, whereby any proximal terminal of a tubing system or catheter would be closed by an integrally attached "valve" defined by a luer receiver. The integration of the luer receiver/valve of the present invention into the terminal of catheters further eliminates the potential that unwanted disconnection can occur at the catheter site (one of the more common disconnect sites). This provides for the complete elimination of the potential for disconnect-related morbidity and death. The new standard will be "NO OPEN DISCONNECT". This is a matter of safety for both healthcare workers as well as patients since any bleeding through a disconnect creates an OSHA "blood-spill" which represents a threat to the laundry service, housekeeping, and to the nurses or physicians correcting the matter. FIG. 69 shows a catheter 1312 with an integral luer receiver 1310 at the proximal terminal and a second luer receiver 1310' for piggyback connection extending from one side. FIG. 70 shows a safe "no open disconnect" IV tubing system 1412 having a luer receiver 1410 provided in accordance with the invention at the proximal end, and a luer lock end 1418 at the distal end. This system is designed to assure that any inadvertent disconnect does not pose an open communication risk to the patient.

Figure 71:
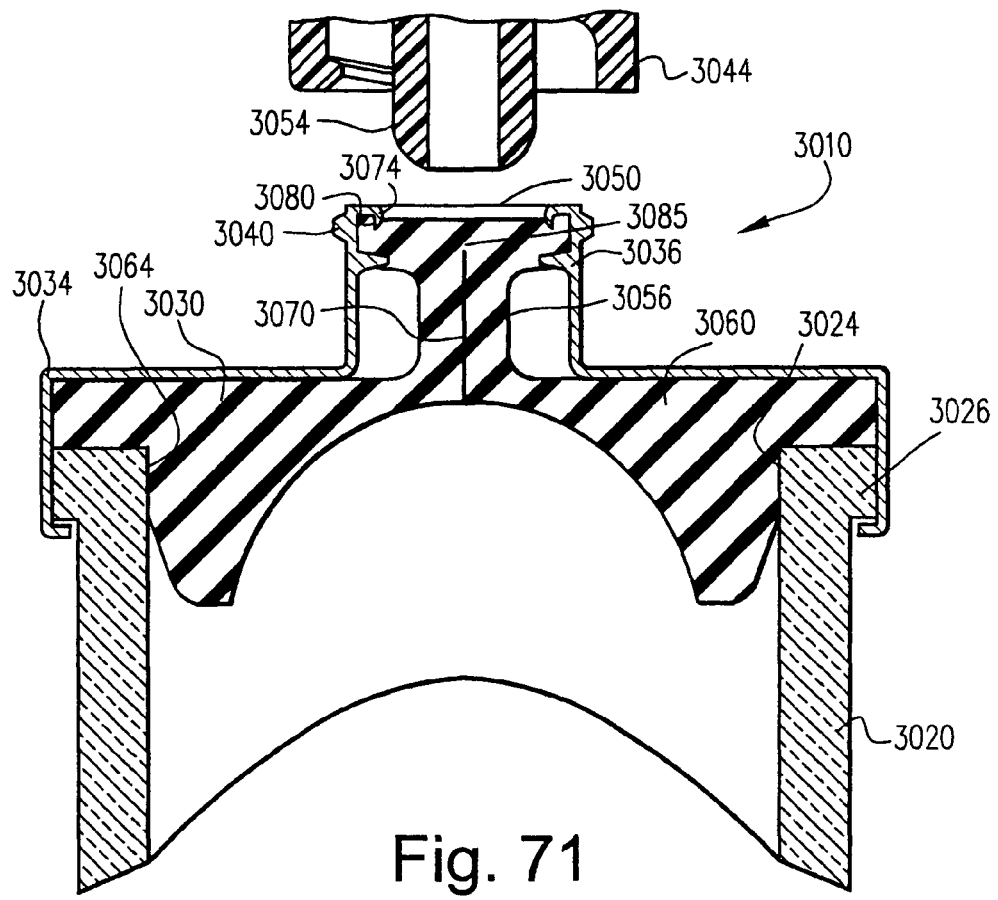
FIG. 71 is a broken, half-section view of the luer access container according to the present invention.

Referring to FIG. 71, the luer access container 3010 includes a receptacle 3020, which is comprised of glass or shatterproof plastic, having an open end 3024 and projections 3026 for engaging a stopper 3030 within the open end 3024. A retainer 3034, which is preferably of metal or rigid plastic, is provided to hold the stopper 3030 in place. The retainer 3034 includes a luer receiver 3036 with lugs 3040 for receiving the threaded luer lock member 3044. Alternatively threads can be provided. The stopper 3030 includes an upper face 3050 for receiving the luer tip 3054, a central downward projection 3056, and a lower portion 3060 for engaging the wall 3064 of the receptacle 3020 adjacent the open end 3024. A slit 3070 is provided extending partially through the stopper 3030. The retainer 3034 includes downward projecting edges 3074 that fit into a circumferential slot 3080 about the face 3050. The edges 3074 can be swaged onto the stopper face 3050 to hold the face 3050 tightly in place. The slit 3070 ends in a membranous cover 3085 at the face.

Figure 72:
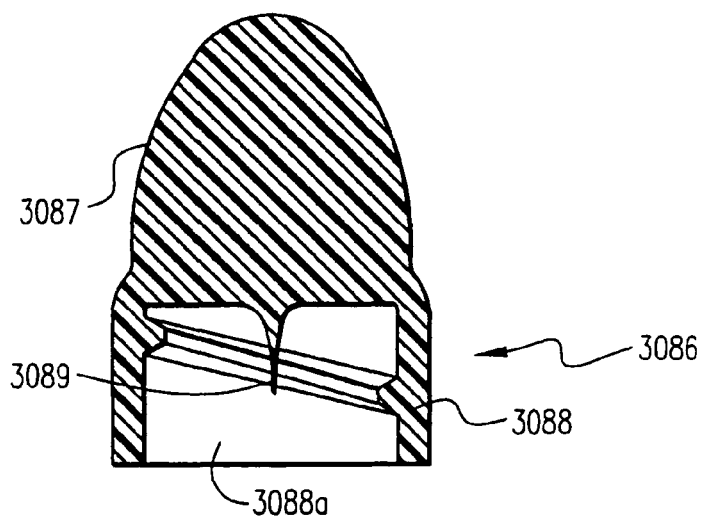
FIG. 72 is a half-section view drawn through line 72-72 of FIG. 75 of the membrane-perforating cap.
Figure 74:
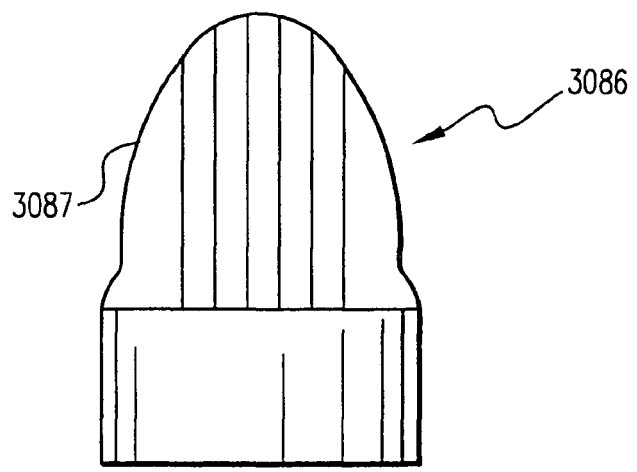
FIG. 74 is a side view of the membrane-perforating cap according to the present invention.
Figure 75:
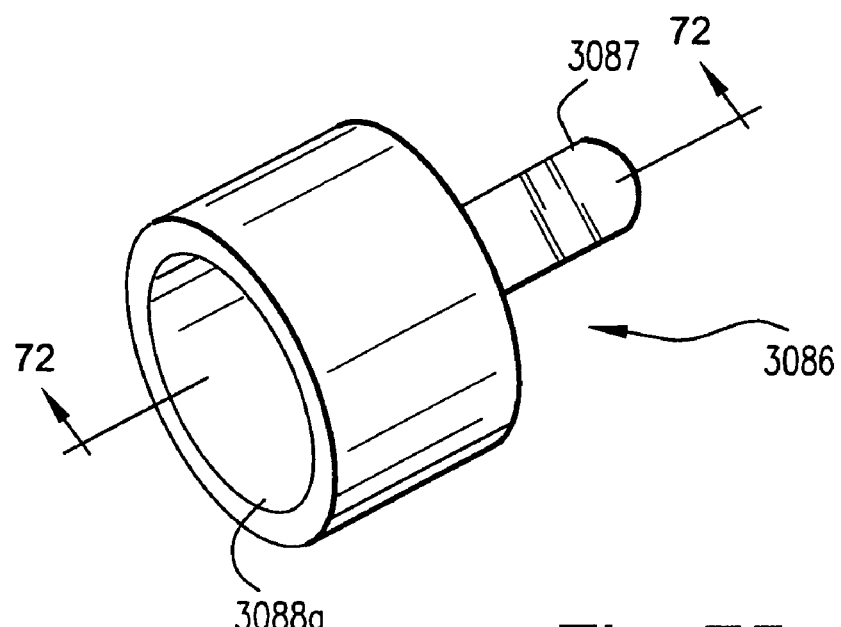
FIG. 75 is an isometric view of the membrane-perforating cap according to the present invention.
Figure 76:
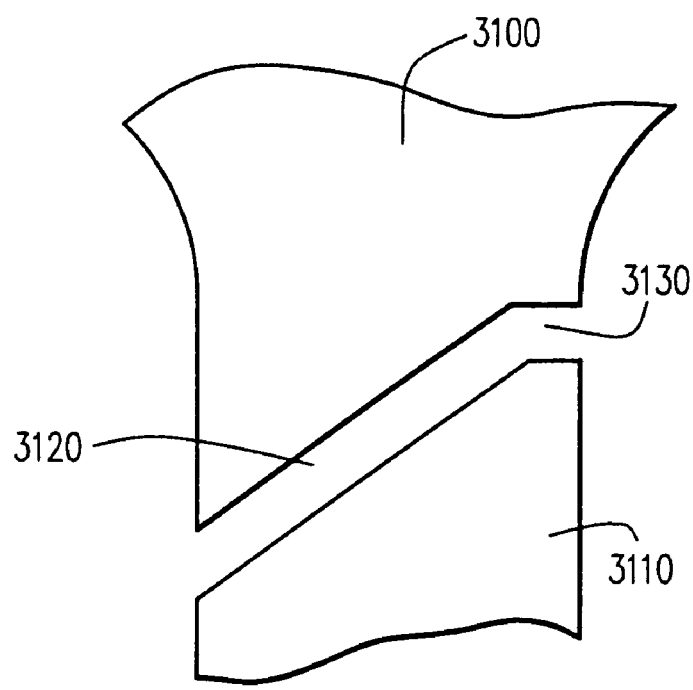
FIG. 76 is a cut section view of the septum showing an oblique orientation of the membrane.

FIGS. 72, 74 and 75 show a membrane perforating cap 3086 for perforating the membrane 3085. The cap 3086 includes a handle 3087 and recessed threads 3088 sized to be received over the luer receiver. The cap 3086 provides a smooth circumferential wall 3088a distal the recessed threads 3088 to allow the cap 3086 to fit over the receiver 3036 without threading. The recessed threads 3088 are sized to be received about lugs 3040 during threading immediately prior to use as will be discussed. The cap 3086 includes a projecting sharp spike 3089. The spike 3089 is recessed within the cap 3086 so as to be inaccessible to human fingers and so that it does not engage the membrane 3085 prior to threading. The recessed threads 3088 serve as a stop upon contact with lugs 3040 so that the spike 3089 does not penetrate the membrane 3085 when the cap is initially mounted on the receiver 3035. During manufacture, the cap 3086 is placed over the receiver 3036 partially threaded onto the lugs 3040 of the luer receiver 3036 to a position wherein the spike 3089 has not yet engaged and/or penetrated the membrane 3085.

An outer fixation shrink-wrap (not shown) is then applied to cover cap 3086, retainer 3034 to both bond and seal the cap member 3086 in this position with the spike 3089 above the membrane 3085 so that the cap 3086 is sealed and cannot be further advanced about the receiver 3036 and so that the membrane 3085 cannot be penetrated inadvertently. If preferred, a stop (not shown) can be provided below the cap 3086 adjacent the receiver 3036 during manufacture to limit advancement of the cap 3086 during manufacture. The stop is particularly useful if a recessed blade (such as a sharp angled blade having for example the configuration of a #11 surgical blade which can be mounted in alignment with the slit), is provided instead of a spike since such a blade would be preferably advanced by direct digital pressure against the cap rather than threading.

During operation, the wrap is removed and the cap member 3086 is rotated to advance the cap member 3086 over the luer receiver 3036 so that the spike 3089 perforates the membrane 3085. The cap 3086 is then rotated off the receiver 3036 and discarded after the membrane 3085 has been perforated. The luer receiver 3036 is now ready to receive a conventional luer tip 3054, which more easily penetrates the now perforated membrane 3085.

Figure 73:
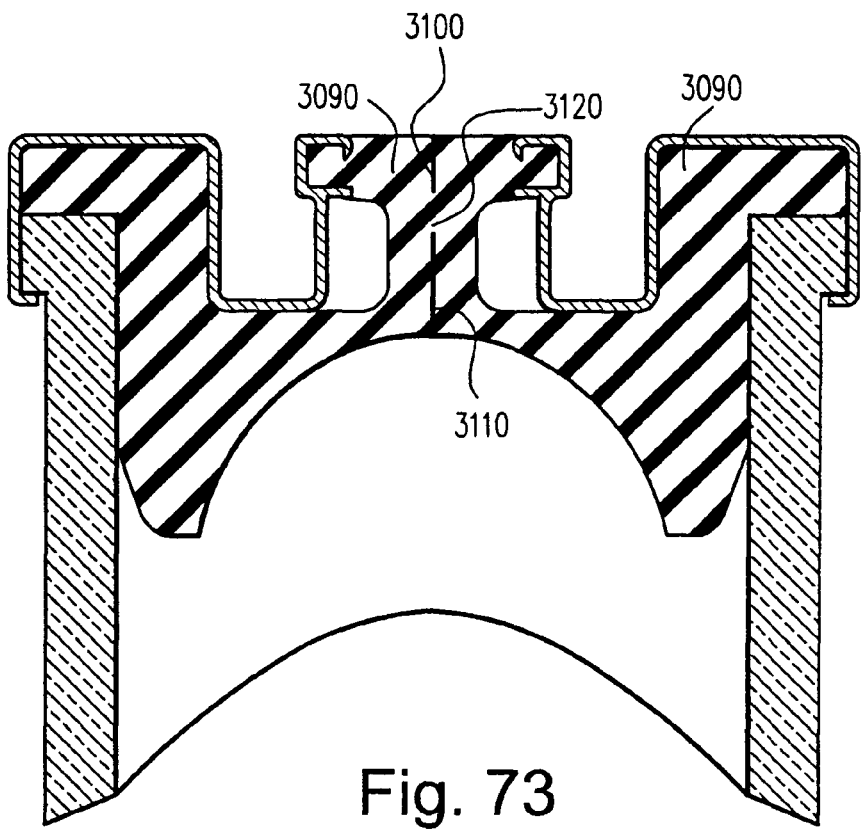
FIG. 73 is a cut, half-section view of an alternative embodiment of a luer access container according to the present invention.

In an alternative embodiment (shown in FIG. 73) which can be used with or without a membrane-perforating cap, the stopper 3090 is recessed to receive the conventional luer lock housing 3044. An upper slit 3100 is provided which is separated from a lower slit 3110 by a membrane 3120, which can be directly transverse or can be obliquely oriented as in FIG. 73. This configuration provides a greater mechanical advantage for the luer tip 3054 (see FIG. 71). As the luer tip 3054 advances it stretches the upper step portion 3130 of the membrane 3120 transverse to the slit 3100 to a greater extent at the upper membrane portion 3130, since the amount of transverse membrane stretched is less with this configuration the penetration force required to engage the membrane is less. Further the stress is focused on a singe narrow upper portion 3130 so that rupture requires less cumulative threading force. Alternatively, the membrane can have a directly oblique orientation without having an upper transverse step portion.

In both the embodiments, if preferred, the stopper can be covered and sealed by an external sealing shrink-wrap as is well known in the art and widely used for drug vials. Also the slit can be made to extend all of the way through the stopper if preferred. As an alternative to the separate cutting cap, a metal spike or sharp member can provided as integral with the retainer projecting inwardly toward the top membrane from the metal retainer. Such a cutting member can be forced into the membrane by the luer tip or by otherwise pushing against cutting member to provide perforation prior to or during luer entry into the face of the stopper.

Many modifications may be made within the scope of this teaching. For example opposing slots for receiving the lugs may be provided in the membrane-perforating cap to align a recessed blade with the slit. Also, the cap may be integrally molded with a cover over the end of the vial with a tear tab and circumferential weakening ring about the cap which extends below the cap functions as a stop and which upon removal allows advancement of the cap.

In operation the nurse removes the shrink-wrap and/or tears away the stop and then directly advances or threads the cap over the receiver until the membrane the spike or blade penetrates or cuts the membrane in alignment with the slit. The cap is then removed and discarded and the nurse threads a luer lock connector onto the receiver until the luer tip penetrates to sufficient depth into the slit to provide a flow path between the lumen through the luer tip and interior chamber of the drug vial. The septum now functions to provide a tight seal about the luer tip preventing leakage during both pressurization and aspiration of or from the chamber. The receiver seals after luer tip removal and then functions to provide multiple accesses of the vial chamber with conventional luer lock receivers.

Although the presently preferred embodiments have been described, it will be obvious to those skilled in the art that various changes and modifications can be made without departing from the invention. Thus, while the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A luer receiving valve, for fluid connection between a catheter in communication with a patient's vasculature and at least one fluid system, the fluid system having a luer lock connector including a luer tip, the luer receiving valve comprising:
a housing defining a chamber and at least two integral ports in fluid communication with the chamber, a first one of said ports being adapted for fluid connection to said catheter; and
an elastomeric septum mounted to said housing so as to be disposed at least partially within a second of said ports, said septum having an outer face and a sealed slit, said second port being sized to receive said luer tip of said fluid system luer lock connector, said second port defining a female luer sized to be received into and lockingly engaged with said luer lock connector of said fluid system when said luer tip is advanced against said septum;
wherein said septum has a longitudinal axis, an upper portion with said outer face and an extension portion projecting downwardly from said upper portion, said slit extending from adjacent said outer face through said upper portion and at least partially through said extension portion, the slit defining a long transverse axis, a sealing force being applied by said housing to said septum adjacent said outer face thereby to seal said slit at said outer face, said sealing force comprising at least one of an upward force and a force directed to a greater extent toward the long transverse axis of the slit than parallel to said long transverse axis, said extension portion having a width in a direction transverse to said slit that is less than a transverse width of said upper portion, said septum and said slit therein being sized and configured to receive at least a portion of said male luer end into said septum through said face and through at least a portion of said slit, at least a portion of said septum being displaced lateral to said longitudinal axis by said luer tip when said luer tip is advanced into said septum to define a displaced septum portion; and
at least one cavity defined lateral to said septum for receiving said displaced septum portion when said luer tip is advanced into said septum; wherein:
said housing at said second port defines a bore having a proximal end, said housing at said second port having an upward-facing surface adjacent said proximal end, at least a portion of said septum upper portion being mounted above said upward-facing surface.

2. The luer-receiving valve of claim 1, wherein:
said upward facing surface has an inner edge, said septum upper portion projecting proximal thereof.

3. The luer-receiving valve of claim 2, wherein:
said septum upper portion is mounted upon said upward-facing surface and above said inner edge, thereby covering said inner edge.

4. The luer-receiving valve of claim 3, wherein:
said septum upper portion covers substantially all of said inner edge.

5. The luer-receiving valve of claim 4, wherein said inner edge is substantially circular.

6. The luer-receiving valve of claim 2, wherein:
at least a portion of said septum upper portion is deflected by said inner edge, to forcibly seal said slit at said septum outer face.

7. The luer-receiving valve of claim 2, wherein:
said inner edge extends substantially around a circumference of said bore.

8. The luer-receiving valve of claim 1, wherein:
at least a portion of said septum upper portion is mounted upon said upward-facing surface.

9. The luer receiving valve of claim 1, wherein:
said upward-facing surface comprises a proximal rim of said housing at said second port.

10. The luer-receiving valve of claim 1, wherein at least a portion of said septum upper portion contacts said upward-facing surface.

11. The luer-receiving valve of claim 1, wherein:
at least a portion of said septum upper portion covers at least a portion of said upward-facing surface.

12. The luer-receiving valve of claim 1, wherein:
said upward-facing surface is a substantially circular annular surface.

13. The luer-receiving valve of claim 1, wherein:
at least a portion of said septum upper portion is deflected by said upward-facing surface, to forcibly seal said slit at said septum outer face.

14. The luer-receiving valve of claim 1, wherein:
at least a portion of said septum upper portion is compressed by said upward-facing surface, to forcibly seal said slit at said septum outer face.

15. A luer receiving valve, for fluid connection between a catheter in communication with a patient's vasculature and at least one fluid system, the fluid system having a luer lock connector including a luer tip, the luer receiving valve comprising:
a housing defining a chamber and at least two ports in fluid communication with the chamber, a first one of said ports being adapted for fluid connection to said catheter;
an elastomeric septum mounted to said housing so as to be disposed at least partially within a second of said ports, said septum having an outer face and a sealed slit, said second port being sized to receive said luer tip of said fluid system luer lock connector, said second port defining a female luer sized to be received into and lockingly engaged with said luer lock connector of said fluid system when said luer tip is advanced against said septum;
wherein said septum has a longitudinal axis, an upper portion with said outer face and an extension portion projecting downwardly from said upper portion, said slit extending from adjacent said outer face through said upper portion and at least partially through said extension portion, a sealing force being applied by said housing to said septum adjacent said outer face thereby to seal said slit at said outer face, said extension portion having a width in a direction transverse to said slit that is less than a transverse width of said upper portion, said septum and said slit therein being sized and configured to receive at least a portion of said male luer end into said septum through said face and through at least a portion of said slit, at least a portion of said septum being displaced lateral to said longitudinal axis by said luer tip when said luer tip is advanced into said septum to define a displaced septum portion; and at least one cavity defined lateral to said septum for receiving said displaced septum portion when said luer tip is advanced into said septum; wherein:

said housing at said second end defines a bore having a proximal end, said housing having a projecting portion adjacent said proximal end, said projecting portion projecting against and capturing at least a portion of said septum adjacent said proximal end.

16. The luer-receiving valve of claim 15, wherein:
said septum upper portion defines at least one lateral edge, said projecting portion compressing at least a portion of said septum upper portion adjacent one of said at least one lateral edges, capturing said septum adjacent thereto.

17. The luer-receiving valve of claim 16, wherein:
at least a portion of said projecting portion projects radially inward.

18. The luer-receiving valve of claim 17, wherein:
said septum has at least one perforation, adjacent said proximal end of said bore, extending at least partially through said septum adjacent said at least one lateral edge, said projecting portion projecting into said at least one perforation.

19. The luer-receiving valve of claim 15, wherein:
said projecting portion further compresses at least a portion of said septum upper portion.

20. The luer-receiving valve of claim 15, wherein: said projecting portion projects inwardly.

21. A luer receiving valve, for fluid connection between a catheter in communication with a patient's vasculature and at least one fluid system, the fluid system having a luer lock connector including a luer tip, the luer receiving valve comprising:

a housing defining a chamber and at least two ports in fluid communication with the chamber, a first one of said ports being adapted for fluid connection to said catheter;

an elastomeric septum mounted to said housing so as to be disposed at least partially within a second of said ports, said septum having an outer face and a sealed slit, said second port being sized to receive said luer tip of said fluid system luer lock connector, said second port defining a female luer sized to be received into and lockingly engaged with said luer lock connector of said fluid system when said luer tip is advanced against said septum;

wherein said septum has a longitudinal axis, an upper portion with said outer face and an extension portion projecting downwardly from said upper portion, said slit extending from adjacent said outer face through said upper portion and at least partially through said extension portion, the slit defining a long transverse axis, a sealing force being applied by a portion of said housing to said septum adjacent said outer face, said sealing force comprising at least one of an upward force and a force directed to a greater extent toward the long transverse axis of the slit than parallel to said long transverse axis to seal said slit at said outer face, said extension portion having a width in a direction transverse to said slit that is less than a transverse width of said upper portion, said septum and said slit therein being sized and configured to receive at least a portion of said male luer end into said septum through said face and through at least a portion of said slit, at least a portion of said septum being displaced lateral to said longitudinal axis by said luer tip when said luer tip is advanced into said septum to define a displaced septum portion; and at least one cavity defined lateral to said septum for receiving said displaced septum portion when said luer tip is advanced into said septum.

22. The luer receiving valve of claim 1, wherein said upper portion defines an inferior wall and said extension portion defines a lateral wall and wherein said at least one cavity is defined by said inferior wall and said lateral wall.

23. The luer receiving valve of claim 22, wherein the septum further includes a lower portion having a transverse width greater than said extension portion and defining an upper surface, said cavity being further defined by said upper surface of said lower portion.

24. A luer receiver for receiving a male luer tip, the receiver comprising:

a housing defining a chamber and at least two ports in fluid communication with the chamber; and a septum having a longitudinal axis and mounted to said housing so as to be disposed at least partially within one of said ports, said septum being formed at least in part from a first elastomeric material and having a proximal portion, an extension portion, and a central slit defined at least partially therethrough, said septum proximal portion including an upper portion having a width greater than a width of said extension portion;

a proximal end of said one port of said housing comprising a substantially continuous ring structure defining a platform, said upper portion of said septum being seated on said platform, wherein said ring structure includes diametrically opposed radially inwardly extending projections.

25. The luer receiver of claim 24, wherein said extension portion is disposed in said one port of said housing and has at least one reduced diameter section having a transverse diameter less than an inner diameter of said one port.

26. The luer receiver of claim 24, wherein said extension portion includes at least one cutout portion thereby to define said width thereof that is less than said width of said upper portion.

27. A luer receiver for receiving a male luer tip, the receiver comprising:

a housing defining a chamber and at least two ports in fluid communication with the chamber; and a septum having a longitudinal axis and mounted to said housing so as to be disposed at least partially within one of said ports, said septum being formed as least in part from a first elastomeric material and having a proximal portion, an extension portion, and a central slit defined at least partially therethrough, said septum proximal portion including an upper portion having a width greater than a width of said extension portion, a proximal end of said one port of said housing comprising a substantially continuous ring structure defining a platform, said upper portion of said septum being seated on said platform, wherein at least first and second diametrically opposed lateral voids are defined in said one port of said housing, distal of said ring structure.

28. The luer receiver of claim 27, wherein said voids are defined by cut outs that extend into a wall of said one port of said housing so as to define slots therein.

29. A luer receiving valve, for fluid connection between a catheter in communication with a patient's vasculature and at least one fluid system, the fluid system having a luer lock connector including a luer tip, the luer receiving valve comprising:
a housing defining a chamber and at least two ports in fluid communication with the chamber, a first one of said ports being adapted for fluid connection to said catheter;
an elastomeric septum mounted to said housing so as to be disposed at least partially within a second of said ports, said septum having an outer face and a sealed slit, said second port being sized to receive said luer tip of said fluid system luer lock connector, said second port defining a female luer sized to be received into and lockingly engaged with said luer lock connector of said fluid system when said luer tip is advanced against said septum;
wherein said septum has a longitudinal axis, an upper portion with said outer face and an extension portion projecting downwardly from said upper portion, said slit defining a long transverse axis and extending from adjacent said outer face through said upper portion and at least partially through said extension portion, a sealing force being applied by said housing to said septum adjacent said outer face thereby to seal said slit at said outer face, said sealing force comprising at least one of an upward force and a force directed to a greater extent toward the long transverse axis of the slit than parallel to said long transverse axis, said extension portion having a width in a direction transverse to said slit that is less than a transverse width of said upper portion, said septum and said slit therein being sized and configured to receive at least a portion of said male luer end into said septum through said face and through at least a portion of said slit, at least a portion of said septum being displaced lateral to said longitudinal axis by said luer tip when said luer tip is advanced into said septum to define a displaced septum portion; and
at least one cavity defined lateral to said septum for receiving said displaced septum portion when said luer tip is advanced into said septum;
wherein said housing has an upward facing upper surface at said second port, said upward facing upper surface at least partially inducing said sealing force and wherein said septum includes an upper portion mounted above said upward facing upper surface of said housing.

30. A luer receiver for receiving a male luer tip, the receiver comprising:
a housing defining a chamber and at least two ports in fluid communication with the chamber;
a septum having a longitudinal axis and mounted to said housing so as to be disposed at least partially within one of said ports, said septum being formed at least in part from a first elastomeric material and having a proximal portion, an extension portion, and a central slit defined at least partially therethrough, said septum proximal portion including an upper portion having a width greater than a width of said extension portion,
a proximal end of said one port of said housing comprising a substantially continuous ring structure defining a platform, said upper portion of said septum being seated on said platform,
wherein upper surfaces of diametrically opposed first and second portions of said ring structure are inclined from a more distal radially inner edge to a more proximal radially outer edge.

31. A luer receiving valve, for fluid connection between a catheter in communication with a patient's vasculature and at least one fluid system, the fluid system having a luer lock connector including a luer tip, the luer receiving valve comprising:
a housing defining a chamber and at least two ports in fluid communication with the chamber, a first one of said ports being adapted for fluid connection to said catheter, said housing having an upward facing upper surface at said second port; and
an elastomeric septum mounted to said housing so as to be disposed at least partially within a second of said ports, said septum having an outer face and, a sealed slit, said second port being sized to receive said luer tip of said fluid system luer lock connector, said second port defining a female luer sized to be received into and lockingly engaged with said luer lock connector of said, fluid system when said luer tip is advanced against said septum;
wherein said septum has a longitudinal axis, an upper portion with said outer face, said upper portion mounted above said housing upward facing upper surface, and an extension portion projecting downwardly from said upper portion, said slit defining a long transverse axis and extending from adjacent said outer face through said upper portion and at least partially through said extension portion, a sealing force being applied by said housing to said septum adjacent said outer face thereby to seal said slit adjacent said outer face, said sealing force comprising at least one of an upward force and a force directed to a greater extent toward the long transverse axis of the slit than parallel to said long transverse axis, said sealing force at least partially induced by said housing upward facing upper surface, said extension portion having a width in a direction transverse to said slit that is less than a transverse width of said upper portion, said septum and said slit therein being sized and configured to receive at least a portion of said male luer end into said septum through said face and through at least a portion of said slit, at least a portion of said septum being displaced lateral to said longitudinal axis by said luer tip when said luer tip is advanced into said septum to define a displaced septum portion; and
at least one cavity defined lateral to said septum for receiving said displaced septum portion when said luer tip is advanced into said septum.

32. A luer receiving valve, for fluid connection between a catheter in communication with a patient's vasculature and at least one fluid system, the fluid system having a luer lock connector including a luer tip, the luer receiving valve comprising:
a housing defining a chamber and at least two ports in fluid communication with the chamber, a first one of said ports being adapted for fluid connection to said catheter;
an elastomeric septum mounted to said housing so as to be disposed at least partially within a second of said ports, said septum having an outer face and a sealed slit, said second port being sized to receive said luer tip of said fluid system luer lock connector, said second port defining a female luer sized to be received into and lockingly engaged with said luer lock connector of said fluid system when said luer tip is advanced against said septum;
wherein said septum has a longitudinal axis, an upper portion with said outer face and an extension portion projecting downwardly from said upper portion, said slit defining a long transverse axis and extending from adjacent said outer face through said upper portion and at least partially through said extension portion, a sealing force being applied by said housing to said septum adjacent said outer face thereby to seal said slit at said outer face, said sealing force comprising at least one of an upward force and a force directed to a greater extent toward the long transverse axis of the slit than parallel to said long transverse axis, said extension portion having a width in a direction transverse to said slit that is less than a transverse width of said upper portion, said septum and said slit therein being sized and configured to receive at least a portion of said male luer end into said septum through said face and through at least a portion of said slit, at least a portion of said septum being displaced lateral to said longitudinal axis by said luer tip when said luer tip is advanced into said septum to define a displaced septum portion; and at least one cavity defined lateral to said septum for receiving said displaced septum portion when said luer tip is advanced into said septum; wherein:

said housing defines a proximal end of said second port; and at rest, at least a portion of said septum upper portion is deflected upward by said housing, adjacent said proximal end, to forcibly seal said slit at said septum outer face.

33. A luer receiving valve, for fluid connection between a catheter in communication with a patient's vasculature and at least one fluid system, the fluid system having a luer lock connector including a luer tip, the luer receiving valve comprising:

a housing defining a chamber and at least two ports in fluid communication with the chamber, a first one of said ports being adapted for fluid connection to said catheter;

an elastomeric septum mounted to said housing so as to be disposed at least partially within a second of said ports, said septum having an outer face and a sealed slit, said second port being sized to receive said luer tip of said fluid system luer lock connector, said second port defining a female luer sized to be received into and lockingly engaged with said luer lock connector of said fluid system when said luer tip is advanced against said septum;

wherein said septum has a longitudinal axis, an upper portion with said outer face and an extension portion projecting downwardly from said upper portion, said slit extending from adjacent said outer face through said upper portion and at least partially through said extension portion, a sealing force being applied by said housing to said septum adjacent said outer face thereby to seal said slit at said outer face, said extension portion having a width in a direction transverse to said slit that is less than a transverse width of said upper portion, said septum and said slit therein being sized and configured to receive at least a portion of said male luer end into said septum through said face and through at least a portion of said slit, at least a portion of said septum being displaced lateral to said longitudinal axis by said luer tip when said luer tip is advanced into said septum to define a displaced septum portion; and at least one cavity defined lateral to said septum for receiving said displaced septum portion when said luer tip is advanced into said septum; wherein:

said housing defines a proximal end of said second port; and said housing further comprises a means for capturing said septum against proximal displacement, said means positioned adjacent said proximal end for projecting inwardly against and capturing said septum adjacent said proximal end.

34. A luer receiving valve, for fluid connection between a catheter in communication with a patient's vasculature and at least one fluid system, the fluid system having a luer lock connector including a luer tip, the luer receiving valve comprising:

a housing defining a chamber and at least two ports in fluid communication with the chamber, a first one of said ports being adapted for fluid connection to said catheter;

an elastomeric septum mounted to said housing so as to be disposed at least partially within a second of said ports, said septum having an outer face and a sealed slit, said second port being sized to receive said luer tip of said fluid system luer lock connector, said second port defining a female luer sized to be received into and lockingly engaged with said luer lock connector of said fluid system when said luer tip is advanced against said septum;

wherein said septum has a longitudinal axis, an upper portion with said outer face and an extension portion projecting downwardly from said upper portion, said slit extending from adjacent said outer face through said upper portion and at least partially through said extension portion, a sealing force being applied by said housing to said septum adjacent said outer face thereby to seal said slit at said outer face, said extension portion having a width in a direction transverse to said slit that is less than a transverse width of said upper portion, said septum and said slit therein being sized and configured to receive at least a portion of said male luer end into said septum through said face and through at least a portion of said slit, at least a portion of said septum being displaced lateral to said longitudinal axis by said luer tip when said luer tip is advanced into said septum to define a displaced septum portion; and at least one cavity defined lateral to said septum for receiving said displaced septum portion when said luer tip is advanced into said septum; wherein:

said housing at said second port defines a longitudinal axis and a bore extending along said axis, said bore having a proximal end; said housing at said second port having a projecting portion adjacent said proximal end extending inwardly at least partially transverse to said longitudinal axis, said projecting portion projecting above at least a portion of said septum, engaging said septum so that said housing captures said septum adjacent said proximal end.

* * * * *